(12) United States Patent
Takaku et al.

(10) Patent No.: US 9,876,175 B2
(45) Date of Patent: Jan. 23, 2018

(54) ORGANIC ELECTROLUMINESCENT ELEMENT, MATERIAL FOR ORGANIC ELECTROLUMINESCENT ELEMENT, AND LIGHT EMITTING DEVICE, DISPLAY DEVICE AND LIGHTING DEVICE EACH USING ORGANIC ELECTROLUMINSCENT ELEMENT

(75) Inventors: Koji Takaku, Kanagawa (JP); Tetsu Kitamura, Kanagawa (JP); Toru Watanabe, Kanagawa (JP); Yosuke Yamamoto, Kanagawa (JP); Kimiatsu Nomura, Kanagawa (JP); Wataru Sotoyama, Kanagawa (JP); Saki Takada, Kanagawa (JP); Toshihiro Ise, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 646 days.

(21) Appl. No.: 14/239,696

(22) PCT Filed: Aug. 6, 2012

(86) PCT No.: PCT/JP2012/069951
§ 371 (c)(1),
(2), (4) Date: May 13, 2014

(87) PCT Pub. No.: WO2013/027565
PCT Pub. Date: Feb. 28, 2013

(65) Prior Publication Data
US 2014/0246659 A1    Sep. 4, 2014

(30) Foreign Application Priority Data

Aug. 22, 2011 (JP) ................................. 2011-180907

(51) Int. Cl.
*H01L 51/00* (2006.01)
*H05B 33/14* (2006.01)
(Continued)

(52) U.S. Cl.
CPC ........ *H01L 51/0056* (2013.01); *H01L 51/006* (2013.01); *H01L 51/0058* (2013.01);
(Continued)

(58) Field of Classification Search
CPC ......... C07C 13/00; C07C 13/32; C07C 13/62; C07C 13/64; C07C 43/267; C07C 211/61; C07C 217/94; C07C 323/38; C07C 2101/00; C07C 2101/12; C07C 2101/16; C07C 2103/00; C07C 2103/54; C07C 2103/93; C07C 2103/94; H05B 33/14; C07D 471/00; C07D 471/02; C07D 471/06; C07D 471/16; C07D 487/00; C07D 487/02; C07D 487/06; C07D 493/00; C07D 493/02; C07D 493/06; C07D 491/00; C07D 491/02; C07D 491/06; C07D 495/00; C07D 495/02; C07D 495/06; C07D 497/00; C07D 497/02; C07D 497/06; C07D 401/00; C07D 401/02; C07D 401/06; C07D 235/18; C07D 235/20; C07D 209/56; C07D 519/00; C07D 307/93; C07D 221/18; C07D 209/80;
(Continued)

(56) References Cited

U.S. PATENT DOCUMENTS

2004/0076853 A1* 4/2004 Jarikov ................. C09K 11/06
                                                                    428/690
2008/0124455 A1   5/2008 Shin et al.
(Continued)

FOREIGN PATENT DOCUMENTS

| JP | 2010073987 | 4/2010 | |
|---|---|---|---|
| JP | 2010085504 | 4/2010 | |
| JP | 2010111620 | 5/2010 | |
| JP | 2011037854 | 2/2011 | |
| JP | 2011051969 | 3/2011 | |
| JP | 2011079822 | 4/2011 | |
| WO | 2010012328 | 2/2010 | |
| WO | WO 2010053210 A1 * | 5/2010 | ............. C07C 13/62 |

(Continued)

*Primary Examiner* — Andrew K Bohaty
(74) *Attorney, Agent, or Firm* — Riverside Law LLP

(57) ABSTRACT

An organic electroluminescent element including a substrate, a pair of electrodes including an anode and a cathode, disposed on the substrate, and at least one organic layer including a light emitting layer, disposed between the electrodes, in which a compound represented by the following formula (I) is contained in any layer of the at least one organic layer. The organic electroluminescent element has high luminous efficiency and a strong effect of improving the durability by driving aging:

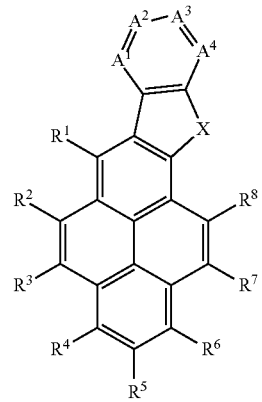

Formula (I)

wherein X, $A^1$, $A^2$, $A^3$, $A^4$, and $R^1$ to $R^8$ are as defined herein.

16 Claims, 1 Drawing Sheet

(51) Int. Cl.
*H01L 51/50* (2006.01)
*C07D 209/56* (2006.01)

(52) U.S. Cl.
CPC ...... *H01L 51/0061* (2013.01); *H01L 51/0072* (2013.01); *H01L 51/0073* (2013.01); *H01L 51/0074* (2013.01); *H01L 51/50* (2013.01); *H05B 33/14* (2013.01); *C07D 209/56* (2013.01); *C09K 2211/1011* (2013.01); *C09K 2211/1014* (2013.01); *C09K 2211/1029* (2013.01); *C09K 2211/1088* (2013.01); *H01L 51/5012* (2013.01)

(58) Field of Classification Search
CPC . C09K 11/06; C09K 2211/00; C09K 2211/10; C09K 2211/1003; C09K 2211/1011; C09K 2211/1018; C09K 2211/1029; C09K 2211/1033; C09K 2211/1037; C09K 2211/1044; C09K 2211/1088; C09K 2211/1092; C09K 2211/1096; H01L 51/0032; H01L 51/005; H01L 51/0051; H01L 51/0052; H01L 51/0054; H01L 51/0056; H01L 51/0057; H01L 51/0058; H01L 51/0059; H01L 51/006; H01L 51/0071; H01L 51/0072; H01L 51/0073; H01L 21/0074; H01L 51/0081; H01L 51/0061; H01L 51/0065; H01L 51/0068; H01L 51/0094; H01L 51/50; H01L 51/5012; H01L 51/5016; H01L 51/5024; H01L 51/5203
USPC ..... 428/690, 691, 917, 411.4, 336; 427/458, 427/66; 313/500–512; 257/40, 88–104, 257/E51.001–E51.052; 252/301.16–301.35; 546/14, 30, 31, 41; 548/406, 407, 417; 549/24, 41, 214, 381, 549/456; 556/406; 585/26, 27; 544/229, 544/245, 338
See application file for complete search history.

(56) References Cited

U.S. PATENT DOCUMENTS

| | | | |
|---|---|---|---|
| 2010/0237773 A1* | 9/2010 | Nomura | C07D 403/12 313/504 |
| 2011/0031484 A1* | 2/2011 | Lee | C07D 209/90 257/40 |
| 2013/0001524 A1* | 1/2013 | Lim | C07D 403/12 257/40 |

FOREIGN PATENT DOCUMENTS

| | | |
|---|---|---|
| WO | 2010074520 | 7/2010 |
| WO | 2010114264 | 10/2010 |
| WO | 2011037429 | 3/2011 |

* cited by examiner

ORGANIC ELECTROLUMINESCENT ELEMENT, MATERIAL FOR ORGANIC ELECTROLUMINESCENT ELEMENT, AND LIGHT EMITTING DEVICE, DISPLAY DEVICE AND LIGHTING DEVICE EACH USING ORGANIC ELECTROLUMINSCENT ELEMENT

CROSS-REFERENCE TO RELATED APPLICATIONS

This application is a national stage entry of International Patent Application No. PCT/JP2012/069951, filed 6 Aug. 2012, which in turn claims priority to, and the benefit of, Japanese Patent Application No. 2011-180907, filed 22 Aug. 2011, all of which are incorporated herein by reference in their entireties.

TECHNICAL FIELD

The present invention relates to an organic electroluminescent element and a material for an organic electroluminescent element used therein. The present invention further relates to a light emitting device, a display device, or an illumination device, using the organic electroluminescent element.

BACKGROUND ART

Organic electroluminescent elements (which may hereinafter also be referred to as "elements" or "organic EL elements") are light emitting elements which have organic layers between a pair of electrodes, and utilize, for light emitting, energy of the exciton generated as a result of recombination of electrons injected from a cathode and holes injected from an anode in the organic layer. Since the organic electroluminescent elements are capable of high-luminance light emitting at a low voltage, have a high response speed, and are relatively thin and light-weight, it is expected that the element can be employed in a wide range of applications, and the elements have been actively researched and developed. Above all, it is important to develop an organic electroluminescent element having high luminous efficiency and good durability in applications with displays, and the like, and the results of studies on various research and development have been reported.

For example, PTL 1 describes that it is possible to attain a longer service life in the blue region of an element, using a material in which a ring is formed with a single bond and a methylene chain with respect to a fused ring structure such as pyrene as a fluorescent material. This literature exemplifies several compounds in which 2-aryl pyrene is fused with a pyrene skeleton via a methylene chain are exemplified, but only the evaluation of 1-aryl pyrene has been conducted in Examples.

PTL 2 describes that a compound in which 2-aryl pyrene is fused with a pyrene skeleton via a methylene chain or a nitrogen atom linking group can be used as a material for a hole transporting layer, a light emitting layer, or an electron transporting layer of an organic electroluminescent element, or the like, and it is thus possible to achieve higher efficiency and a longer service life.

In addition, PTL 3 describes examples of a compound in which the 1-position and the 2-position of pyrene are fused, and further describes that when the compound is used as a alight emitting material, a host compound, or the like of an organic electroluminescent element, the durability during storage and driving is excellent and the characteristics of high efficiency, low voltage, and high luminance are exhibited.

CITATION LIST

Patent Literature

[PTL 1] WO2010/012328
[PTL 2] JP-A-2011-79822
[PTL 3] JP-A-2011-51969

SUMMARY OF INVENTION

Technical Problem

On the other hand, organic electroluminescent elements have recently entered the stage for practical use, and as a practical method for improving the durability of the organic electroluminescent elements, a case where an aging treatment is carried out may be mentioned. The aging treatment is a treatment, in which an organic electroluminescent element is allowed to develop the deterioration in advance by driving and light emission before it is sold as a product. By allowing the element to develop the initial deterioration artificially, the initial deterioration is not shown after the aging, and consequently, it is possible to improve the durability of the element. The aging treatment is described on page 273 of "State-of-the-Art Technology Trend of Organic EL Display" (2003, Information Facility Co., Ltd.).

In this regard, the present inventors have investigated the organic electroluminescent elements described in PTLs 1 to 3, and have found that the organic electroluminescent elements described therein could not be substantially improved in driving durability by electrical current aging, thus there is still a demand for improvement of durability for practical use.

It is an object of the present invention by solving the problems to provide an organic electroluminescent element, which has high luminous efficiency and a strong effect of improving the durability by driving aging.

Solution to Problem

Therefore, the present inventors have conducted extensive investigations for the purpose of providing an organic electroluminescent element, which has high luminous efficiency and a strong effect of improving the durability by driving aging. As a result, they have found that when a pyrene derivative having a specific structure other than those in PTLs 1 to 3, in which an aryl group of 2-aryl pyrene forms a fused ring only with a pyrene ring, but there is no other fused ring structure, is used, the above-mentioned problems can be solved, thereby providing the present invention as described below.

[1] An organic electroluminescent element including a substrate, a pair of electrodes including an anode and a cathode, disposed on the substrate, and at least one organic layer including a light emitting layer, disposed between the electrodes, in which at least one kind of compound represented by the following general formula (I) is contained in any layer of the at least one organic layer.

[Chem. 1]

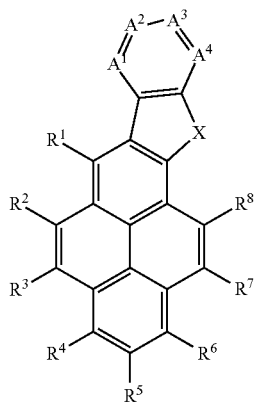

General formula (I)

(In the general formula (I), X represents a linking group. $A^1$, $A^2$, $A^3$ and $A^4$ each independently represent C—R or an N atom. R's each independently represent a hydrogen atom or a substituent. However, there is no case where adjacent substituents selected from $R^1$ to $R^8$ are bonded to each other to form a ring.)

[2] In the organic electroluminescent element as described in [1], in the general formula (I), X is preferably $CR^{12}R^{13}$, $NR^{14}$, $SiR^{15}R^{16}$ ($R^{12}$, $R^{13}$, $R^{14}$, $R^{15}$ and $R^{16}$ each independently represent a fluorine atom, an alkyl group, an aryl group, or a heteroaryl group), an O atom, or an S atom.

[3] In the organic electroluminescent element as described in [1] or [2], in the general formula (I) A', $A^2$, $A^3$ and $A^4$ preferably each independently represent C—R.

[4] In the organic electroluminescent element as described in any one of [1] to [3], the compound represented by the general formula (I) is preferably a compound represented by the following general formula (II).

[Chem. 2]

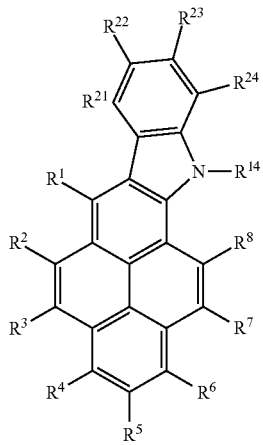

General formula (II)

(In the general formula (II), $R^1$ to $R^8$ and $R^{21}$ to $R^{24}$ represent a hydrogen atom or a substituent. However, there is no case where adjacent substituents selected from $R^1$ to $R^8$, $R^{21}$ to $R^{24}$ are bonded to each other to form a ring. $R^{14}$ represents an alkyl group, an aryl group, or a heteroaryl group.)

[5] In the organic electroluminescent element as described in any one of [1] to [4], in the compound represented in the general formula (I), at least one of $R^4$ and $R^6$ is preferably an aryl group having 6 to 30 carbon atoms, a heteroaryl group having 3 to 30 carbon atoms, or a di-substituted amino group.

[6] In the organic electroluminescent element as described in any one of [1] to [5], in the compound represented by in the general formula (I), $R^4$ and $R^6$ are preferably each independently an aryl group having 6 to 30 carbon atoms or a heteroaryl group having 3 to 30 carbon atoms.

[7] In the organic electroluminescent element as described in any one of [1] to [6], in the compound represented by in the general formula (I), $R^1$, $R^2$, $R^3$, $R^5$, $R^7$ and $R^8$ are preferably a hydrogen atom.

[8] In the organic electroluminescent element as described in any one of [1] to [7], the molecular weight of the compound represented by the general formula (I) is preferably 510 to 840.

[9] In the organic electroluminescent element as described in any one of [1] to [8], the compound represented by the general formula (I) is preferably contained in the light emitting layer.

[10] In the organic electroluminescent element as described in any one of [1] to [9], the compound represented by the general formula (I) is preferably a light emitting material contained in the light emitting layer.

[11] In the organic electroluminescent element as described in [10], further including a host material in the light emitting layer.

[12] In the organic electroluminescent element as described in [11], the host material preferably has an anthracene skeleton.

[13] A light emitting device using the organic electroluminescent element as described in any one of [1] to [12].

[14] A display device using the organic electroluminescent element as described in any one of [1] to [12].

[15] An illumination device using the organic electroluminescent element as described in any one of [1] to [12].

[16] A light emitting material for an organic electroluminescent element, represented by the following general formula (I).

[Chem. 3]

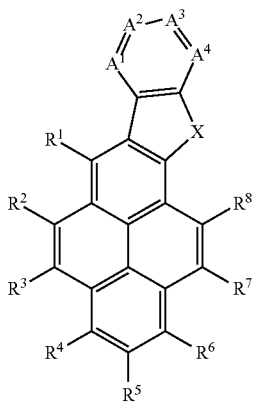

General formula (I)

(In the general formula (I), X represents a linking group. $A^1$, $A^2$, $A^3$ and $A^4$ each independently represent C—R or an N atom. R's each independently represent a hydrogen atom or a substituent. However, there is no case where adjacent substituents selected from $R^1$ to $R^8$ are bonded to each other to form a ring.)

Advantageous Effects of Invention

The organic electroluminescent element of the present invention has advantageous effects in that it has good high luminous efficiency and a strong effect of improving the durability by driving aging. In addition, when the compound of the present invention is used, such an excellent organic electroluminescent element can be easily prepared.

DESCRIPTION OF EMBODIMENTS

Figure 1:
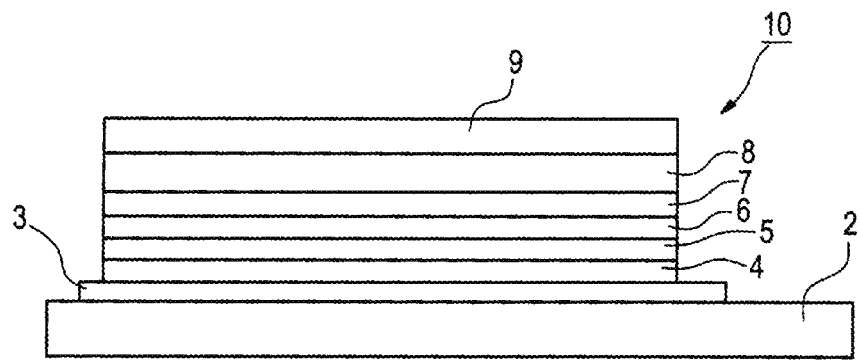
FIG. 1 is a schematic view showing one example of a configuration of an organic electroluminescent element according to the present invention.

Hereinafter, the details of the present invention will be described. The description of the configuration requirements as described below is based on representative embodiments and specific examples of the present invention, but the present invention is not limited to these embodiments and specific examples. Incidentally, in the present specification, the range expressed with "to" means a range including the numerical values before and after "to" as the lower limit and the upper limit, respectively.

[Material for Organic Electroluminescent Element, Represented by General Formula (I)]

The organic electroluminescent element of the present invention is a compound represented by the following general formula (I). In the organic electroluminescent element of the present invention as described later, the organic layer constituting the organic electroluminescent element contains the compound represented by the general formula (I).

[Chem. 4]

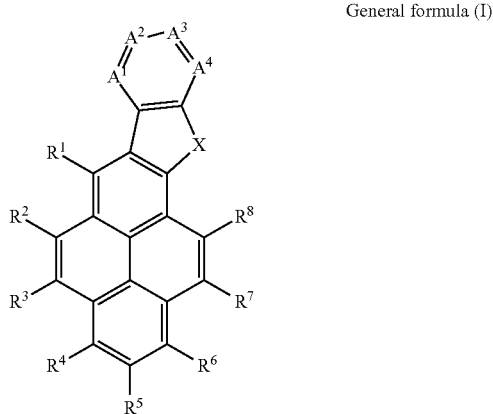

General formula (I)

(In the general formula (I), X represents a linking group. $A^1$, $A^2$, $A^3$ and $A^4$ each independently represent C—R or an N atom. R's each independently represent a hydrogen atom or a substituent. However, there is no case where adjacent substituents selected from $R^1$ to $R^8$ are bonded to each other to form a ring.)

Not wishing to be restricted to any theory, when the compound represented by the general formula (I) is used as a material for an organic electroluminescent element, the improvement rate of the driving durability by an aging treatment is very high. It has been completely not known in the related art that a compound having a structure represented by the general formula (I) exhibits such an effect, and the organic electroluminescent element exhibiting such an effect becomes advantageous when it is mounted on a display.

Hereinbelow, the compound represented by the general formula (I) will be described in detail.

In the present invention, in the description of the general formula (I), the hydrogen atom includes isotopes thereof (deuterium and the like), and the atom additionally constituting the substituent includes isotopes thereof.

In the present invention, when referring to a "substituent", the substituent may be further substituted. For example, when the "alkyl group" is referred to in the present invention, it includes an alkyl group substituted with a fluorine atom (for example, a trifluoromethyl group) and an alkyl group substituted with an aryl group (for example, a triphenylmethyl group), but when "an alkyl group having 1 to 6 carbon atoms" is referred to herein, it represents any of alkyl groups having 1 to 6 carbon atoms, including the alkyl groups which are substituted.

In the general formula (I), X represents a linking group. Specifically, X represents a divalent linking group, not a single bond. The X is preferably $CR^{112}R^{113}$, $NR^{114}$, $SiR^{115}R^{116}$, an O atom, or an S atom.

Examples of $R^{112}$, $R^{113}$, $R^{115}$ and $R^{116}$ (substituents at carbon atoms and substituents at silicon atoms) include the following Substituent Group A.

<<Substituent Group A>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, anthranyl), amino group (preferably having 0 to 30 carbon atoms, more preferably having 0 to 20 carbon atoms, and particularly preferably having 0 to 10 carbon atoms; for example, amino, methylamino, dimethylamino, diethylamino, dibenzylamino, diphenylamino, and ditolylamino), an alkoxy group (preferably having 1 to 30 carbon atoms, more preferably having 1 to 20 carbon atoms, and particularly preferably having 1 to 10 carbon atoms; for example, methoxy, ethoxy, butoxy, and 2-ethylhexyloxy), and aryloxy group (preferably having 6 to 30 carbon atoms, more preferably having 6 to 20 carbon atoms, and particularly preferably having 6 to 12 carbon atoms; for example, phenyloxy, 1-naphthyloxy, and 2-naphthyloxy), a heterocyclic oxy group (preferably having 1 to 30 carbon atoms, more preferably having 1 to 20 carbon atoms, and particularly preferably having 1 to 12 carbon atoms; for example, pyridyloxy, pyrazyloxy, pyrimidyloxy, and quinolyloxy), an acyl group (preferably having 2 to 30 carbon atoms, more preferably having 2 to 20 carbon atoms, and particularly preferably having 2 to 12 carbon atoms; for example, acetyl, benzoyl, formyl, and pivaloyl), an alkoxycarbonyl group (preferably having 2 to 30 carbon atoms, more preferably having 2 to 20 carbon atoms, and particularly preferably having 2 to 12 carbon atoms; for example, methoxycarbonyl and ethoxycarbonyl), an aryloxycarbonyl group (preferably having 7 to 30 carbon atoms, more preferably having 7 to 20 carbon atoms, and particularly preferably having 7 to 12 carbon atoms; for example, phenyloxycarbonyl), an acyloxy group (preferably having 2 to 30 carbon atoms, more preferably having 2 to 20 carbon atoms, and particularly preferably having 2 to 10 carbon atoms; for example, acetoxy and benzoyloxy), an acylamino group (preferably having 2 to 30 carbon atoms, more preferably having 2 to 20 carbon atoms, and particularly preferably having 2 to 10 carbon atoms; for example, acetylamino and benzoylamino), an alkoxycarbonylamino group (preferably having 2 to 30 carbon atoms, more preferably having 2 to 20 carbon atoms, and particularly preferably having 2 to 12 carbon atoms; for example, methoxycarbonylamino), an aryloxycarbonylamino group (preferably having 7 to 30 carbon atoms, more preferably having 7 to 20 carbon atoms, and particularly preferably having 7 to 12 carbon atoms; for example, phenyloxycarbonylamino), a sulfonylamino group (preferably having 1 to 30 carbon atoms, more preferably having 1 to 20 carbon atoms, and particularly preferably having 1 to 12 carbon atoms; for example, methanesulfonylamino and benzenesulfonylamino), a sulfamoyl group (preferably having 0 to 30 carbon atoms, more preferably having 0 to 20 carbon atoms, and particularly preferably having 0 to 12 carbon atoms; for example, sulfamoyl, methylsulfamoyl, dimethylsulfamoyl, and phenylsulfamoyl), a carbamoyl group (preferably having 1 to 30 carbon atoms, more preferably having 1 to 20 carbon atoms, and particularly preferably having 1 to 12 carbon atoms; for example, carbamoyl, methylcarbamoyl, diethylcarbamoyl, and phenylcarbamoyl), an alkylthio group (preferably having 1 to 30 carbon atoms, more preferably having 1 to 20 carbon atoms, and particularly preferably having 1 to 12 carbon atoms; for example, methylthio and ethylthio), an arylthio group (preferably having 6 to 30 carbon atoms, more preferably having 6 to 20 carbon atoms, and particularly preferably having 6 to 12 carbon atoms; for example, phenylthio), a heterocyclic thio group (preferably having 1 to 30 carbon atoms, more preferably having 1 to 20 carbon atoms, and particularly preferably having 1 to 12 carbon atoms; for example, pyridylthio, 2-benzoimizolylthio, 2-benzoxazolylthio, and 2-benzothiazolylthio), a sulfonyl group (preferably having 1 to 30 carbon atoms, more preferably having 1 to 20 carbon atoms, and particularly preferably having 1 to 12 carbon atoms; for example, mesyl and tosyl), a sulfinyl group (preferably having 1 to 30 carbon atoms, more preferably having 1 to 20 carbon atoms, and particularly preferably having to 12 carbon atoms; for example, methanesulfinyl and benzenesulfinyl), a ureido group (preferably having 1 to 30 carbon atoms, more preferably having 1 to 20 carbon atoms, and particularly preferably having 1 to 12 carbon atoms; for example, ureido, methylureido, and phenylureido), phosphoramide group (preferably having 1 to 30 carbon atoms, more preferably having 1 to 20 carbon atoms, and particularly preferably having 1 to 12 carbon atoms; for example, diethylphosphoramide and phenylphosphoramide), a hydroxy group, a mercapto group, a halogen atom (for example, a fluorine atom, a chlorine atom, a bromine atom, and an iodine atom), a cyano group, a sulfo group, a carboxyl group, a nitro group, a hydroxamic group, a sulfino group, a hydrazino group, an imino group, a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group), a silyl group (preferably having 3 to 40 carbon atoms, more preferably having 3 to 30 carbon atoms, and particularly preferably having 3 to 24 carbon atoms; for example, trimethylsilyl and triphenylsilyl), a silyloxy group (preferably having 3 to 40 carbon atoms, more preferably having 3 to 30 carbon atoms, and particularly preferably having 3 to 24 carbon atoms; for example, trimethylsilyloxy and triphenylsilyloxy), and a phosphoryl group (for example, a diphenylphosphoryl group and a dimethylphosphoryl group). These substituents may be further substituted, and examples of the additional substituent include the groups selected from the Substituent Group A as described above. Further, the substituent substituted with a substituent may be further substituted, and examples of the additional substituent include the groups selected from the Substituent Group A as described above. In addition, the substituent substituted with the substituent substituted with a substituent may be further substituted, and examples of the additional substituent include the groups selected from the Substituent Group A as described above.

Examples of $R^{114}$ (substituents at nitrogen atoms) include the following Substituent Group B.

<<Substituent Group B>>

An alkyl group (preferably having 1 to 30 carbon atoms, more preferably having 1 to 20 carbon atoms, and particularly preferably having 1 to 10 carbon atoms; for example, methyl, ethyl, isopropyl, t-butyl, n-octyl, n-decyl, n-hexadecyl, cyclopropyl, cyclopentyl, and cyclohexyl), an alkenyl group (preferably having 2 to 30 carbon atoms, more preferably having 2 to 20 carbon atoms, and particularly preferably having 2 to 10 carbon atoms; for example, vinyl, allyl, 2-butenyl, and 3-pentenyl), an alkynyl group (preferably having 2 to 30 carbon atoms, more preferably having 2 to 20 carbon atoms, and particularly preferably having 2 to 10 carbon atoms; for example, propargyl and 3-pentynyl), an aryl group (preferably having 6 to 30 carbon atoms, more preferably having 6 to 20 carbon atoms, and particularly preferably having 6 to 12 carbon atoms; for example, phenyl, p-methylphenyl, naphthyl, and anthranyl), a cyano group, and a heterocyclic group (inclusive of an aromatic heterocyclic group, which preferably has 1 to 30 carbon atoms, and more preferably 1 to 12 carbon atoms and in which examples of the hetero atom include a nitrogen atom, an oxygen atom, a sulfur atom, a phosphorus atom, a silicon atom, a selenium atom, and a tellurium atom; and specific examples thereof include pyridyl, pyrazinyl, pyrimidyl, pyridazinyl, pyrrolyl, pyrazolyl, triazolyl, imidazolyl, oxazolyl, triazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzoimidazolyl, benzothiazolyl, a carbazolyl group, an azepinyl group, and a silolyl group). These substituents may be further substituted, and examples of the additional substituent include the groups selected from the Substituent Group A as described above. Further, the substituent substituted with a substituent may be further substituted, and examples of the additional substituent include the groups selected from the Substituent Group A as described above. In addition, the substituent substituted with the substituent substituted with a substituent may be further substituted, and examples of the additional substituent include the groups selected from the Substituent Group A as described above.

X is more preferably $CR^{12}R^{13}$, $NR^{14}$, $SiR^{15}R^{16}$ ($R^{12}$, $R^{13}$, $R^{14}$, $R^{15}$ and $R^{16}$ are more preferably each independently a fluorine atom, an alkyl group, an aryl group, or a heteroaryl group), an O atom, or an S atom, particularly preferably $CR^{12}R^{13}$, $NR^{14}$, an O atom, or an S atom, and more particularly preferably $NR^{14}$.

$R^{12}$, $R^{13}$, $R^{15}$ and $R^{16}$ are more preferably each independently any one of a fluorine atom, a linear, branched, or cyclic alkyl group having 1 to 10 carbon atoms; an aryl group having 6 to 14 carbon atoms; and a heteroaryl group having 5 to 20 carbon atoms and containing any one of N, O, and S as a hetero atom; and particularly preferably a linear or branched alkyl group having 1 to 6 carbon atoms. In addition, from the viewpoint of easiness of synthesis, it is preferable that $R^{12}$ and $R^{13}$ be the same substituents. Further, from the viewpoint of the same, it is preferable that $R^{15}$ and $R^{16}$ be the same substituents.

$R^{12}$, $R^{13}$, $R^{15}$ and $R^{16}$ may be combined with each other to form a 5- or 6-membered ring. The 5- or 6-membered ring thus formed may be any one of a cycloalkyl ring, a cycloalkenyl ring, and a heterocycle. Examples of the heterocycle include those containing 1 to 3 hetero atoms selected from a group consisting of a nitrogen atom, an oxygen atom, and a sulfur atom as a ring-constituting atom. The 5- or 6-membered ring thus formed may have a substituent, examples of the substituent at carbon atoms include the Substituent Group A as described above, and examples of the substituent at nitrogen atoms include the Substituent Group B as described above.

$R^{14}$ is preferably an alkyl group, a perfluoroalkyl group, or an aryl group. $R^{14}$ is more preferably any one of a linear, branched, or cyclic alkyl group having 1 to 10 carbon atoms; an aryl group having 6 to 50 carbon atoms; and a heteroaryl group having 5 to 20 carbon atoms and at least one of N, O, and S as a hetero atom. $R^{14}$ is more preferably an aryl group having 6 to 14 carbon atoms; or a heteroaryl group having 5 to 20 carbon atoms and at least one of N, O, and S as a hetero atom.

$R^{14}$ may have an additional substituent, and the substituent is not particularly limited, but is preferably an alkyl group or an aryl group. The alkyl group as used herein is preferably an unsubstituted linear alkyl group, an unsubstituted branched alkyl group, an unsubstituted cycloalkyl group, or a perfluoroalkyl group; more preferably a linear alkyl group having 1 to 6 carbon atoms, a branched alkyl group having 1 to 6 carbon atoms, or a perfluoroalkyl group having 1 to 6 carbon atoms; particularly preferably a methyl group, an ethyl group, an isopropyl group, a t-butyl group, a t-amyl group, a neopentyl group, or a trifluoromethyl group; and more particularly preferably a methyl group, an ethyl group, an isopropyl group, or a t-butyl group. On the other hand, the aryl group as used herein is preferably an aryl group having 6 to 14 carbon atoms, more preferably an aryl group having 6 to 10 carbon atoms, and particularly preferably a phenyl group.

In the general formula (I), $A^1$, $A^2$, $A^3$ and $A^4$ each independently represent C—R or an N atom. R's each independently represent a hydrogen atom or a substituent, but there is no case where R's, which are present in plural, are bonded to each other to form a ring.

The number of nitrogen atoms contained in $A^1$, $A^2$, $A^3$ and $A^4$ is preferably 0 to 2, more preferably 0 or 1, and particularly preferably 0. That is, as a preferred example, a case where all of $A^1$ to $A^4$ be all C—R may be mentioned. The preferred positions of nitrogen atoms in the case where nitrogen atoms are contained in $A^1$, $A^2$, $A^3$, and $A^4$ are not particularly limited, but it is preferable that nitrogen atoms be not adjacent to each other.

R's in the case where $A^1$, $A^2$, $A^3$ and $A^4$ represent C—R each independently represent a hydrogen atom or a substituent, but there is no case where R's, which are present in plural, are bonded to each other to form a ring.

Examples of R in the case where $A^1$, $A^2$, $A^3$ and $A^4$ represent C—R included, in addition to a hydrogen atom, the Substituent Group A as described above. Above all, R is preferably a substituent having any one of a fluorine atom, an alkyl group, a silyl group, an aryl group, an aryloxy group, a cyano group, and an amino group, and specific examples thereof include a fluorine atom, an alkyl group, a perfluoroalkyl group, a trialkylsilyl group, a phenyl group, a phenoxy group, and a di-substituted amino group. R more preferably represent a hydrogen atom, an alkyl group, a silyl group, an aryl group, an aryloxy group, or a di-substituted amino group, particularly preferably a hydrogen atom, an alkyl group, or a di-substituted amino group, and more particularly preferably a hydrogen atom or an alkyl group.

The alkyl group represented by R is preferably an unsubstituted linear alkyl group, an unsubstituted branched alkyl group, an unsubstituted cycloalkyl group, or a perfluoroalkyl group, more preferably a linear alkyl group having 1 to 6 carbon atoms, a branched alkyl group having 1 to 6 carbon atoms, or a perfluoroalkyl group having 1 to 6 carbon atoms, still more a methyl group, an ethyl group, an isopropyl group, a t-butyl group, a t-amyl group, a neopentyl group, or a trifluoromethyl group, and particularly preferably a methyl group, an ethyl group, an isopropyl group, or a t-butyl group.

The substituted or unsubstituted aryl group represented by R is preferably an aryl group having 6 to 30 carbon atoms, more preferably a phenyl group, a naphthyl group, an anthryl group, a phenanthryl group, or a pyrenyl group, and particularly preferably a phenyl group or a naphthyl group. The di-substituted amino group represented by R is preferably an N,N-diarylamino group.

Examples of the substituent represented by $R^1$ to $R^8$ in the general formula (I) include the Substituent Group A as described above.

At least one of $R^1$ to $R^8$ in the general formula (I) is preferably an aryl group having 6 to 30 carbon atoms, a heteroaryl group having 3 to 30 carbon atoms, or a di-substituted amino group. Above all, at least one of $R^1$ to $R^8$ is preferably an aryl group having 6 to 30 carbon atoms, a heteroaryl group having 3 to 30 carbon atoms, or a di-substituted amino group, and more preferably an aryl group having 6 to 30 carbon atoms, or a di-substituted amino group.

The aryl group having 6 to 30 carbon atoms, which is preferable as $R^1$ to $R^8$ is preferably a phenyl group, a naphthyl group, an anthryl group, a phenanthryl group, or a pyrenyl group, and particularly preferably a phenyl group or a naphthyl group.

The heteroaryl group having 3 to 30 carbon atoms as a preferred substituent as $R^1$ to $R^8$ is preferably a heteroaryl group having 3 to 30 carbon atoms and at least one of N, O, and S as a hetero atom, more preferably a heteroaryl group having 3 to 20 carbon atoms and at least one of N, O, and S as a hetero atom, and particularly preferably a carbazolyl group, a group formed by removing any one hydrogen atom from dibenzofuran, and a group formed by removing any one hydrogen atom, a group formed by removing any one hydrogen atom from dibenzothiophene.

The di-substituted amino group as preferred $R^1$ to $R^8$ is preferably a diarylamino group, and more preferably a substituted or unsubstituted diphenylamino group.

The substitution position of an aryl group having 5 to 30 carbon atoms, a heteroaryl group having 3 to 30 carbon atoms, or a di-substituted amino group is preferably any of the positions of $R^1$ to $R^8$, but in the organic electroluminescent element of the present invention, at least one of $R^4$ and $R^6$ in the compound represented by in the general formula (I) is preferably an aryl group having 5 to 30 carbon atoms, a heteroaryl group having 3 to 30 carbon atoms, or a di-substituted amino group. Further, in the organic electroluminescent element of the present invention, $R^4$ and $R^6$ in the compound represented by in the general formula (I) are more preferably each independently an aryl group having 6 to 30 carbon atoms or a di-substituted amino group.

On the other hand, the groups other than $R^4$ and $R^6$ out of $R^1$ to $R^8$ are not particularly limited, but in the organic electroluminescent element of the present invention, $R^1$, $R^2$, $R^3$, $R^5$, $R^7$ and $R^8$ in the compound represented by in the general formula (I) are preferably each a hydrogen atom.

The compound represented by the general formula (I) is preferably a compound represented by a compound represented by the following general formula (II).

pressed by decreasing the decomposition time. Here, since a material having a high sublimation temperature can undergo thermal decomposition during long-term decomposition, it is favorable that the sublimation temperature be not too high from the viewpoint of decomposition suitability. The sublimation temperature (which means a temperature which leads to reduction in 10% by mass in the present specification) of the compound represented by the general formula (I) is preferably 300° C., more preferably 285° C. or lower, and still more preferably 270° C. or lower.

The molecular weight of the compound represented by the general formula (I) is preferably 510 or more, from the viewpoint that the decomposition rate can be easily regulated.

The molecular weight of the compound represented by the general formula (I) is preferably 840 or less, from the viewpoint the sublimation temperature is suitably lowered and decomposition may be induced while not causing the thermal decomposition.

Specific examples of the compound represented by the general formula (I) are shown below, but it should not be construed that the compound represented by the general formula (I) which can be used in the present invention is limited to the specific examples.

[Chem. 5]

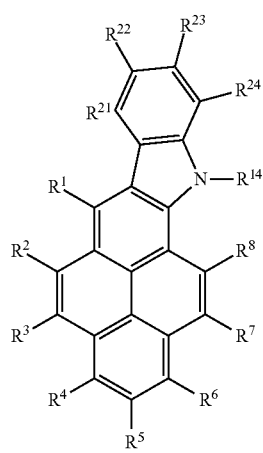

General formula (II)

(In the general formula (II), $R^1$ to $R^8$ and $R^{21}$ to $R^{24}$ represent a hydrogen atom or a substituent. However, there is no case where adjacent substituents selected from $R^1$ to $R^8$, $R^{21}$ to $R^{24}$ are bonded to each other to form a ring. $R^{14}$ represents an alkyl group, an aryl group, or a heteroaryl group.)

In the general formula (II), the preferred ranges shown by the group having the same name as in the general formula (I) are the same as the preferred ranges of the group in the general formula (I).

In the general formula (II), the preferred ranges of $R^{21}$ to $R^{24}$ are the same as the preferred ranges of R in the case where $A^1$, $A^2$, $A^3$ and $A^4$ in general formula (I) represent C—R.

The molecular weight of the compound represented by the general formula (I) is preferably from 300 to 1000, more preferably 450 to 900, and still more preferably 510 to 840. By reducing the molecular weight, the sublimation temperature can be lowered, and thus, it is possible to prevent the thermal deterioration of the compound by decomposition. Further, the energy required for decomposition can be sup-

[Chem. 6]

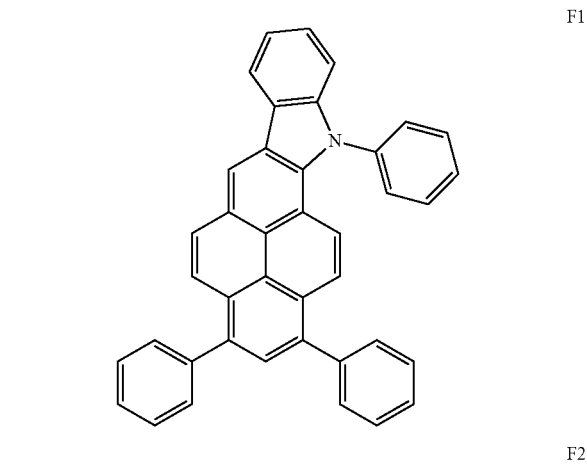

F1

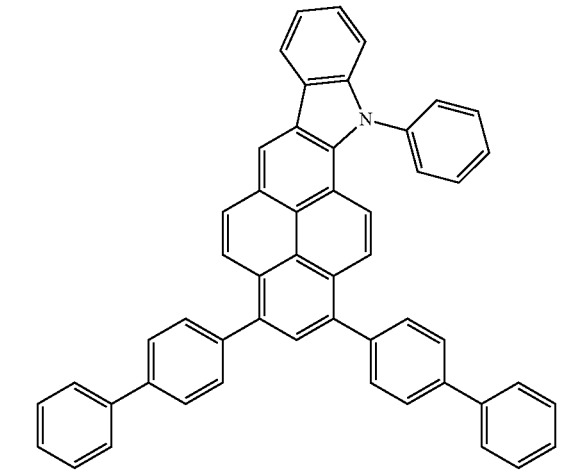

F2

F3
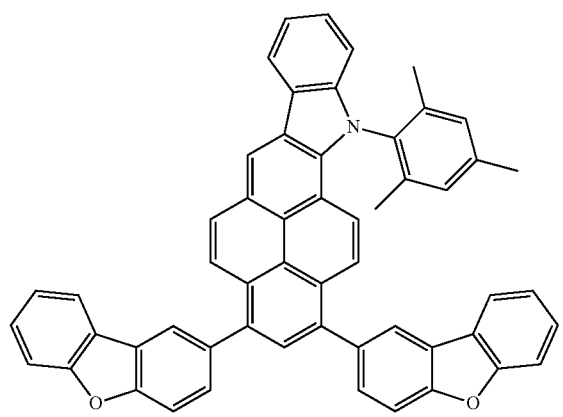
F4
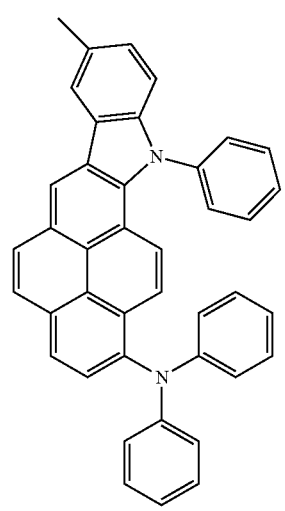
F5
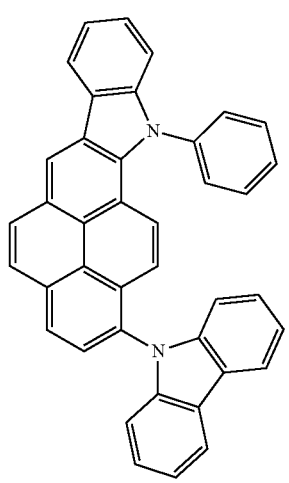
F6
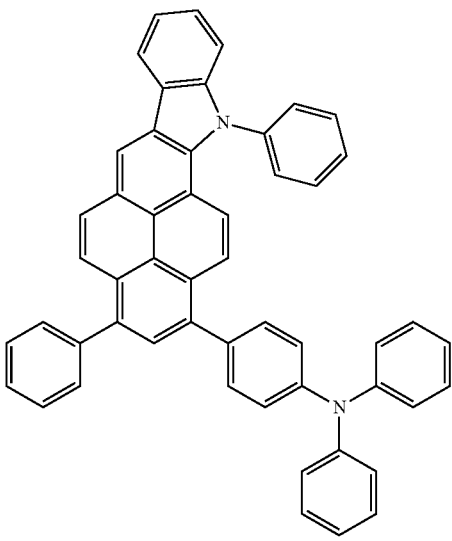
F7
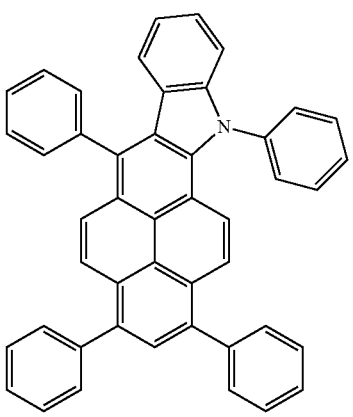
F8
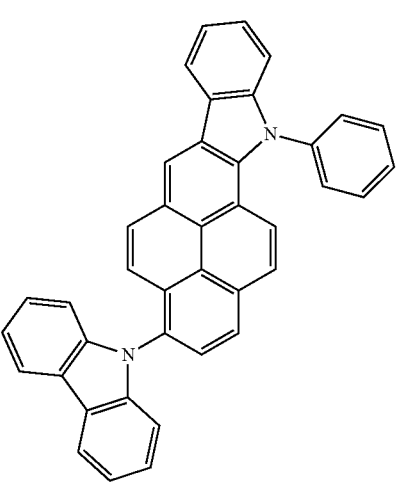

-continued
F9
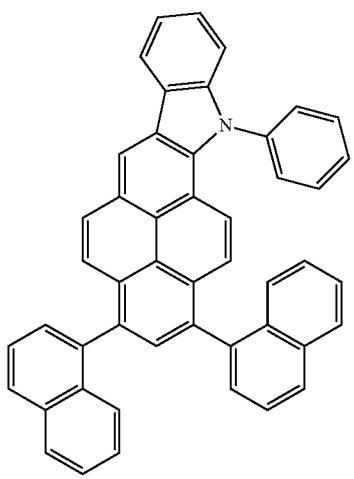
F10
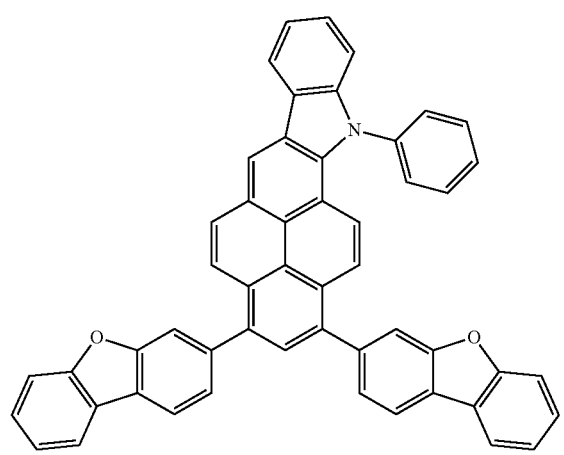
[Chem. 7]
F11
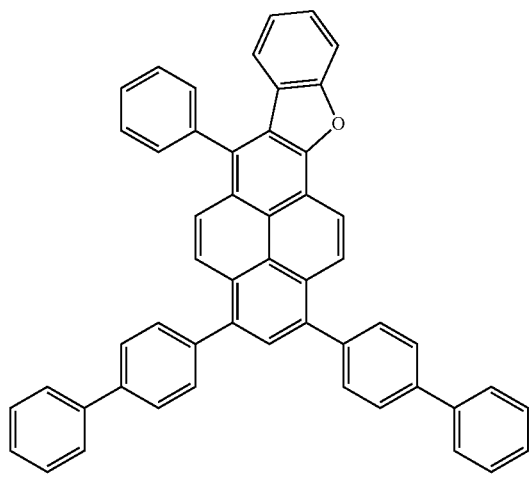
-continued
F12
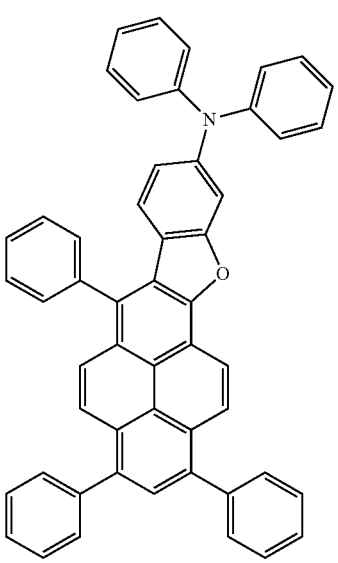
F13
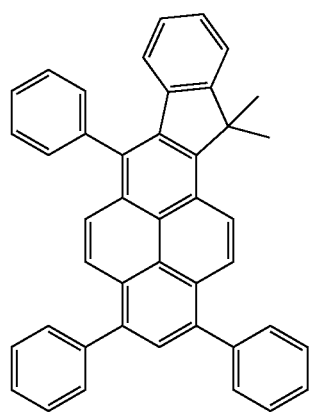
F14
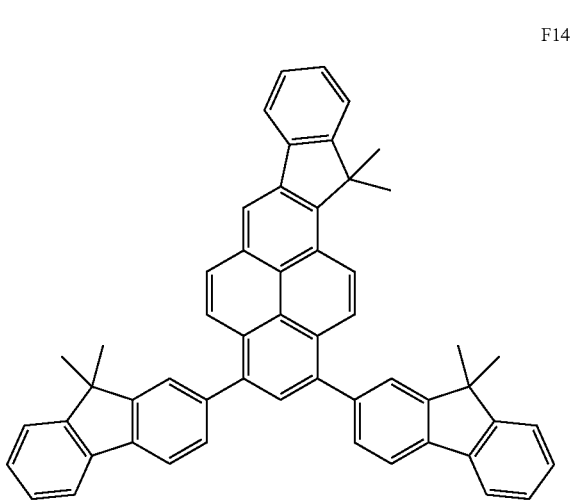

-continued
F15
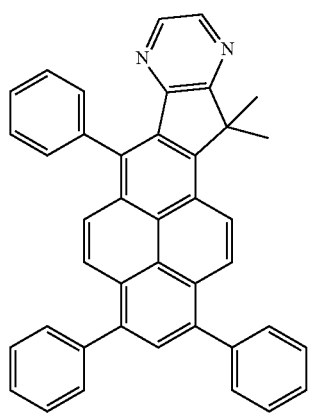
F16
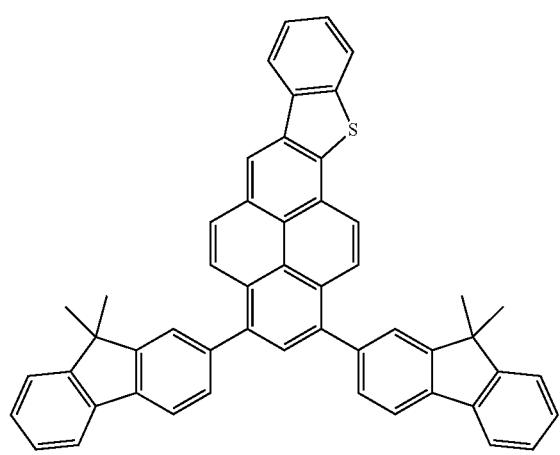
F17
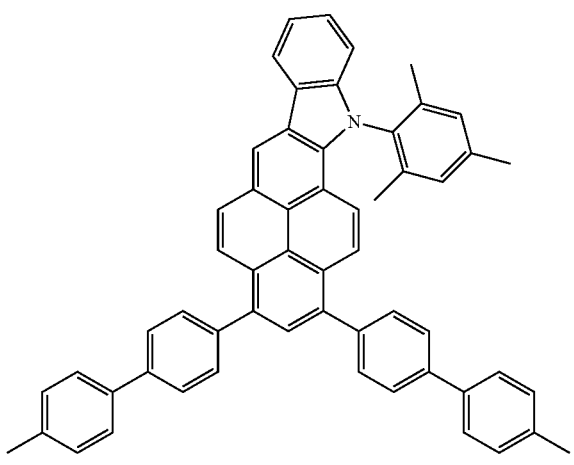
-continued
F18
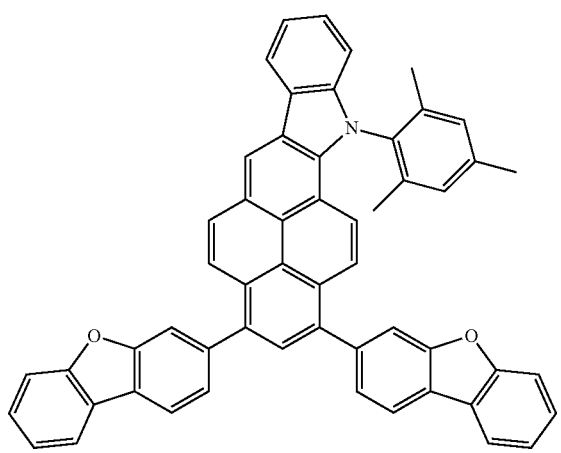
F18
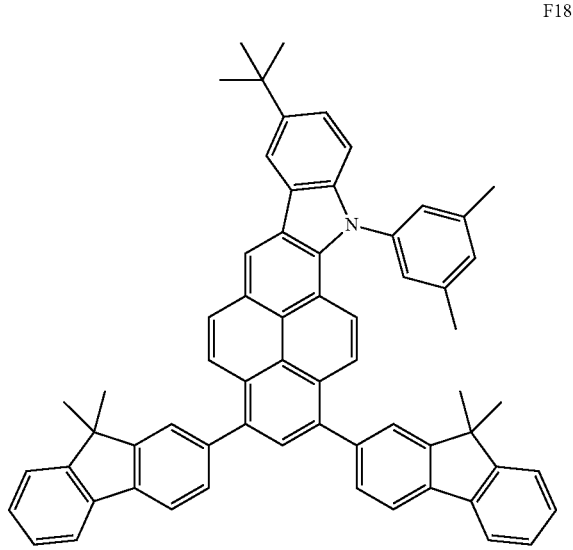 [SMILES: Cc1cc(C)cc(-n2c3ccc(C(C)(C)C)cc3c3cc4ccc5c(-c6ccc7c(c6)C(C)(C)c6ccccc6-7)cc(-c6ccc7c(c6)C(C)(C)c6ccccc6-7)c6ccc(c4c56)c32)c1]
[Chem. 8-1]
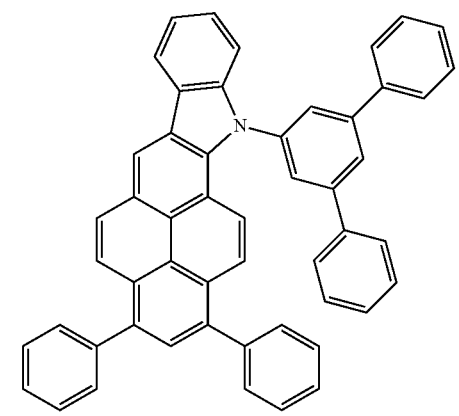

-continued
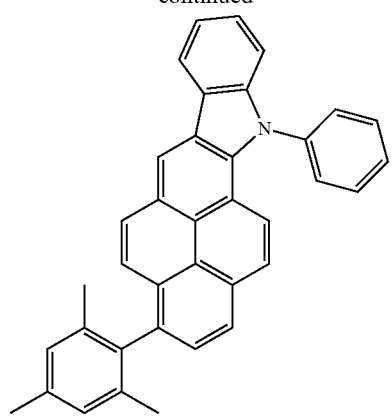
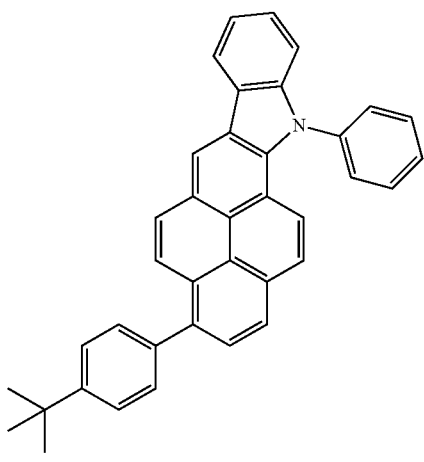
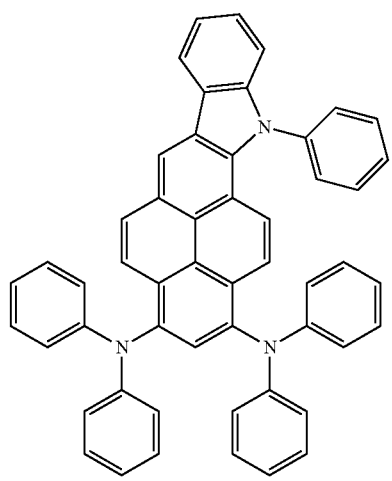
-continued
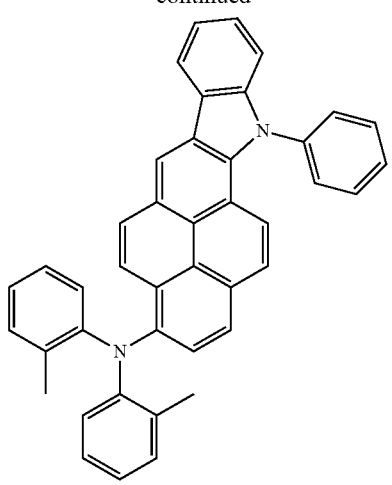
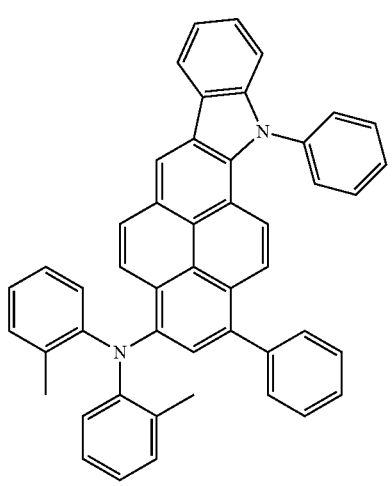
[Chem. 8-2]
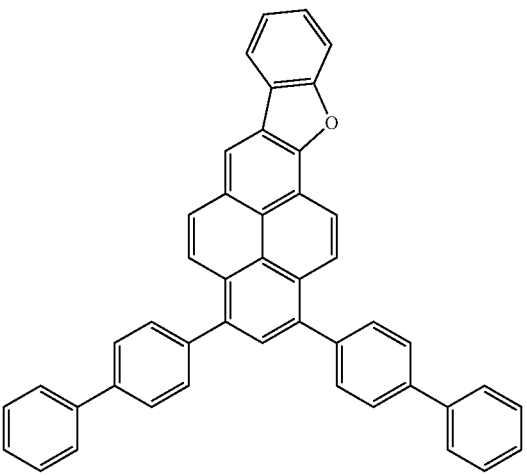

-continued
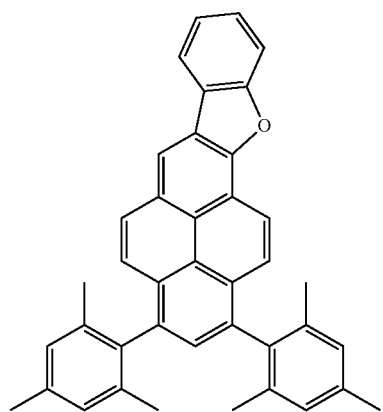
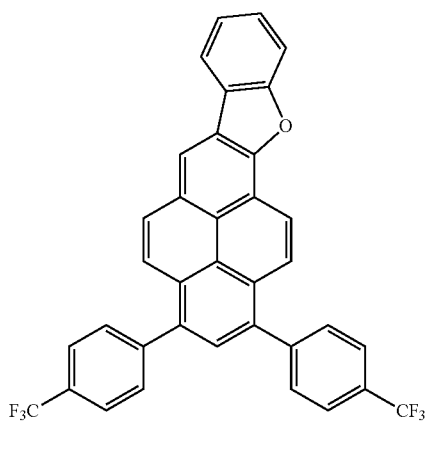
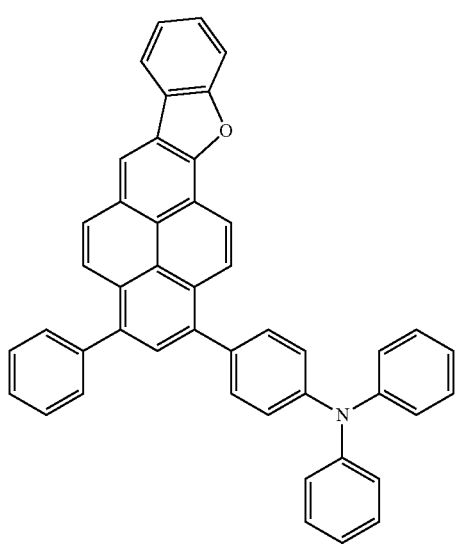
-continued
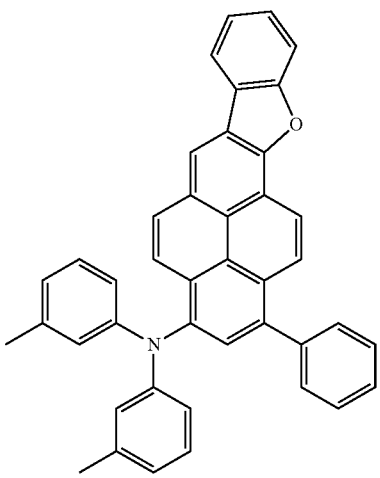
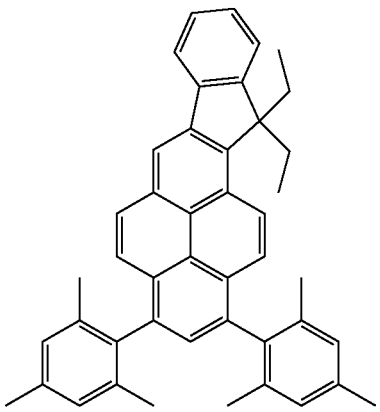
[Chem. 8-3]

23
-continued
24
-continued
[Chem. 8-4]
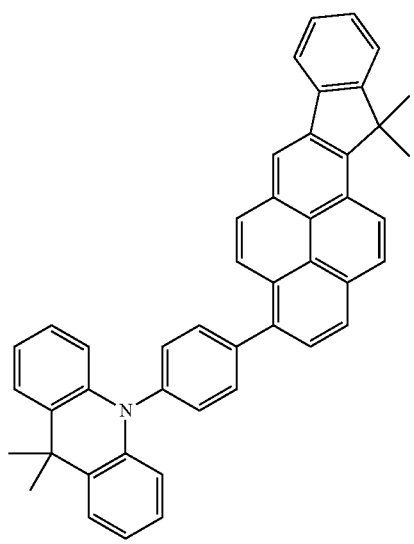
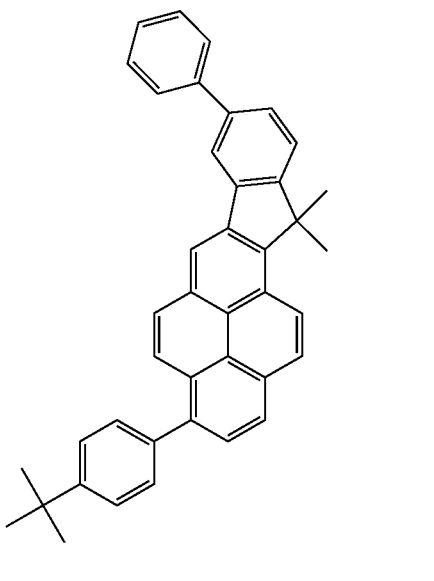
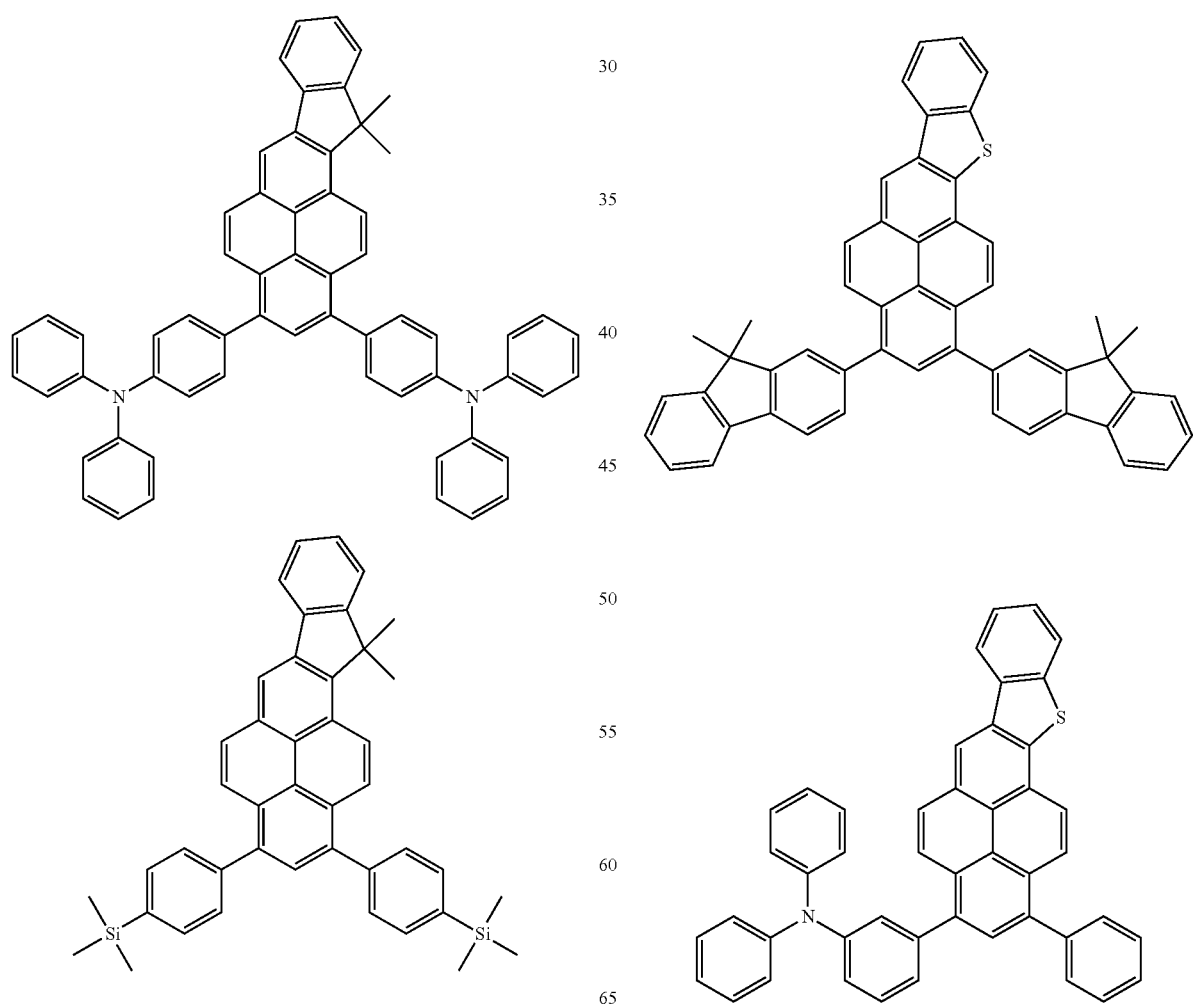

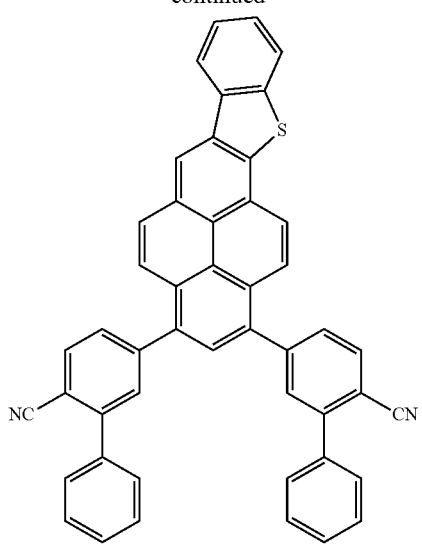

Among these compounds, for example, the compounds F1 and F5 can be preferably used as a host material of a light emitting layer, and a blue light emitting material can be particularly preferably as a host material of a light emitting layer using a light emitting material which emits blue light.

On the other hand, the compounds F1 to F4, and F6 to F19 can be preferably used as a host material of a light emitting layer, and a blue light emitting material can be particularly preferably as a host material of a light emitting layer using a light emitting material which emits blue light. Further, the compound F1 can be preferably used as either of a host material and a light emitting material.

The compound represented by the general formula (I) can be synthesized by the method described in JP-A-2010-111620, US2008/0124455, or the like, or a combination of other known reactions. Further, for example, it can also be synthesized by the following scheme.

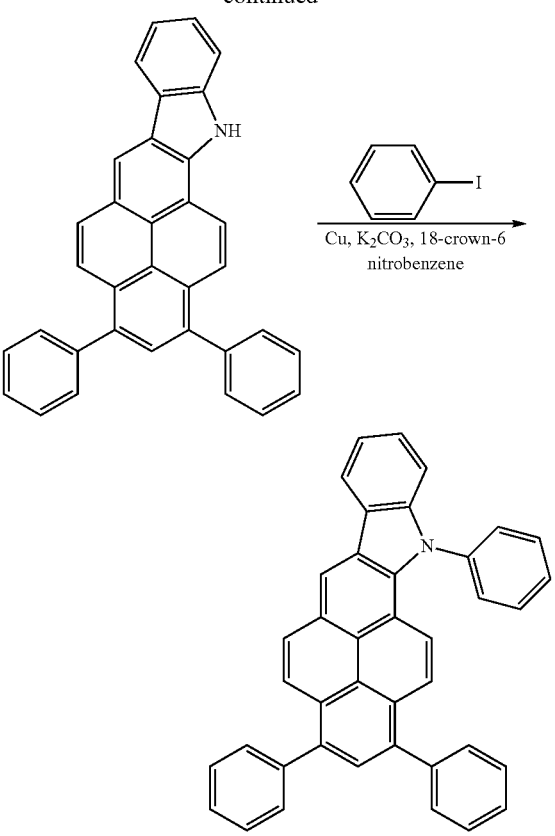

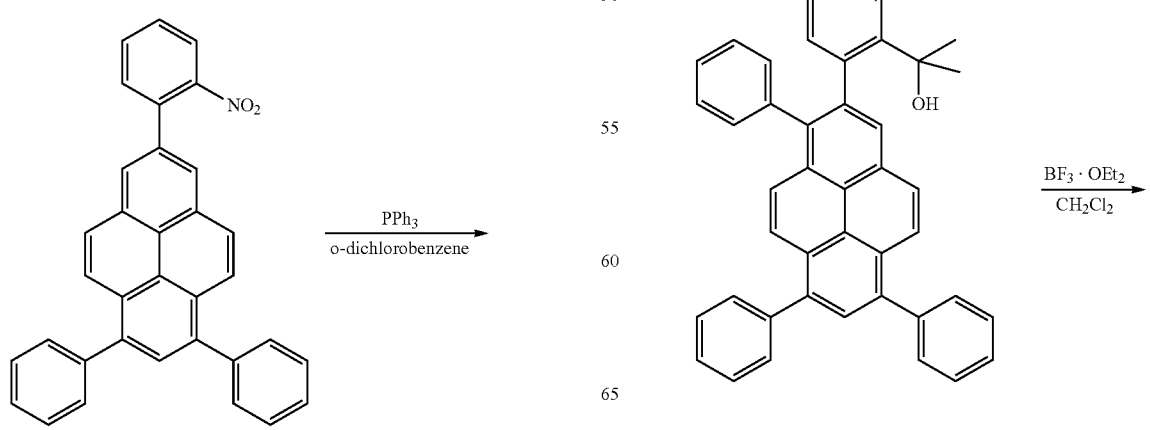

-continued

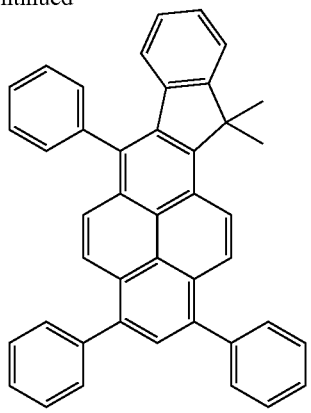

After the synthesis, purification is preferably carried out by column chromatography, recrystallization, or the like, and then by sublimation purification. By the sublimation purification, organic impurities can be separated and inorganic salts, residual solvents, or the like can be removed effectively.

[Organic Electroluminescent Element]

The organic electroluminescent element of the present invention includes a substrate, a pair of electrodes including an anode and a cathode, disposed on the substrate, and at least one organic layer including a light emitting layer, disposed between the electrodes, in which the compound represented by the general formula (I) is contained in any layer of the at least one organic layer.

The configuration of the organic electroluminescent element of the present invention is not particularly limited. FIG. 1 shows one example of the configuration of the organic electroluminescent element of the present invention. The organic electroluminescent element 10 in FIG. 1 has an organic layer between a pair of electrodes (an anode 3 and a cathode 9) on a substrate 2.

The element configuration of the organic electroluminescent element, the substrate, the cathode, and the anode are described in detail in, for example, JP-A-2008-270736, and the detailed descriptions described in this publication can be applied to the present invention.

Hereinafter, preferred aspects of the organic electroluminescent element of the present invention will be described in detail in the order of the substrate, the electrodes, the organic layer, a protective layer, a sealing enclosure, a driving method, a light emitting wavelength, and applications.

<Substrate>

The organic electroluminescent element of the present invention has a substrate.

The substrate used in the present invention is preferably a substrate that does not scatter or decay light emitted from the organic layer. In the case of an organic material, those having excellent heat resistance, dimensional stability, solvent resistance, electrical insulating properties, and processability are preferred.

<Electrodes>

The organic electroluminescent element of the present invention has a pair of electrodes including an anode and a cathode, disposed on the substrate.

In view of the properties of the light emitting element, at least one electrode of a pair of electrodes, the anode and the cathode, is preferably transparent or semi-transparent.

(Anode)

The anode may be usually one having a function as an electrode of supplying holes into an organic layer, and is not particularly limited in terms of its shape, structure, size, or the like. Further, depending on the use and purpose of the light emitting element, the anode can be suitably selected from the known electrode materials. As described above, the anode is usually provided as a transparent anode.

(Cathode)

The cathode may be usually one having a function as an electrode of injecting electrons to an organic layer, and is not particularly limited in terms of its shape, structure, size, or the like. Further, depending on the use and purpose of the light emitting element, the cathode can be suitably selected from the known electrode materials.

<Organic Layer>

The organic electroluminescent element of the present invention has at least one organic layer including a light emitting layer, disposed between the electrodes, in which the compound represented by the general formula (I) is contained in at least one layer of the organic layers. In the organic electroluminescent element of the present invention, at least one organic layer including the compound represented by the general formula (I) is preferably a light emitting layer.

The organic layer is not particularly limited and can be suitably selected depending on the use and purpose of the organic electroluminescent element. However, the organic layer is preferably formed on the transparent electrode or the semi-transparent electrode. In that case, the organic layer is formed on the whole surface or one surface of the transparent electrode or the semi-transparent electrode.

The shape, the size, the thickness, and the like of the organic layer are not particularly limited and can be suitably selected depending on the purpose.

Hereinafter, the configuration of the organic layer, the method for forming an organic layer, preferred aspects of the respective layers constituting the organic layer, and the materials used in the respective layers in the organic electroluminescent element of the present invention will be described in detail in order.

(Configuration of Organic Layer)

In the organic electroluminescent element of the present invention, the organic layer includes a light emitting layer. The organic layer preferably includes a charge transporting layer. The charge transporting layer refers to a layer in which charges move when voltage is applied to the organic electroluminescent element. Specifically, examples thereof include a hole injecting layer, a hole transporting layer, an electron blocking layer, a light emitting layer, a hole blocking layer, an electron transporting layer, and an electron injecting layer. When the charge transporting layer is a hole injecting layer, a hole transporting layer, an electron blocking layer, or a light emitting layer, an organic electroluminescent element can be prepared with low cost and high efficiency.

The compound represented by the general formula (I) is contained in at least one organic layer in the light emitting layer in the organic layers disposed between the electrodes of the organic electroluminescent element, and preferably contained in the light emitting layer in the organic layers disposed between the electrodes.

However, so far as the gist of the present invention is not deviated, the compound represented by the general formula (I) may be contained in an organic layer other than the light emitting layer of the organic electroluminescent element of the present invention. Examples of the organic layer other than the light emitting layer, which may contain the compound represented by the general formula (I), include a hole injecting layer, a hole transporting layer, an electron transporting layer, an electron injecting layer, an exciton blocking layer, and a charge blocking layer (a hole blocking layer, an electron blocking layer, and the like), preferably any one of an exciton blocking layer, a charge blocking layer, an electron transporting layer, and an electron injecting layer, and more preferably an exciton blocking layer, a charge blocking layer, or an electron transporting layer.

In the case where the compound represented by the general formula (I) is contained as a light emitting material in the light emitting layer, the compound represented by the general formula (I) is contained, preferably in the amount of 0.1% by mass to 100% by mass, more preferably 1% by mass to 50% by mass, and still more preferably 2% by mass to 20% by mass, with respect to the total mass of the light emitting layer.

In the case where the compound represented by the general formula (I) is contained in the light emitting layer as a host material, the compound represented by the general formula (I) is contained, preferably in the amount of 10% by mass to 99.9% by mass, more preferably 50% by mass to 99% by mass, and still more preferably 80% by mass to 98% by mass, with respect to the total mass of in the light emitting layer.

In the case where the compound represented by the general formula (I) is contained in an organic layer other than the light emitting layer, the compound represented by the general formula (I) is contained in the organic layer, preferably in the amount of 70% by mass to 100% by mass, more preferably 80% by mass to 100% by mass, and still more preferably 90% by mass to 100% by mass, with respect to the total mass of the organic layers.

(Method for Forming Organic Layer)

The respective organic layers in the organic electroluminescent element of the present invention can be suitably formed by any of dry film forming methods such as a deposition method and a sputtering method, and wet type film forming methods (solution coating methods) such as a transfer method, a printing method, a spin coating method, and a bar coating method.

In the organic electroluminescent element of the present invention, it is preferable that the organic layers disposed between the pair of electrodes be formed by deposition of a composition further including at least the compound represented by the general formula (I) on at least one layer.

(Light Emitting Layer)

The light emitting layer is a layer having a function of, upon application of an electric field, receiving holes from the anode, the hole injecting layer, or the hole transporting layer, receiving electrons from the cathode, the electron injecting layer, or the electron transporting layer, providing a recombination site of the holes and the electrons, and causing light emitting. However, the light emitting layer in the present invention is not necessarily limited to the light emitting by such a mechanism.

The light emitting layer in the organic electroluminescent element of the present invention may be constituted of only the light emitting material, or may be constituted as a mixed layer of a host material and the light emitting material. The light emitting material may be made of a single kind or two or more kinds thereof. The host material is preferably a charge transporting material. The host material may be made of a single kind or two or more kinds thereof. Examples thereof include a configuration in which an electron transporting host material and a hole transporting host material are mixed. Further, the light emitting layer may include a material which does not have charge transporting properties and does not emit light.

In addition, the light emitting layer may be made of a single layer or multiple layers of two or more layers. The respective layers may include the same light emitting material or host material, and may also include a different material in every layer. In the case where a plurality of light emitting layers are present, the respective light emitting layers may emit light in a different luminous color from each other.

The thickness of the light emitting layer is not particularly limited, but it is usually from 2 nm to 500 nm, and above all, from the viewpoint of external quantum efficiency, it is more preferably from 3 nm to 200 nm, and still more preferably from 5 nm to 100 nm.

In the organic electroluminescent element of the present invention, in a more preferred aspect, the light emitting layer contains the compound represented by the general formula (I), and the compound represented by the general formula (I) is used as the light emitting material of the light emitting layer. Here, the host material as referred to in the present specification is a compound which chiefly plays a role in injecting or transporting charges in the light emitting layer and is also a compound which does not substantially emit light in itself. As used herein, the statement "which does not substantially emit light" means that the amount of light emission from the compound which does not substantially emit light is preferably 5% or less, more preferably 3% or less, and still more preferably 1% or less, with respect to the total amount of light emission in the entirety of the element.

On the other hand, the compound represented by the general formula (I) may be used a host material of the light emitting layer as described above.

(Light Emitting Material)

In the organic electroluminescent element of the present invention, the compound represented by the general formula (I) is used as the light emitting material, but in this case, a combination of the compound with light emitting materials different from the compound represented by the general formula (I) can be used. Further, in the organic electroluminescent element of the present invention, in the case where the compound represented by the general formula (I) is used as a host material of the light emitting layer or in the case where the compound represented by the general formula (I) is used in an organic layer other than the light emitting layer, the light emitting materials different from the compound represented by the general formula (I) are used in the light emitting layer.

The light emitting material which can be used in the present invention may be any of a phosphorescent light emitting material and a fluorescent light emitting material. Further, the light emitting layer in the present invention may contain two or more kinds of light emitting materials in order to improve the color purity or widen the light emitting wavelength region.

The fluorescent light emitting material and the phosphorescent light emitting material which can be used in the organic electroluminescent element of the present invention are described in detail in, for example, paragraph Nos. [0100] to [0164] of JP-A-2008-270736 and paragraph Nos. [0088] to [0090] of JP-A-2007-266458, the detailed descriptions thereon in these publications can be applied to the present invention.

Examples of the phosphorescent light emitting material which can be used in the present invention include phosphorescent light emitting materials described in patent documents, for example, U.S. Pat. No. 6,303,238, U.S. Pat. No. 6,097,147, WO00/57676, WO00/70655, WO01/08230, WO01/39234, WO01/41512, WO02/02714, WO02/15645, WO02/44189, WO05/19373, JP-A-2001-247859, JP-A-2002-302671, JP-A-2002-117978, JP-A-2003-133074, JP-A-2002-235076, JP-A-2003-123982, JP-A-2002-170684, EP1211257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259. Above all, examples of the light emitting material which is more preferred include phosphorescent light emitting metal complex compounds such as Ir complexes, Pt complexes, Cu complexes, Re complexes, W complexes, Rh complexes, Ru complexes, Pd complexes, Os complexes, Eu complexes, Tb complexes, Gd complexes, Dy complexes, and Ce complexes, with Ir complexes, Pt complexes, and Re complexes being particularly preferred. Above all, Ir complexes, Pt complexes, and Re complexes each including at least one coordination mode of a metal-carbon bond, a metal-nitrogen bond, a metal-oxygen bond, and a metal-sulfur bond are preferred. Furthermore, from the viewpoints of luminous efficiency, driving durability, and chromaticity, Ir complexes and Pt complexes are particularly preferred, and Ir complexes are the most preferred.

The kind of the fluorescent light emitting material which can be used in the present invention is not particularly limited, but examples thereof include those other than the compound represented by the general formula (I), for example, benzoxazole, benzimidazole, benzothiazole, styrylbenzene, polyphenyl, diphenylbutadiene, tetraphenylbutadiene, naphthalimide, coumarin, pyrane, perinone, oxadiazole, aldazine, pyralizine, cyclopentadiene, bisstyrylanthracene, quinacridone, pyrrolopyridine, thiadiazolopyridine, cyclopentadiene, styrylamine, aromatic fused polycyclic compounds (anthracene, phenanthroline, pyrene, perylene, rubrene, pentacene, and the like), a variety of metal complexes typified by metal complexes of 8-quinolinol, pyrromethene complexes, and rare-earth complexes, polymer compounds such as polythiophene, polyphenylene, and polyphenylenevinylene, organic silanes, and derivatives thereof.

In addition, the compound described in [0082] of JP-A-2010-111620 can also be used as a light emitting material.

The light emitting layer in the organic electroluminescent element of the present invention may be constituted with only a light emitting material or may be constituted as a mixed layer of a host material and a light emitting material. The light emitting material may be made of a single kind or two or more kinds. The host material is preferably a charge transport material. The host material may be made of a single kind or two or more kinds. Examples thereof include a configuration in which an electron-transporting host material and a hole-transporting host material are mixed. Furthermore, the light emitting layer may contain a material which does not have charge transporting properties and which does not emit light.

In addition, the light emitting layer may be made of a single layer or two or more layers. The respective layers may include the same light emitting materials or host materials, and may also include different materials from each other over layers. In the case where a plurality of light emitting layers are present, the respective light emitting layers may emit light in different luminous colors from each other.

(Host Material)

The host material is a compound that usually plays a role in injecting or transporting charges in the light emitting layer and is also a compound which does not substantially emit light in itself. As used herein, it is meant by the terms "which does not substantially emit light" that the amount of light emitting from the compound which does not substantially emit light is preferably 5% or less, more preferably 3% or less, and still more preferably 1% or less of the total amount of light emitting in the whole of the element.

Examples of the host material which can be used in the organic electroluminescent element of the present invention include the following compounds, other than compound represented by the general formula (I):

conductive high-molecular oligomers such as pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkanes, pyrazoline, pyrazolone, phenylenediamine, arylamines, amino-substituted chalcone, styrylanthracene, fluorenone, hydrazone, stilbene, silazane, aromatic tertiary amine compounds, styrylamine compounds, porphyrin-based compounds, fused ring aromatic hydrocarbon compounds (fluorene, naphthalene, phenanthrene, triphenylene, and the like), polysilane-based compounds, poly(N-vinylcarbazole), aniline-based copolymers, thiophene oligomers, and polythiophene, organic silanes, carbon films, pyridine, pyrimidine, triazine, imidazole, pyrazole, triazole, oxazole, oxadiazole, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic anhydrides such as naphthalene perylene, phthalocyanine, and a variety of metal complexes typified by metal complexes of 8-quinolinol derivatives and metal complexes having metal phthalocyanine, benzoxazole, or benzothiazole as a ligand thereof, and derivatives thereof (which may have a substituent or a fused ring). In addition, the compounds described in [0081] or [0083] of JP-A-2010-111620 can also be used.

Above all, carbazole, dibenzothiophene, dibenzofuran, arylamine, aromatic hydrocarbon compounds with fused rings, and metal complexes are preferred, and aromatic hydrocarbon compounds with fused rings are particularly preferred since they are stable. As the aromatic hydrocarbon compounds with fused rings, naphthalene-based compounds, anthracene-based compounds, phenanthrene-based compounds, triphenylene-based compounds, and pyrene-based compounds are preferred; anthracene-based compounds and pyrene-based compounds are more preferred; and anthracene-based compounds are particularly preferred. As the anthracene-based compounds, those described in [0033] to [0064] of WO 2010/134350 are particularly preferred, and examples thereof include Compounds H-1 and H-2 as described later.

The host material that can be used in the light emitting layer in the organic electroluminescent element of the present invention may be a host material having hole transporting properties or a host material having electron transporting properties.

Furthermore, the content of the host compound in the light emitting layer in the organic electroluminescent element of the present invention is not particularly limited, but from the viewpoint of luminous efficiency and driving voltage, it is preferably from 15% by mass to 95% by mass, with respect to the total mass of the compounds forming the light emitting layer. When the light emitting layer includes a plurality of kinds of host compounds containing the compound represented by the general formula (I), the content of the compound represented by the general formula (I) is preferably from 50% by mass to 99% by mass, with respect to the total host compounds.

(Other Layers)

The organic electroluminescent element of the present invention may include layers other than the light emitting layer.

Examples of the organic layer other than the light emitting layer which may be included in the organic layer include a hole injecting layer, a hole transporting layer, a blocking layer (a hole blocking layer, an exciton blocking layer, and the like), and an electron transporting layer. Specifically, examples of the layer configuration include those described below, but it should not be construed that the present invention is limited to these configurations.

Anode/hole transporting layer/light emitting layer/electron transporting layer/cathode, Anode/hole transporting layer/light emitting layer/blocking layer/electron transporting layer/cathode, Anode/hole transporting layer/light emitting layer/blocking layer/electron transporting layer/electron injecting layer/cathode, Anode/hole injecting layer/hole transporting layer/light emitting layer/blocking layer/electron transporting layer/cathode, Anode/hole injecting layer/hole transporting layer/light emitting layer/electron transporting layer/electron injecting layer/cathode, Anode/hole injecting layer/hole transporting layer/light emitting layer/blocking layer/electron transporting layer/electron injecting layer/cathode, Anode/hole injecting layer/hole transporting layer/blocking layer/light emitting layer/blocking layer/electron transporting layer/electron injecting layer/cathode.

The organic electroluminescent element of the present invention preferably includes at least one organic layer which is preferably disposed between the (A) anode and the light emitting layer. Examples of the organic layer which is preferably disposed between the (A) anode and the light emitting layer include an hole injecting layer, a hole transporting layer, and an electron blocking layer from the anode side.

The organic electroluminescent element of the present invention preferably includes at least one organic layer which is preferably disposed between the (B) cathode and the light emitting layer. Examples of the organic layer which is preferably disposed between the (B) cathode and the light emitting layer include an electron injecting layer, an electron transporting layer, and a hole blocking layer from the cathode side.

Specifically, an example of the preferred aspects of the organic electroluminescent element of the present invention is the aspect shown in FIG. 1, in which a hole injecting layer 4, a hole transporting layer 5, a light emitting layer 6, a hole blocking layer 7, and an electron transporting layer 8 are laminated in this order as the organic layer from the anode 3 side.

Hereinafter, the layers other than the light emitting layer which the organic electroluminescent element of the present invention may have will be described.

(A) Organic Layer Preferably Disposed Between Anode and Light Emitting Layer:

First, the (A) organic layer preferably disposed between the anode and the light emitting layer will be described.

(A-1) Hole Injecting Layer and Hole Transporting Layer

The hole injecting layer and the hole transporting layer are layers having a function of receiving holes from the anode or the anode side and transporting them to the cathode side.

The light emitting element of the present invention preferably includes at least one organic layer between the light emitting layer and the anode, and the organic layer preferably includes at least one compound of the compounds represented by the following general formulae (Sa-1), (Sb-1), and (Sc-1).

[Chem. 10]

General formula (Sa-1)

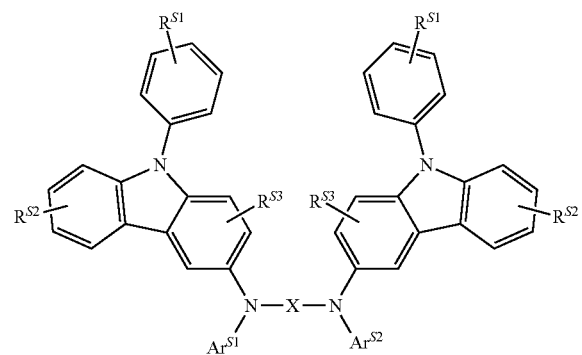

(in which X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms.)

[Chem. 11]

General formula (Sb-1)

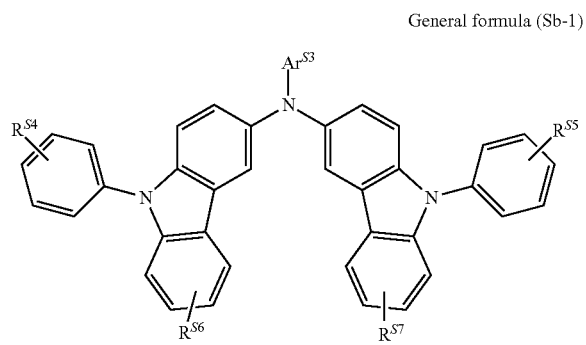

(in which $R^{S4}$, $R^{S5}$, $R^{S6}$, and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$, and $R^{S7}$ may be bonded to each other to form a saturated carbocycle or an unsaturated carbocycle. $Ar^{S3}$ represents a substituted or unsubstituted aryl group having 6 to 30 carbon atoms, or a substituted or unsubstituted heteroaryl group having 2 to 30 carbon atoms.)

[Chem. 12]

General formula (Sc-1)

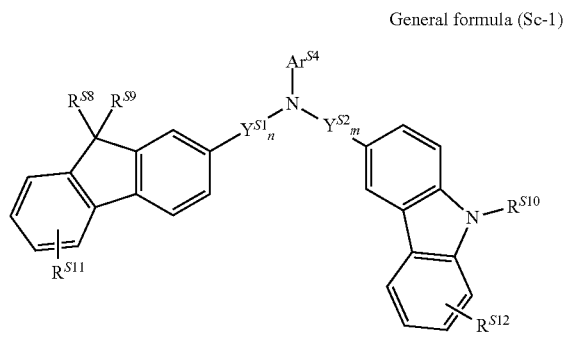

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ each independently represent a substituted or unsubstituted alkylene group having 1 to 30 carbon atoms, or a substituted or unsubstituted arylene group having 6 to 30 carbon atoms. n and m each independently represent an integer of 0 to 5.)

The general formula (Sa-1) will be described.

In the general formula (Sa-1), X represents a substituted or unsubstituted alkylene group having 1 to 30 carbon atoms, a substituted or unsubstituted alkenylene group having 2 to 30 carbon atoms, a substituted or unsubstituted arylene group having 6 to 30 carbon atoms, a substituted or unsubstituted heteroarylene group having 2 to 30 carbon atoms, or a substituted or unsubstituted heterocycle having 2 to 30 carbon atoms. X is preferably a substituted or unsubstituted arylene group having 6 to 30 carbon atoms, more preferably having a substituted or unsubstituted phenylene, a substituted or unsubstituted biphenylene, and a substituted or unsubstituted naphthylene, and still more preferably a substituted or unsubstituted biphenylene.

$R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S1}$, $R^{S2}$, and $R^{S3}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S1}$ and $Ar^{S2}$ each independently represent a substituted or unsubstituted aryl group having 6 to 30 carbon atoms, or a substituted or unsubstituted heteroaryl group having 2 to 30 carbon atoms. $Ar^{S1}$ and $Ar^{S2}$ are preferably a substituted or unsubstituted phenyl group.

Next, the general formula (Sb-1) will be described.

In the general formula (Sb-1), $R^{S4}$, $R^{R5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S4}$, $R^{S5}$, $R^{S6}$ and $R^{S7}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom.

$Ar^{S3}$ represents a substituted or unsubstituted aryl group having 6 to 30 carbon atoms, or a substituted or unsubstituted heteroaryl group having 2 to 30 carbon atoms. $Ar^{S3}$ is preferably a substituted or unsubstituted phenyl group.

Next, the general formula (Sc-1) will be described.

In the general formula (Sc-1), $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S8}$ and $R^{S9}$ are preferably a substituted or unsubstituted alkyl group having 1 to 30 carbon atoms, or a substituted or unsubstituted aryl group having 6 to 30 carbon atoms, and more preferably a methyl group or a phenyl group. $R^{S10}$ is a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ is preferably a substituted or unsubstituted aryl group having 6 to 30 carbon atoms, and more preferably a phenyl group. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. Examples of the saturated carbocycle or the unsaturated carbocycle include naphthalene, azulene, anthracene, fluorene, and phenalene. $R^{S11}$ and $R^{S12}$ are preferably a hydrogen atom, a substituted or unsubstituted alkyl group having 1 to 30 carbon atoms, a substituted or unsubstituted aryl group having 6 to 30 carbon atoms, a substituted or unsubstituted fused polycyclic group having 5 to 30 carbon atoms, or a cyano group, and more preferably a hydrogen atom. $Ar^{S4}$ represents a substituted or unsubstituted aryl group having 6 to 30 carbon atoms, or a substituted or unsubstituted heteroaryl group having 2 to 30 carbon atoms. $Y^{S1}$ and $Y^{S2}$ represent a substituted or unsubstituted alkylene having 1 to 30 carbon atoms, or substituted or unsubstituted arylene having 6 to 30 carbon atoms. $Y^{S1}$ and $Y^{S2}$ are preferably a substituted or unsubstituted arylene having 6 to 30 carbon atoms, and more preferably a substituted or unsubstituted phenylene. n is an integer of 0 to 5, preferably 0 to 3, more preferably 0 to 2, and still more preferably 0. m is an integer of 0 to 5, preferably 0 to 3, more preferably 0 to 2, and still more preferably 1.

The general formula (Sa-1) is preferably a compound represented by the following general formula (Sa-2).

[Chem. 13]

General formula (Sa-2)

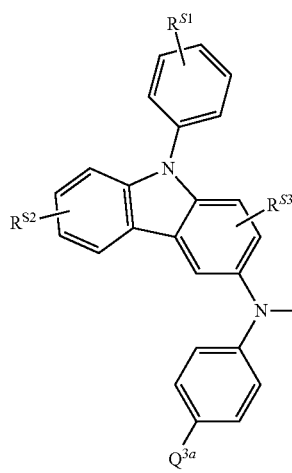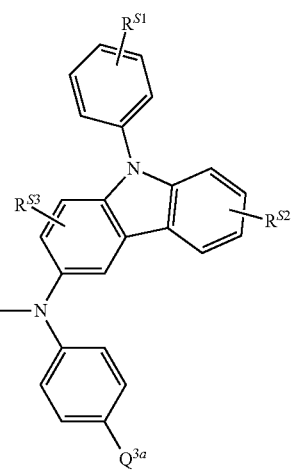

(in which $R^{S1}$, $R^{S2}$, and $R^{S3}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S1}$, $R^{S2}$, and $R^{S3}$ may be bonded to each other to form a saturated carbocycle or an unsaturated carbocycle. $Q^{Sa}$ each independently represent a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sa-2) will be described. $R^{S1}$, $R^{S2}$, and $R^{S3}$ have the same definitions as those in the general formula (Sa-1), and their preferred ranges are also the same. Each $Q^{Sa}$ independently represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom or a substituted or unsubstituted alkyl group having 1 to 30 carbon atoms, and still more preferably a hydrogen atom.

The general formula (Sb-1) is preferably a compound represented by the following general formula (Sb-2).

[Chem. 14]

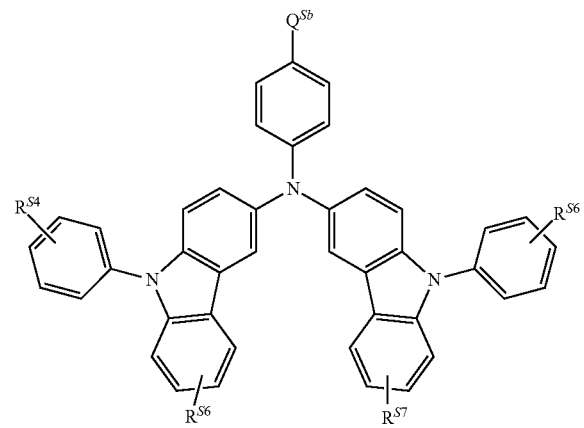

General formula (Sb-2)

(in which $R^{S4}$, $R^{S5}$, $R^{S6}$ and $R^{S7}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, a substituted or unsubstituted fused polycyclic group having 5 to 30 carbon atoms, a hydroxy group, a cyano group, or a substituted or unsubstituted amino group. Adjacent $R^{S4}$, $R^{S5}$, $R^{S6}$ and $R^{S7}$ may be bonded to each other to form a saturated carbocycle or an unsaturated carbocycle. $Q^{Sb}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sb-2) will be described. $R^{S4}$, $R^{S5}$, $R^{S6}$ and $R^{S7}$ have the same definitions as those in the general formula (Sb-1), and their preferred ranges are also the same. $Q^{Sa}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sa}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted alkyl group having 1 to 30 carbon atoms, and still more preferably a hydrogen atom.

The general formula (Sc-1) is preferably a compound represented by the following general formula (Sc-2).

[Chem. 15]

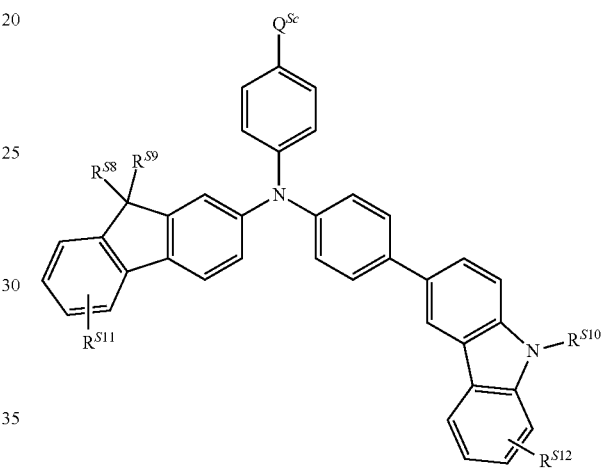

General formula (Sc-2)

(in which $R^{S8}$ and $R^{S9}$ each independently represent a hydrogen atom, a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S10}$ represents a substituted or unsubstituted alkyl group having 1 to 30 carbon atoms, a substituted or unsubstituted aryl group having 6 to 30 carbon atoms, a substituted or unsubstituted heterocyclic group having 2 to 30 carbon atoms, or a substituted or unsubstituted fused polycyclic group having 5 to 30 carbon atoms. $R^{S11}$ and $R^{S12}$ each independently represent a hydrogen atom, a substituted or unsubstituted alkyl group having 1 to 30 carbon atoms, a substituted or unsubstituted alkoxy group having 1 to 30 carbon atoms, a substituted or unsubstituted aryl group having 6 to 30 carbon atoms, a substituted or unsubstituted aryloxy group having 6 to 30 carbon atoms, a substituted or unsubstituted heterocycle having 2 to 30 carbon atoms, or a substituted or unsubstituted fused polycyclic group having 5 to 30 carbon atoms, a hydroxy group, a cyano group, or a substituted or unsubstituted amino group. Adjacent $R^{S11}$ and $R^{S12}$ may be bonded to each other to form a saturated carbocycle or an unsaturated carbocycle. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group.)

The general formula (Sc-2) will be described. $R^{S8}$, $R^{S9}$, $R^{S10}$, $R^{S11}$ and $R^{S12}$ have the same definitions as those in the general formula (Sc-1), and their preferred ranges are also the same. $Q^{Sc}$ represents a hydrogen atom, a cyano group, a fluorine atom, an alkoxy group having 1 to 30 carbon atoms, a substituted or unsubstituted alkyl group having 1 to 30 carbon atoms, an aryloxy group having 6 to 30 carbon atoms, a substituted or unsubstituted aryl group having 6 to 30 carbon atoms, a substituted or unsubstituted heterocycle having 2 to 30 carbon atoms, or a substituted or unsubstituted amino group. $Q^{Sc}$ is preferably a hydrogen atom, a cyano group, a fluorine atom, a substituted or unsubstituted alkyl group having 1 to 30 carbon atoms, or a substituted or unsubstituted aryl group having 6 to 30 carbon atoms, more preferably having a hydrogen atom, or a substituted or unsubstituted aryl group having 6 to 30 carbon atoms, and still more preferably a phenyl group.

Specific examples of the compounds represented by the general formulae (Sa-1), (Sb-1), and (Sc-1) include the following ones. However, the present invention is not limited to the following specific examples.

[Chem. 16]

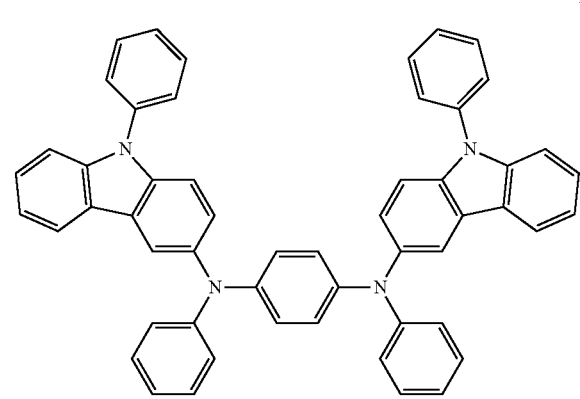

1

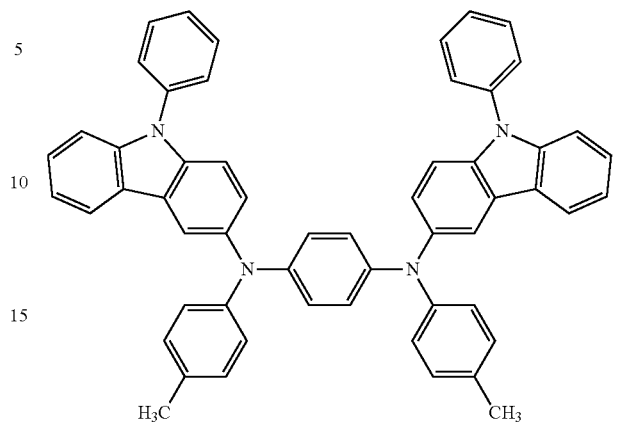

3

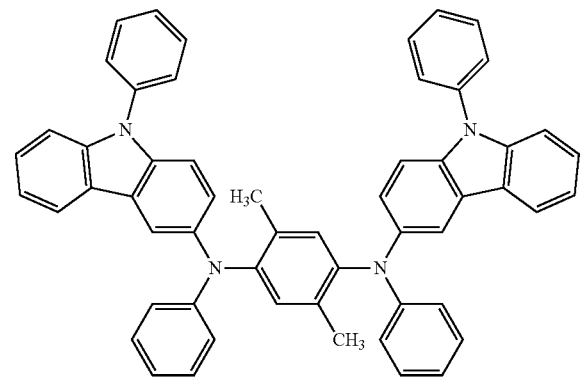

2

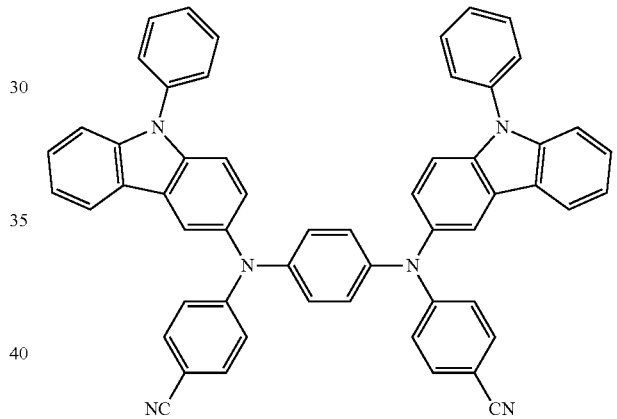

4

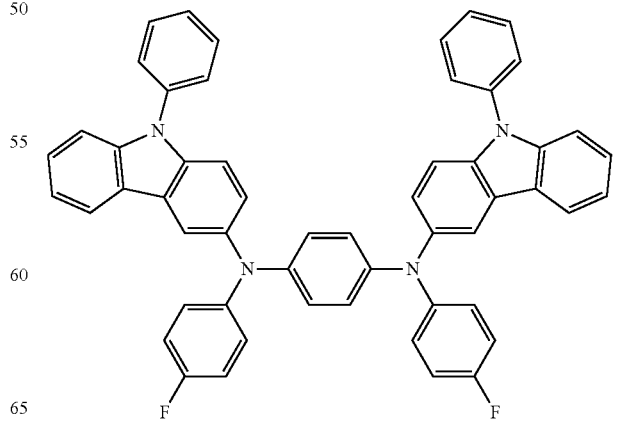

5

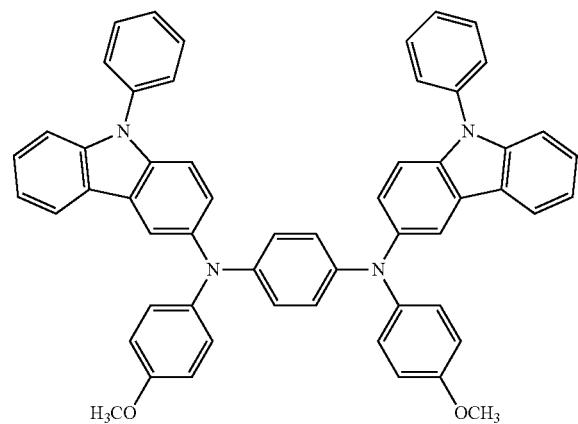
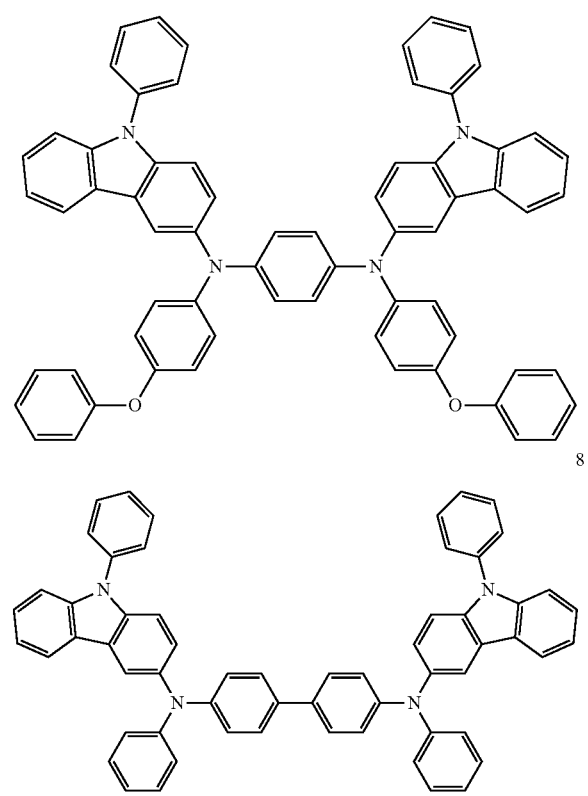
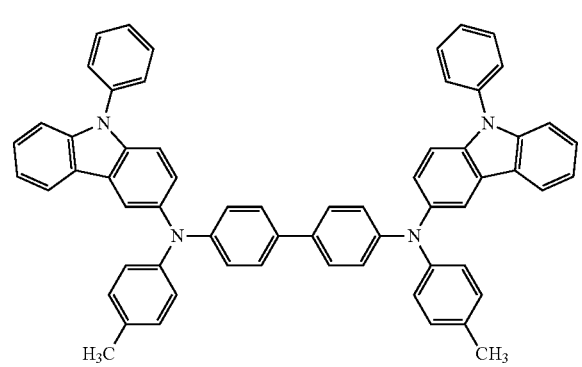
[Chem. 17]

14
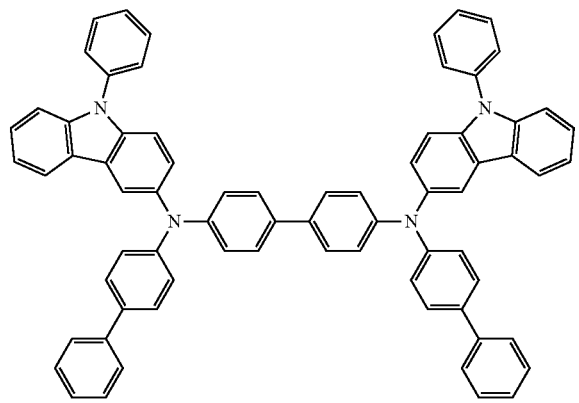
[Chem. 18]
15
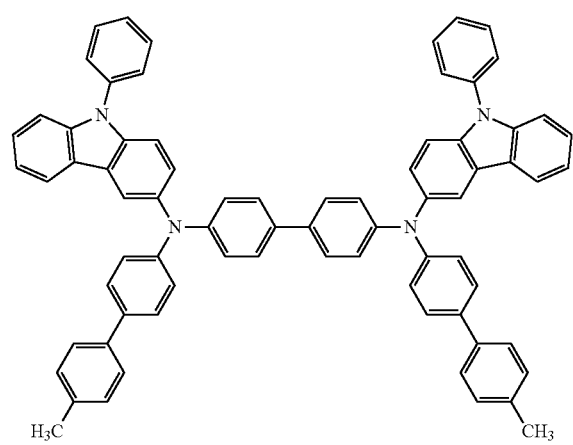
16
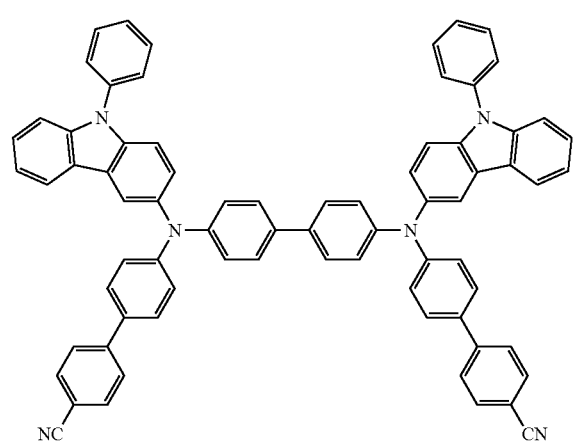
17
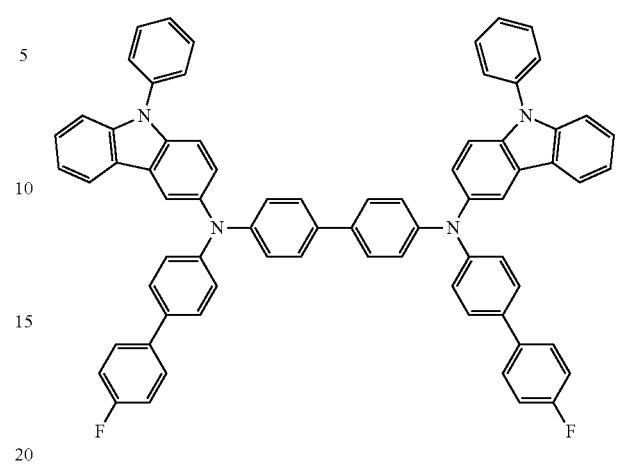
18
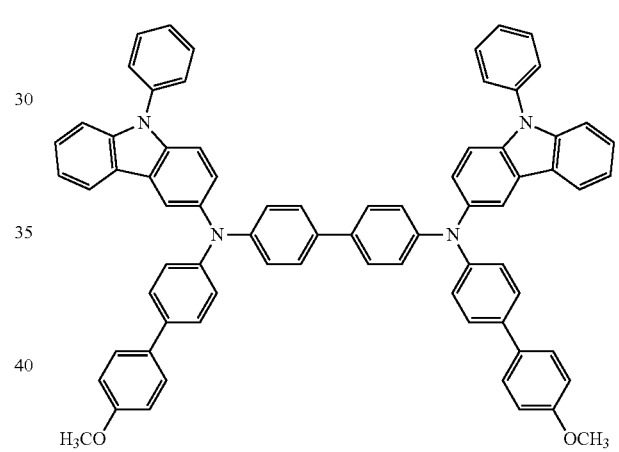
19
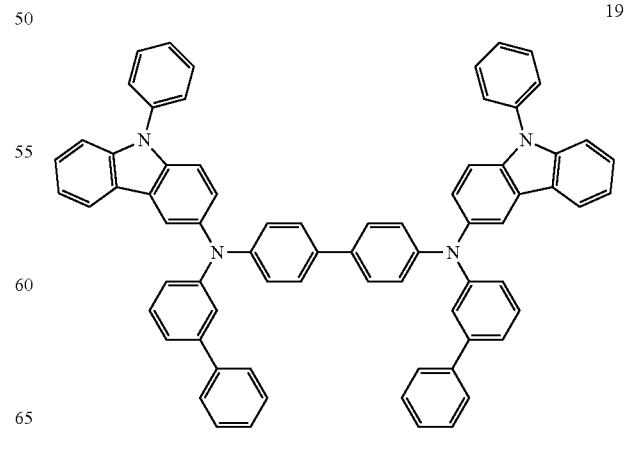

20
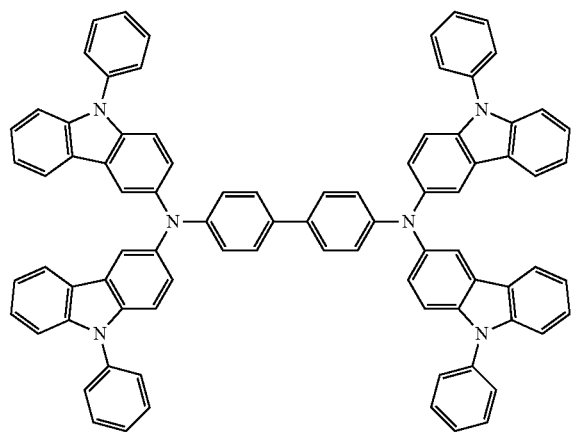
[Chem. 19]
21
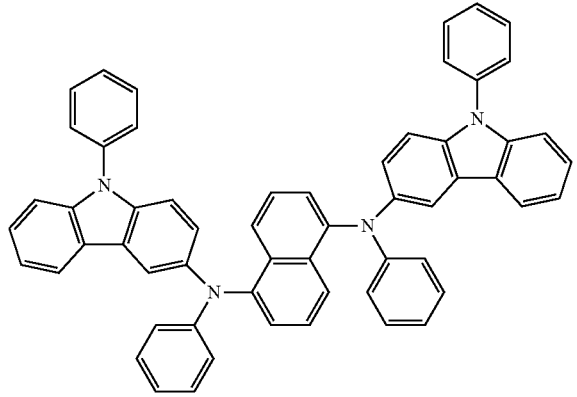
22
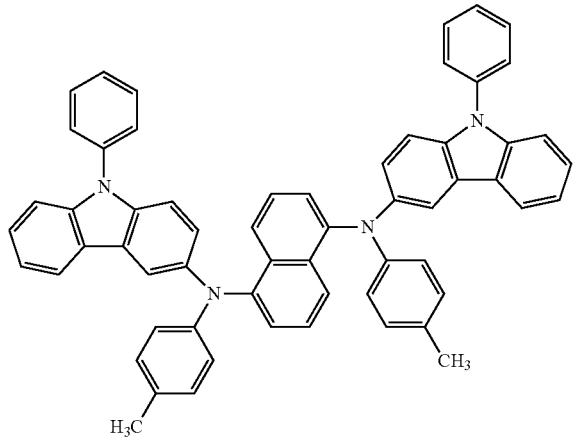
23
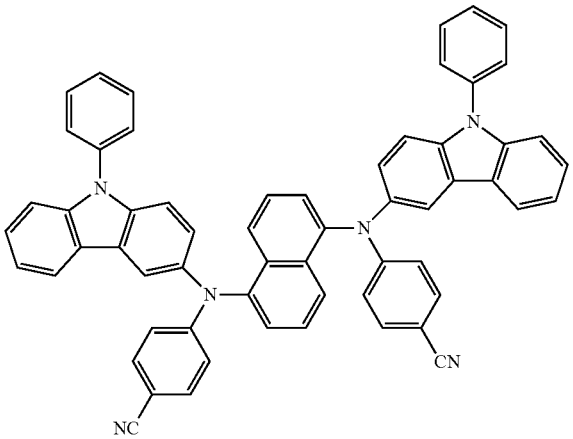
24
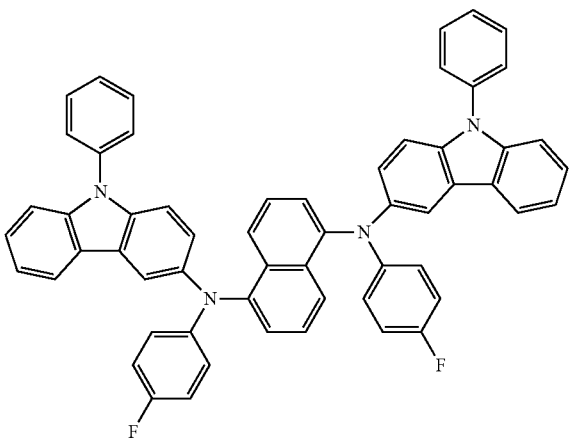
25
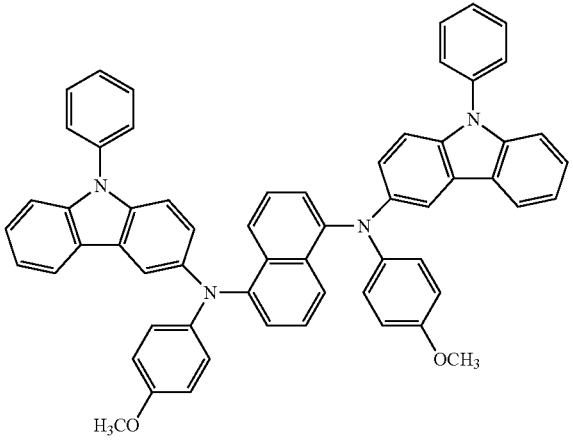

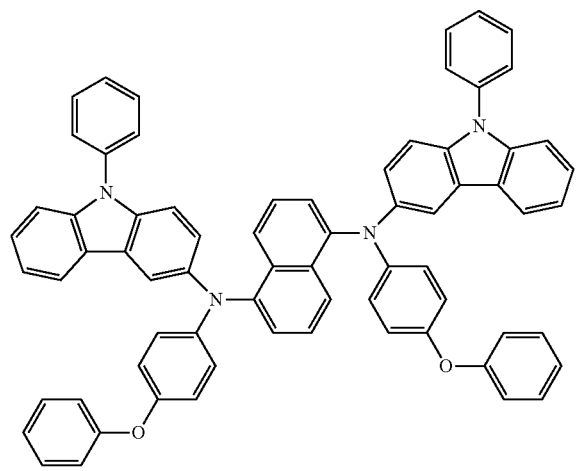
26
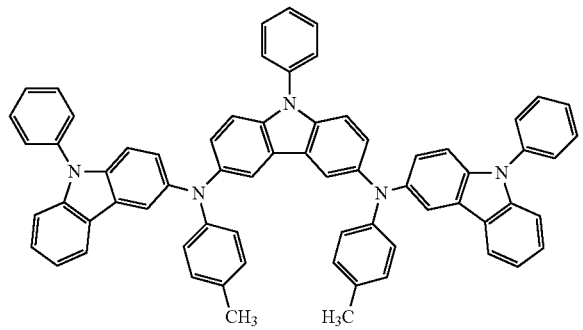
29
[Chem. 20]
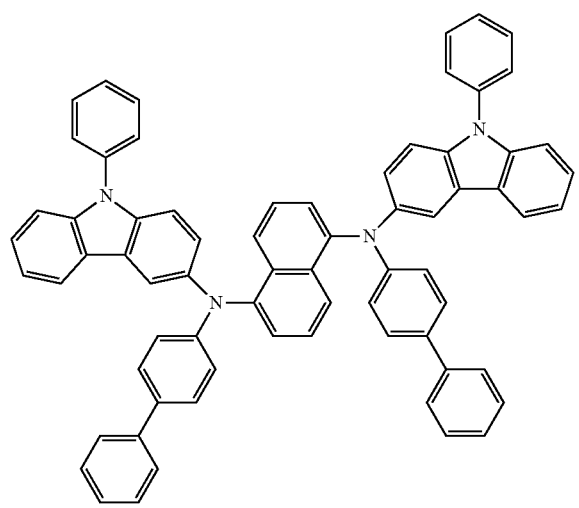
27
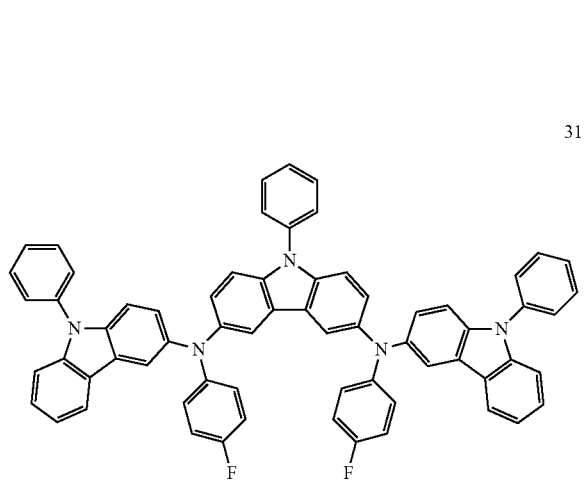
30
31
28
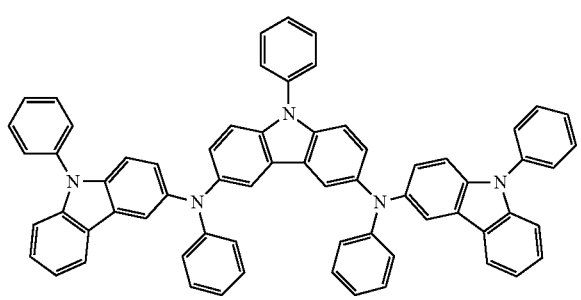
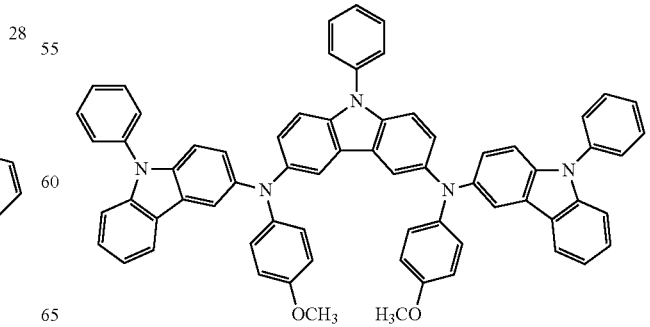
32

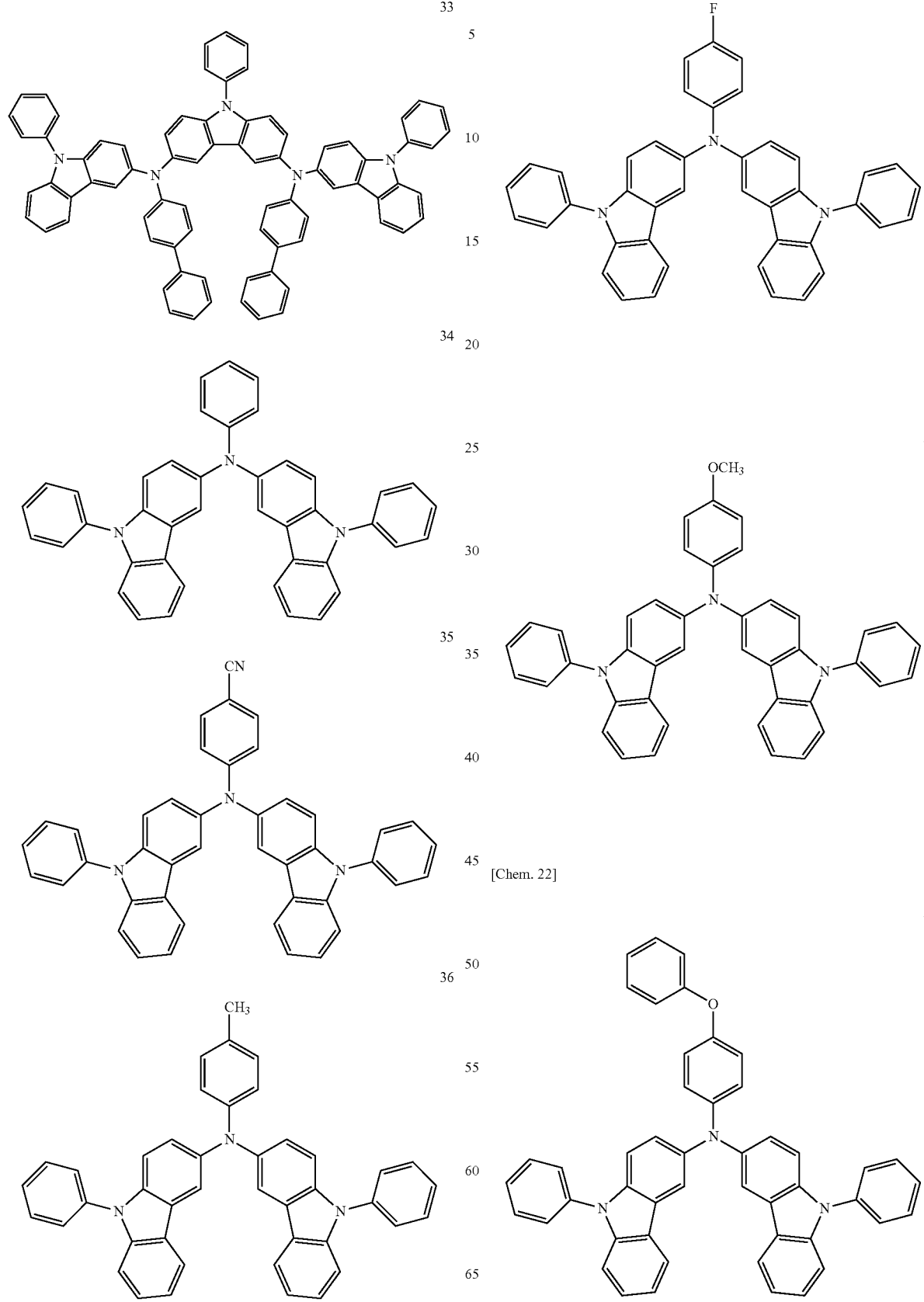

[Chem. 23]
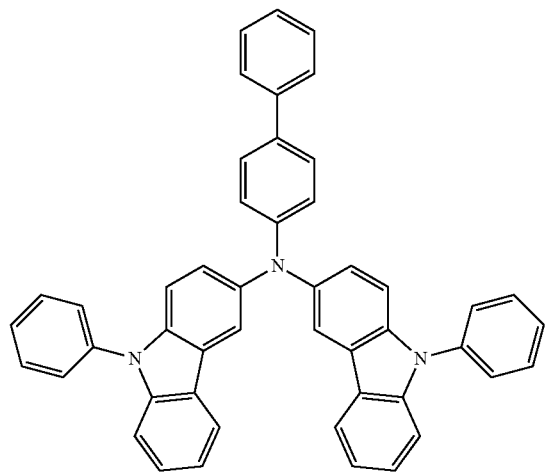
40
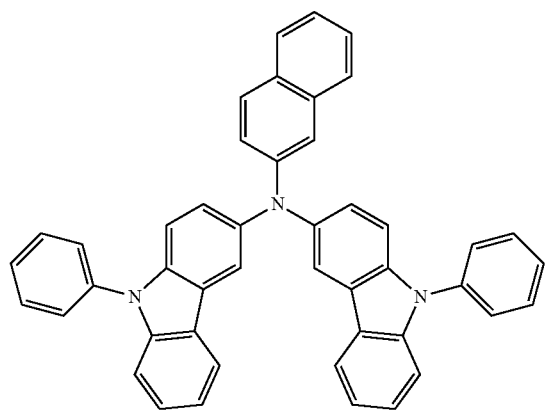
41
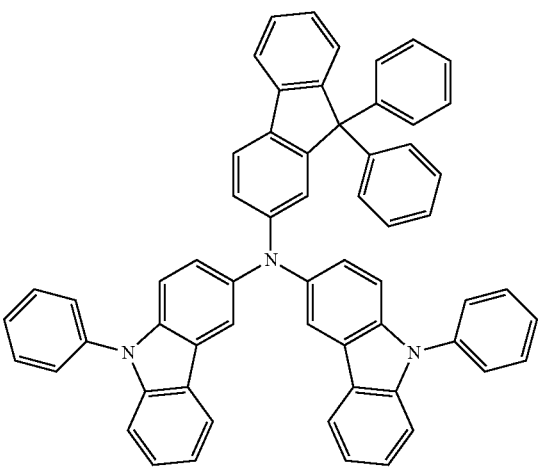
43
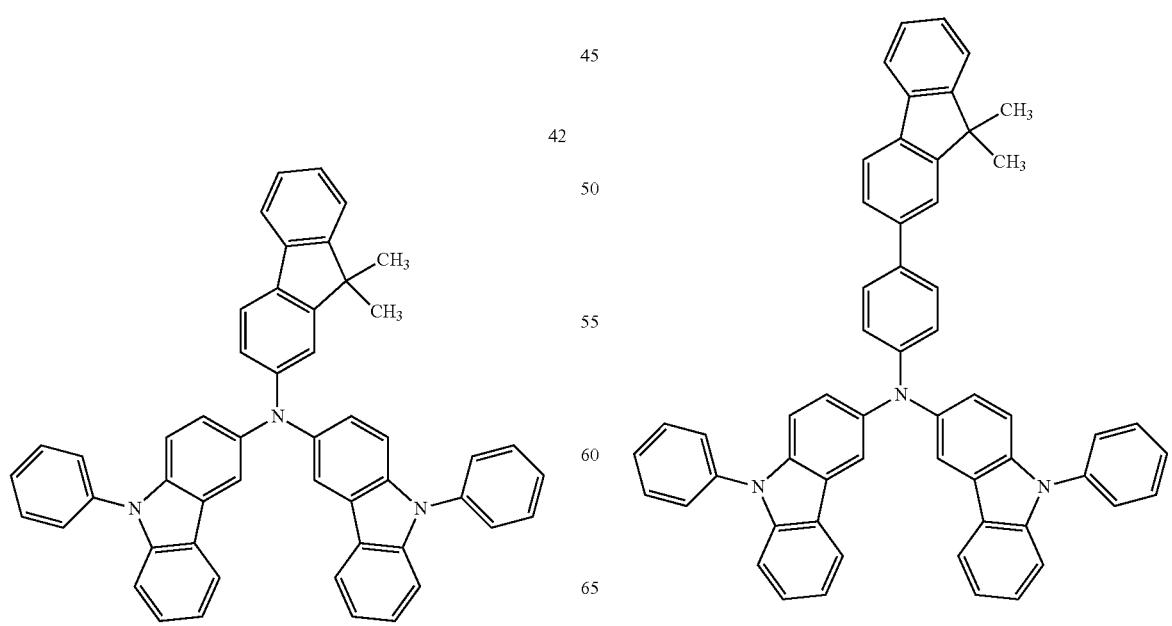
42
44

45
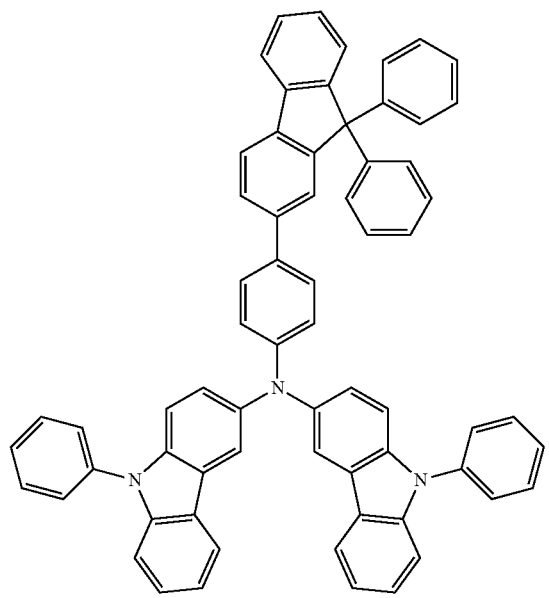
46
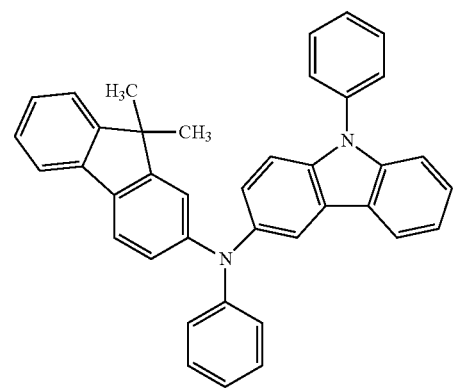
[Chem. 24]
47
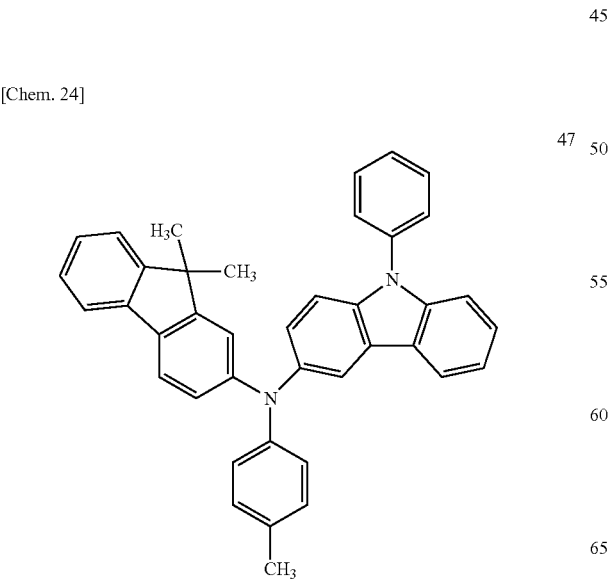
48
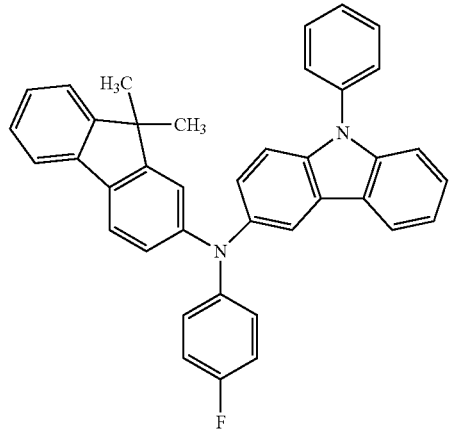
49
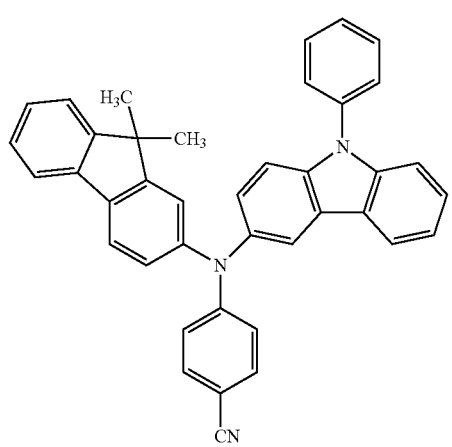
50
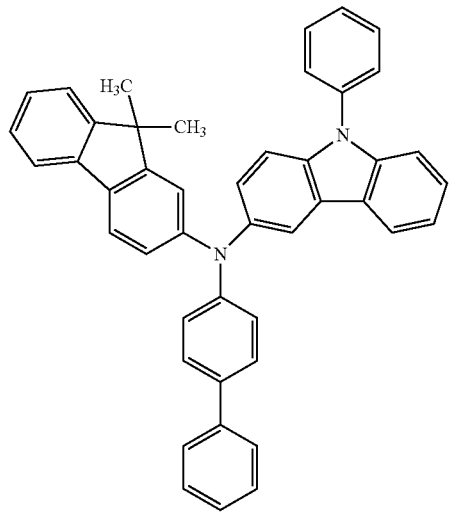

51
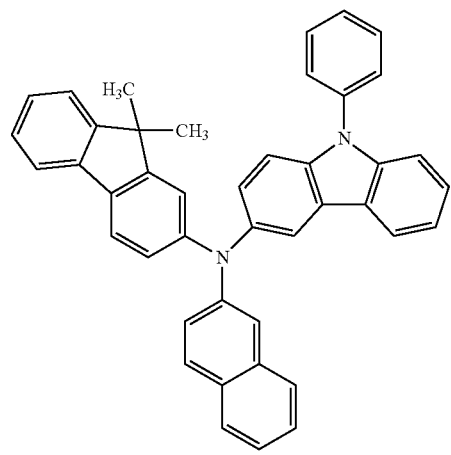
52
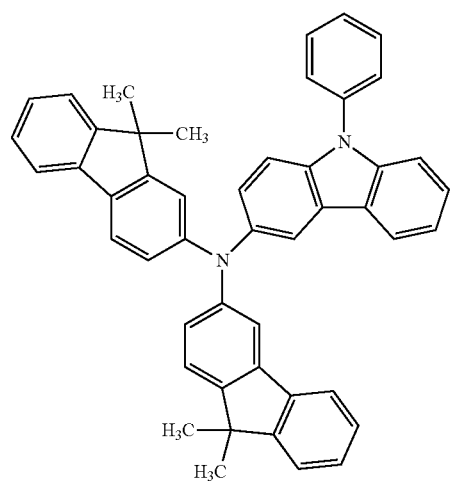
53
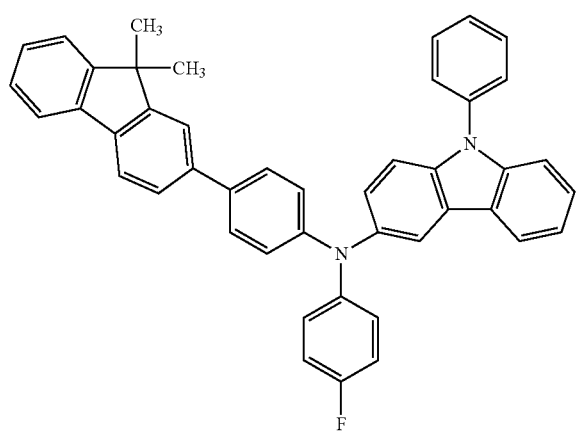
54
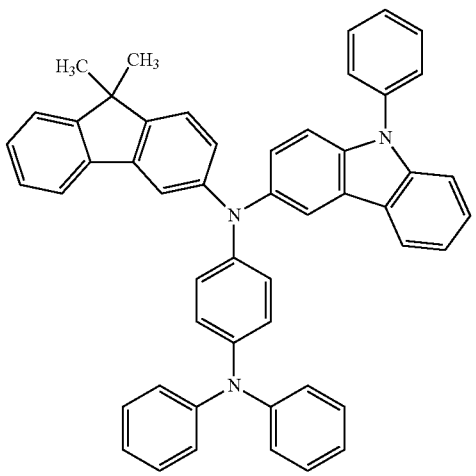
55
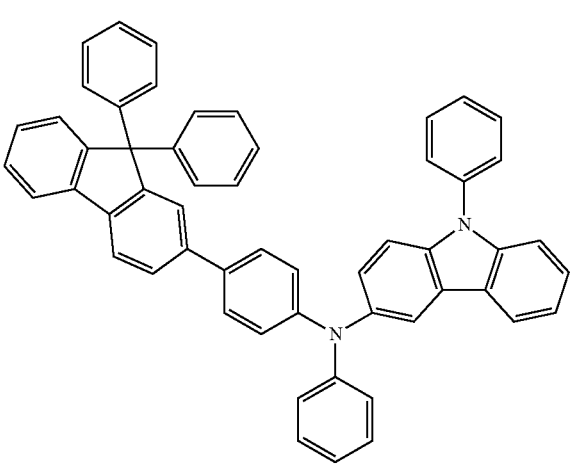
[Chem. 25]
56
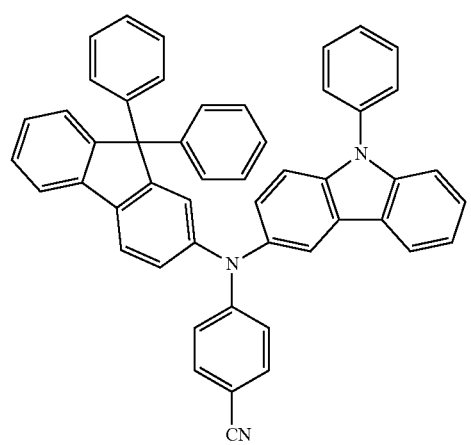

57
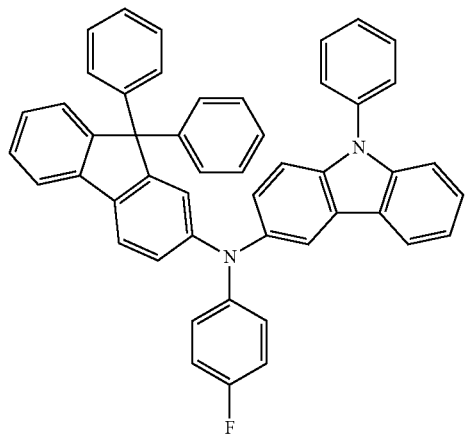
58
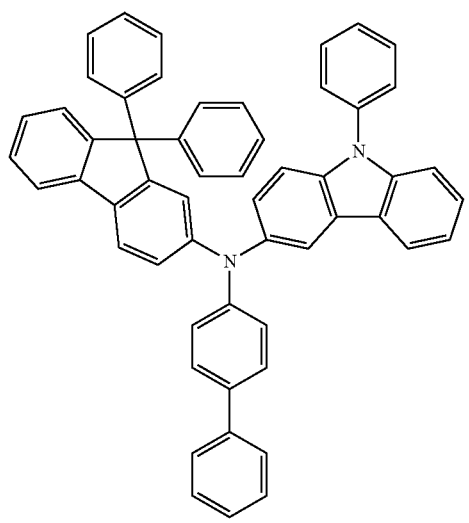
59
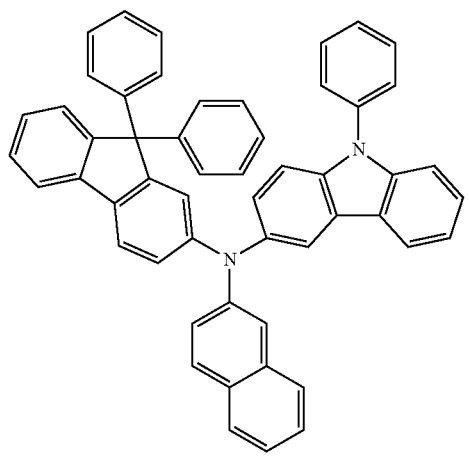
60
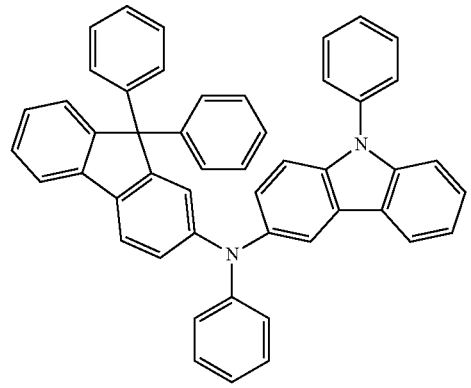
61
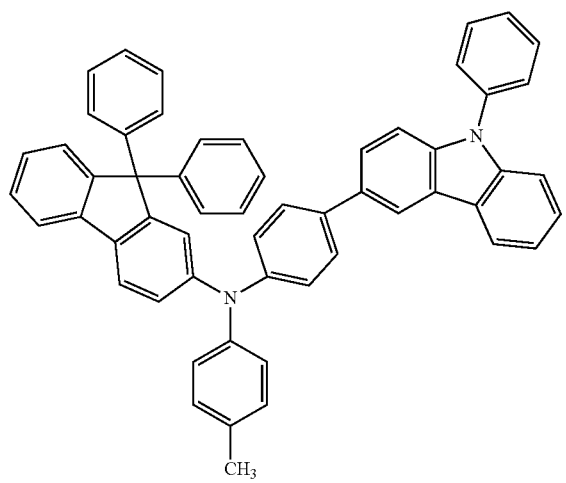
62
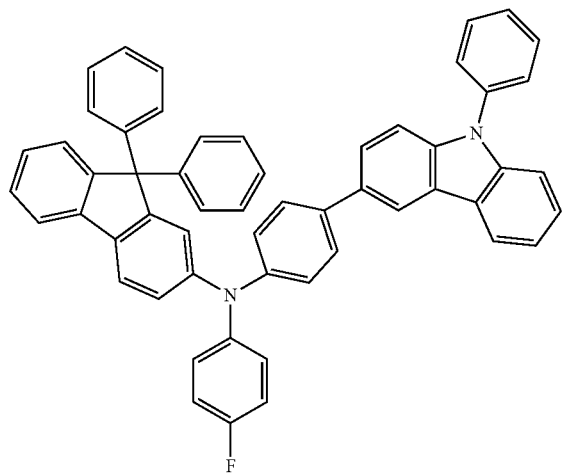

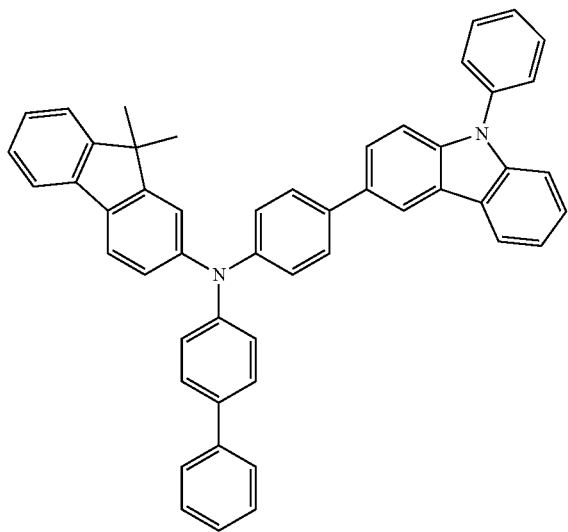

The compound represented by the general formula (Sc-1), (Sb-1), or (Sc-1) can be synthesized by the method described in JP-A-2007-318101. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the light emitting element of the present invention, the compound represented by the general formula (Sa-1), (Sb-1), or (Sc-1) is preferably included in the organic layer between the light emitting layer and the anode, and above all, it is more preferably included in the layer on the anode side adjacent to the light emitting layer, and it is particularly preferably a hole transporting material included in the hole transporting layer.

The compound represented by the general formula (Sa-1), (Sb-1), or (Sc-1) is preferably contained in the amount of 70% by mass to 100% by mass, and more preferably 85% by mass to 100% by mass, with respect to the total mass of the organic layer added.

In addition, with respect to the hole injecting layer and the hole transporting layer, the descriptions in paragraph Nos. [0165] to [0167] of JP-A-2008-270736 can also be applied to the present invention.

The hole injecting layer preferably contains an electron receptive dopant. By incorporating the electron receptive dopant in the hole injecting layer, there are effects in which, for example, the hole injecting properties are improved, the driving voltage is lowered, and the efficiency is improved. The electron receptive dopant may be any one of organic materials and inorganic materials as long as it is capable of withdrawing electrons from a material to be doped and generating radical cations, and examples thereof include TCNQ compounds such as tetracyanoquinodimethane (TCNQ), tetrafluorotetracyanoquinodimethane ($F_4$-TCNQ), hexaazatriphenylene compounds such as hexacyanohexaazatriphenylene (HAT-CN), and molybdenum oxide.

The electron receptive dopant in the hole injecting layer is contained in the amount of preferably from 0.01% by mass to 50% by mass, more preferably from 0.1% by mass to 40% by mass, and still more preferably from 0.2% by mass to 30% by mass, with respect to the total mass of the compounds forming the hole injecting layer.

(A-2) Electron Blocking Layer

The electron blocking layer is a layer having a function of preventing the electrons, which have been transported from the cathode side to the light emitting layer, from passing through to the anode side. In the present invention, the electron blocking layer can be provided as an organic layer adjacent to the light emitting layer on the anode side.

As the organic compound constituting the electron blocking layer, for example, those exemplified above as the hole transporting material can be used.

The thickness of the electron blocking layer is preferably from 1 nm to 500 nm, more preferably from 3 nm to 100 nm, and still more preferably from 5 nm to 50 nm.

The electron blocking layer may have either a single layer structure composed of one or two or more kinds of materials selected from the above-exemplified materials or a multilayer structure composed of a plurality of layers having the same composition or different compositions.

The material used in the electron blocking layer preferably has higher $S_1$ energy than that of the light emitting material from the viewpoints of color purity, luminous efficiency, and driving durability. The $S_1$ in the film state of the material used in the electron blocking layer is preferably higher than the $S_1$ of the light emitting material by 0.1 eV or more, more preferably by 0.2 eV or more, and still more preferably by 0.3 eV or more.

(B) Organic Layer Preferably Disposed Between Cathode and Light Emitting Layer

Next, the (B) organic layer preferably disposed between the cathode and the light emitting layer will be described.

(B-1) Electron Injecting Layer and Electron Transporting Layer

The electron injecting layer and the electron transporting layer are layers having a function of receiving electrons from the cathode or the cathode side and transporting them to the anode side. The electron injecting material and the electron transporting material used in these layers may be either a low-molecular compound or a high-molecular compound.

As the electron transporting material, for example, the compound represented by the general formula (I) can be used. As the other electron transporting materials, anyone selected from aromatic ring tetracarboxylic acid anhydrides, such as pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, benzimidazole derivatives, imidazopyridine derivatives, fluorenone derivatives, anthraquinodimethane derivatives, anthrone derivatives, diphenylquinone derivatives, thiopyranedioxide derivatives, carbodiimide derivatives, fluorenylidenemethane derivatives, distyrylpyrazine derivatives, naphthalene, and perylene; various metal complexes typified by metal complexes of phthalocyanine derivatives or 8-quinolinol derivatives and metal complexes having metal phthalocyanine, benzoxazole, or benzothiazole as a ligand thereof, organic silane derivatives typified by silole, hydrocarbon compounds with fused rings, such as naphthalene, anthracene, phenanthrene, triphenylene, and pyrene is preferred, and any one selected from pyridine derivatives, benzimidazole derivatives, imidazopyridine derivatives, metal complexes, and hydrocarbon compounds with fused rings is more preferred.

From the viewpoint of decreasing the driving voltage, the thickness of each of the electron injecting layer and the electron transporting layer is preferably 500 nm or less.

The thickness of the electron transporting layer is preferably from 1 nm to 500 nm, more preferably from 5 nm to 200 nm, and still more preferably from 10 nm to 100 nm. In addition, the thickness of the electron injecting layer is preferably from 0.1 nm to 200 nm, more preferably from 0.2 nm to 100 nm, and still more preferably from 0.5 nm to 50 nm.

The electron injecting layer and the electron transporting layer may have either a single layer structure composed of one or two or more kinds of the above-described materials or a multilayer structure composed of a plurality of layers having the same composition or different compositions.

The electron injecting layer preferably contains an electron donating dopant. By incorporating the electron donating dopant in the electron injecting layer, there are effects that, for example, the electron injecting properties are improved, the driving voltage is lowered, and the efficiency is improved. The electron donating dopant may be any one of organic materials and inorganic materials as long as it is capable of giving electrons to the material to be doped and generating radical anions, and examples thereof include dihydroimidazole compounds such as tetrathiafulvalene (TTF), tetrathianaphthacene (TTT), and bis-[1,3-diethyl-2-methyl-1,2-dihydrobenzimidazolyl], lithium, and cesium.

The electron donating dopant in the electron injecting layer is contained in the amount of preferably from 0.01% by mass to 50% by mass, more preferably from 0.1% by mass to 40% by mass, and still more preferably 0.5% by mass to 30% by mass, with respect to the total mass of the compounds forming the electron injecting layer.

(B-2) Hole Blocking Layer

The hole blocking layer is a layer having a function of preventing holes, which have been transported from the anode side to the light emitting layer, from passing through to the cathode side. In the present invention, the hole blocking layer can be provided as an organic layer adjacent to the light emitting layer on the cathode side.

In order that the $S_1$ energy of the organic compound in the film state constituting the hole blocking layer prevents the energy movement of excitons produced in the light emitting layer, and thus, does not lower the luminous efficiency, it is preferably higher than $S_1$ energy of the light emitting material.

As an example of the organic compound constituting the hole blocking layer, for example, the compound represented by the general formula (I) can be used.

Examples of the organic compounds constituting the hole blocking layer, other than the compound represented by the general formula (I), include aluminum complexes such as aluminum (III) bis(2-methyl-8-quinolinato) 4-phenylphenolate (abbreviated as Balq), triazole derivatives, and phenanthroline derivatives such as 2,9-dimethyl-4,7-diphenyl-1,10-phenanthroline (abbreviated as BCP).

The thickness of the hole blocking layer is preferably from 1 nm to 500 nm, more preferably from 3 nm to 100 nm, and still more preferably from 5 nm to 50 nm.

The hole blocking layer may have either a single layer structure composed of one or two or more kinds of the above-described materials or a multilayer structure composed of a plurality of layers having the same composition or different compositions.

The material used in the hole blocking layer preferably has higher $S_1$ energy than that of the light emitting material from the viewpoints of color purity, luminous efficiency, and driving durability. The $S_1$ in the film state of the material used in the hole blocking layer is preferably higher than the $S_1$ of the light emitting material by 0.1 eV or more, more preferably by 0.2 eV or more, and still more preferably by 0.3 eV or more.

(B-3) Material which is Particularly Preferably Used in Organic Layer, Preferably Disposed Between Cathode and Light Emitting Layer For the organic electroluminescent element of the present invention, examples of the material which is particularly preferably used in the (B) materials for an organic layer, preferably disposed between the cathode and the light emitting layer include the compound represented by the general formula (I), a compound represented by the following general formula (O-1), and a compound represented by the following general formula (P).

Hereinafter, a compound represented by the general formula (O-1) and a compound represented by the general formula (P) will be described.

The organic electroluminescent element of the present invention preferably includes at least one organic layer between the light emitting layer and the cathode, and the organic layer preferably contains at least one of compounds represented by the following general formula (O-1), from the viewpoint of efficiency or driving voltage of an element. Hereinafter, the general formula (O-1) will be described.

[Chem. 26]

General formula (O-1)

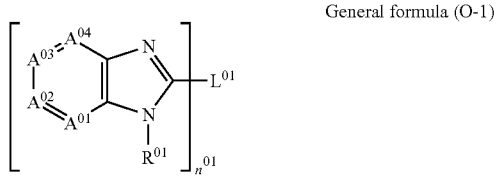

(In the general formula (O-1), $R^{O1}$ represents an alkyl group, an aryl group, or a heteroaryl group. $A^{O1}$ to $A^{O4}$ each independently represent C—$R^A$ or a nitrogen atom. $R^A$ represents a hydrogen atom, an alkyl group, an aryl group, or a heteroaryl group, and a plurality of $R^A$'s may be the same as or different from each other. $L^{O1}$ represents any of divalent to hexavalent linking groups with an aryl ring or a heteroaryl ring. $n^{O1}$ represents an integer of 2 to 6).

$R^{O1}$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $R^{O1}$ is preferably an aryl group or a heteroaryl group, and more preferably an aryl group. Preferred examples of the substituent in the case where the aryl group of $R^{O1}$ has a substituent include an alkyl group, an aryl group, and a cyano group, more preferably an alkyl group and an aryl group, and still more preferably an aryl group. In the case where the aryl group of $R^{O1}$ has a plurality of substituents, the plurality of substituents may be bonded to each other to form a 5- or 6-membered ring. The aryl group of $R^{O1}$ is preferably a phenyl group which may have a substituent selected from Substituent Group A, more preferably a phenyl group which may be substituted with an alkyl group or an aryl group, and still more preferably an unsubstituted phenyl group or 2-phenylphenyl group.

$A^{O1}$ to $A^{O4}$ each independently represent C—$R^A$ or a nitrogen atom. It is preferable that 0 to 2 groups out of $A^{O1}$ to $A^{O4}$ be nitrogen atoms; and it is more preferable that 0 or 1 group out of $A^{O1}$ to $A^{O4}$ be nitrogen atoms. It is preferable that all of $A^{O1}$ to $A^{O4}$ be C—$R^A$, or $A^{O1}$ be a nitrogen atom, and $A^{O2}$ to $A^{O4}$ are C—$R^A$; it is more preferable that $A^{O1}$ be a nitrogen atom, and $A^{O2}$ to $A^{O4}$ be C—$R^A$; it is still more preferable that $A^{O1}$ be a nitrogen atom, $A^{O2}$ to $A^{O4}$ be C—$R^A$, and $R^A$'s be all hydrogen atoms.

$R^A$ represents a hydrogen atom, an alkyl group (preferably having 1 to 8 carbon atoms), an aryl group (preferably having 6 to 30 carbon atoms), or a heteroaryl group (preferably having 4 to 12 carbon atoms), and may have a substituent selected from the above-described Substituent Group A. Further, a plurality of $R^A$'s may be the same as or different from each other. $R^A$ is preferably a hydrogen atom or an alkyl group, and more preferably a hydrogen atom.

$L^{O1}$ represents any of a divalent to hexavalent linking group including an aryl ring (preferably having 6 to 30 carbon atoms) or a heteroaryl ring (preferably having 4 to 12 carbon atoms). $L^{O1}$ is preferably an arylene group, a heteroarylene group, an aryltriyl group, or a heteroaryltriyl group, more preferably a phenylene group, a biphenylene group, or a benzenetriyl group, and still more preferably a biphenylene group or a benzenetriyl group. $L^{O1}$ may have a substituent selected from the above-described Substituent Group A, and in a case of having the substituent, the substituent is preferably an alkyl group, an aryl group, or a cyano group. Specific examples of $L^{O1}$ include the following.

[Chem. 27]

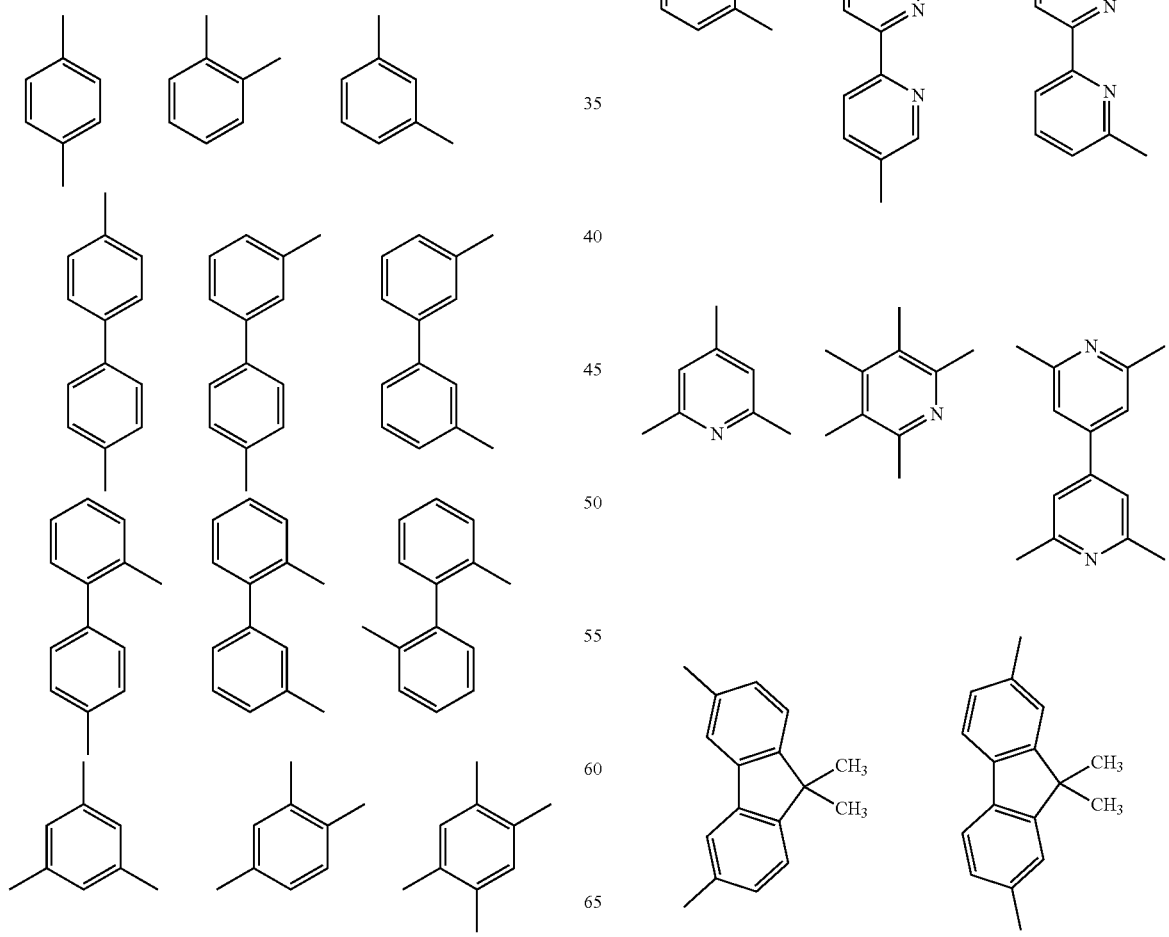

-continued

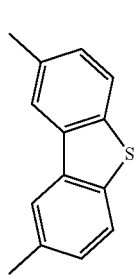 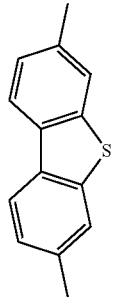

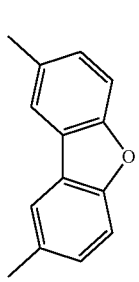 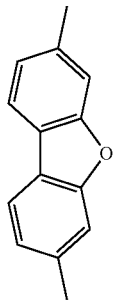

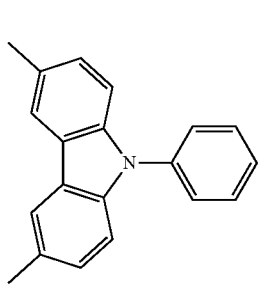 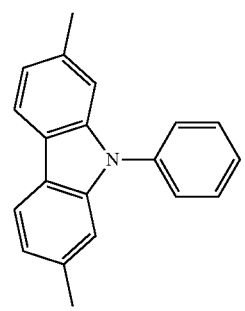

$n^{O1}$ represents an integer of 2 to 6, preferably an integer of 2 to 4, and more preferably 2 or 3. $n^{O1}$ is most preferably 3 from the viewpoint of the efficiency of an element, or most preferably 2 from the viewpoint of the durability of an element.

The glass transition temperature (Tg) of the compound represented by the general formula (O-1) is preferably from 100° C. to 300° C., more preferably from 120° C. to 300° C., and still more preferably from 140° C. to 300° C., from the viewpoint of stability at the time of storage at a high temperature, or stable operation during driving at a high temperature or against heat generation during driving.

Specific examples of the compound represented by the general formula (O-1) are shown below, but the compound represented by the general formula (O-1), which can be used in the present invention, should not be construed to be limited to the specific examples.

[Chem. 28]

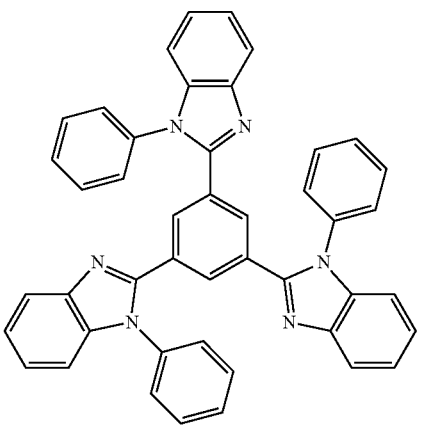

OM-1

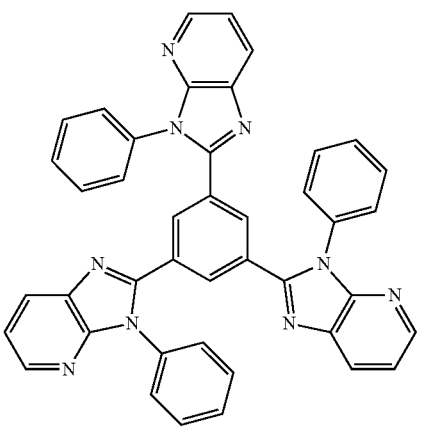

OM-2

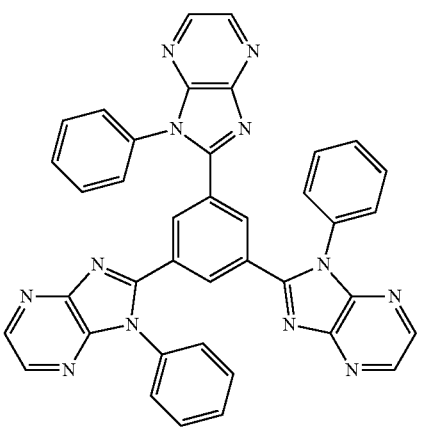

OM-3

-continued
OM-4
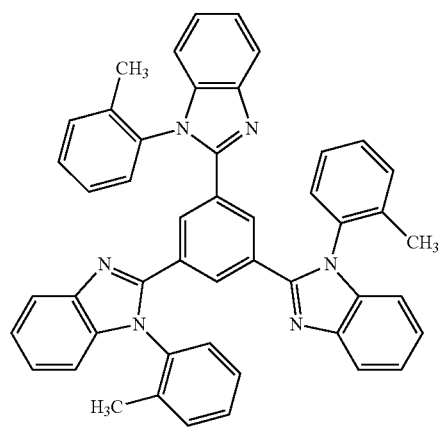
OM-5
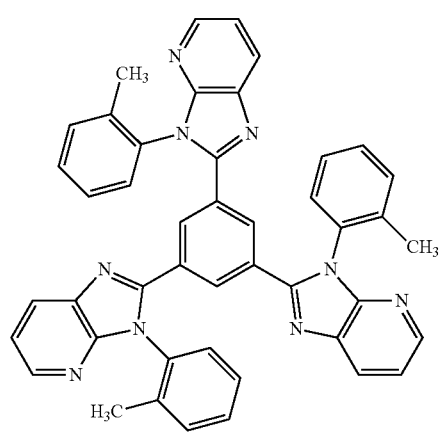
OM-6
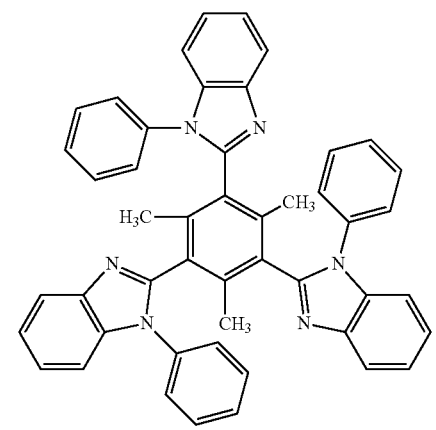
OM-7
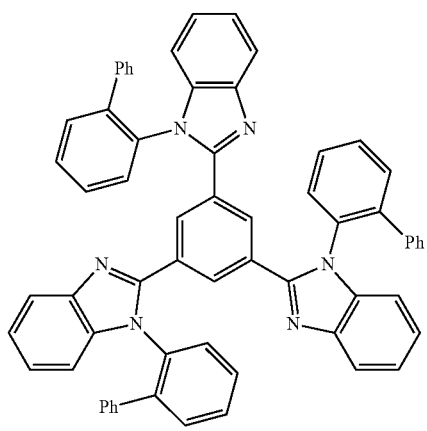
OM-8
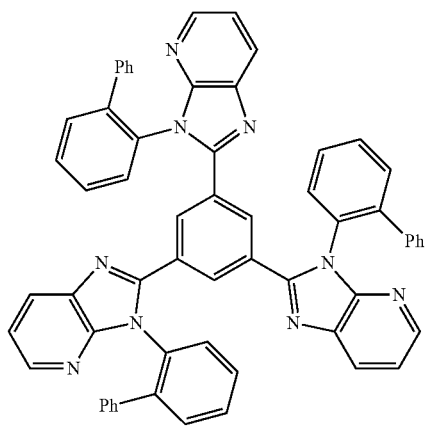
OM-9
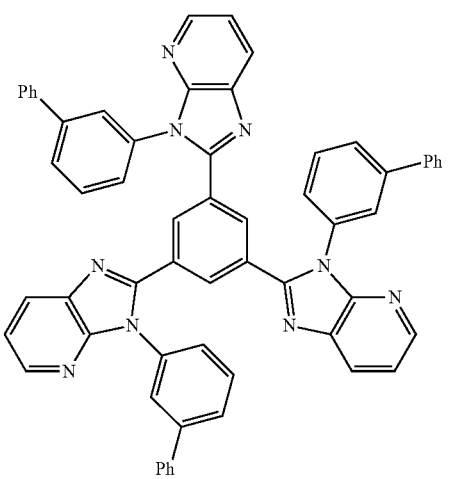

-continued
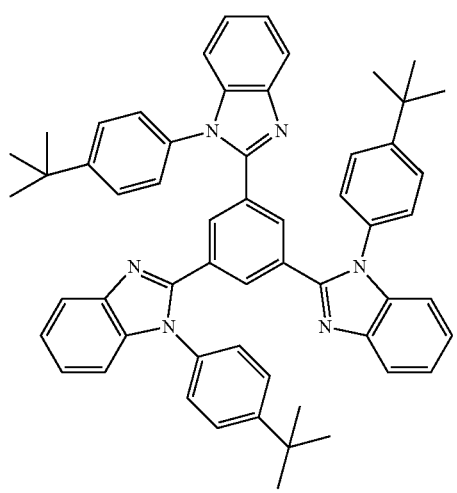
OM-10
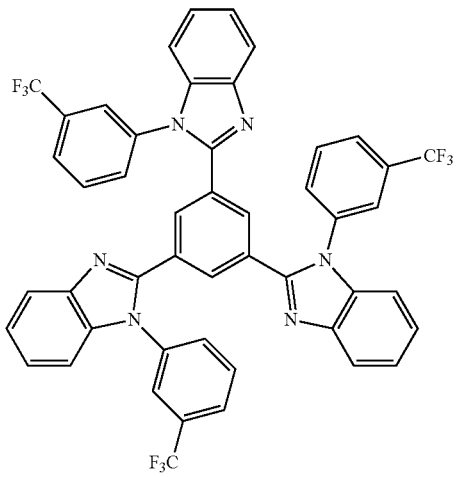
OM-13
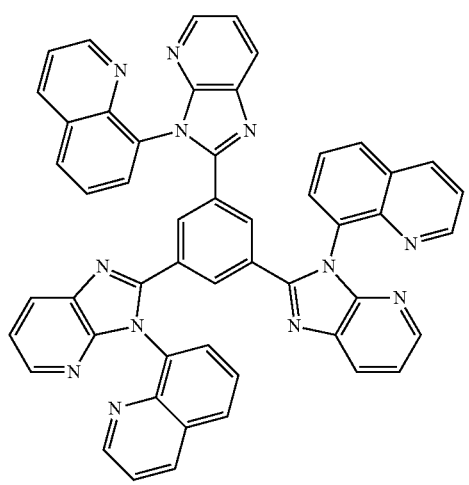
OM-11
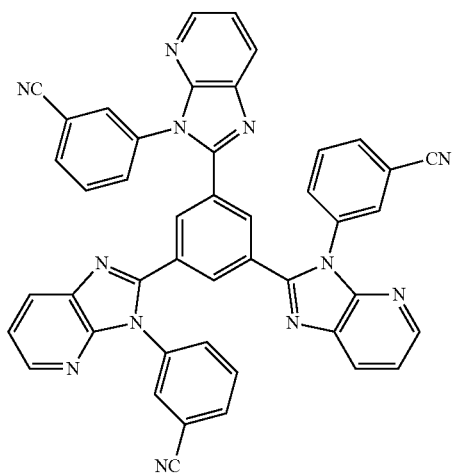
OM-14
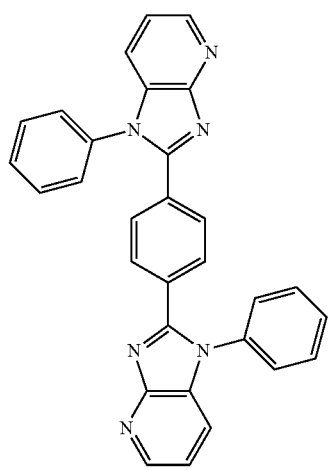
OM-12
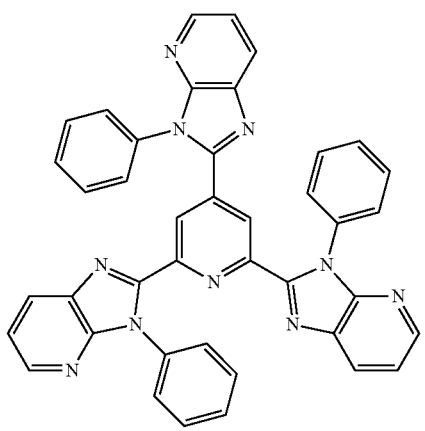
OM-15

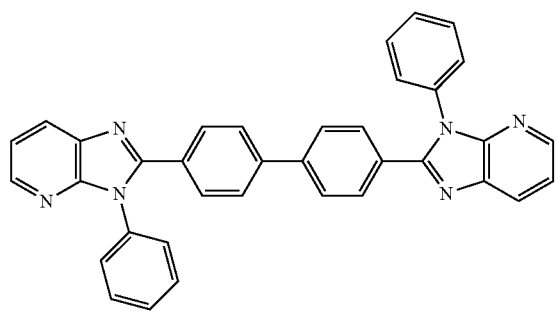

OM-16

The compound represented by the general formula (O-1) can be synthesized by the method described in JP-A-2001-335776. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (O-1) is preferably included in the organic layer between the light emitting layer and the cathode, however, it is more preferably included in the layer on the cathode side adjacent to the light emitting layer.

The compound represented by the general formula (O-1) is preferably contained in the amount of 70% by mass to 100% by mass, and more preferably 85% by mass to 100% by mass, with respect to the total mass of the organic layer added.

The organic electroluminescent element of the present invention preferably includes at least one layer of organic layers between the light emitting layer and the cathode, and it is preferable that the organic layer contain at least one of compounds represented by the following general formula (P), from the viewpoint of efficiency or the driving voltage of an element. Hereinafter, the general formula (P) will be described.

[Chem. 30]

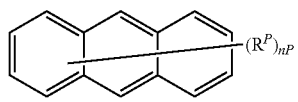

General formula (P)

(In the general formula (P), $R^P$ represents an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. nP represents an integer of 1 to 10, and in the case where there are a plurality of $R^P$'s, these may be the same as or different from each other. At least one of $R^P$'s is a substituent represented by the following general formulae (P-1) to (P-3).

[Chem. 31]

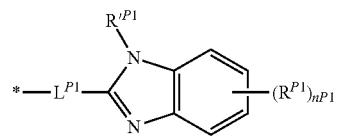

General formula (P-1)

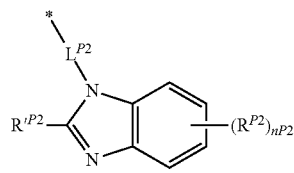

General formula (P-2)

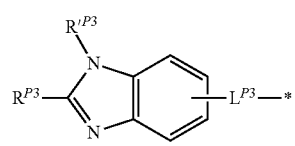

General formula (P-3)

(In the general formulae (P-1) to (P-3), $R^{P1}$ to $R^{P3}$ and $R'^{P1}$ to $R'^{P3}$ each represent an alkyl group (preferably having 1 to 8 carbon atoms), an aryl group (preferably having 6 to 30 carbon atoms), or a heteroaryl group (preferably having 4 to 12 carbon atoms), which may have a substituent selected from the above-described Substituent Group A. $n^{P1}$ and $n^{P2}$ represent an integer of 0 to 4, and in the case where there are a plurality of $R^{P1}$ to $R^{P3}$ and $R'^{P1}$ to $R'^{P3}$, these may be the same as or different from each other. $L^{P1}$ to $L^{P3}$ represent any one of divalent linking groups consisting of a single bond, an aryl ring, or a heteroaryl ring. * represents a binding position with the anthracene ring of the general formula (P)).

A preferred substituent other than the substituents represented by (P-1) to (P-3) as $R^P$ is an aryl group, more preferably any one of a phenyl group, a biphenyl group, a terphenyl group, and a naphthyl group, and still more preferably a naphthyl group.

$R^{P1}$ to $R^{P3}$ and $R'^{P1}$ to $R'^{P3}$ are preferably any one of an aryl group and a heteroaryl group, more preferably an aryl group, still more preferably any one of a phenyl group, a biphenyl group, a terphenyl group, and a naphthyl group, and most preferably a phenyl group.

$L^{P1}$ to $L^{P3}$ are preferably any one of divalent linking groups consisting of a single bond and an aryl ring, more preferably any one of a single bond, phenylene, biphenylene, terphenylene, and naphthylene, and still more preferably any one of a single bond, phenylene, and naphthylene.

Specific examples of the compound represented by the general formula (P) are shown below, but the compound represented by the general formula (P) that can be used in the present invention should not be construed to be limited to the specific examples.

[Chem. 32]
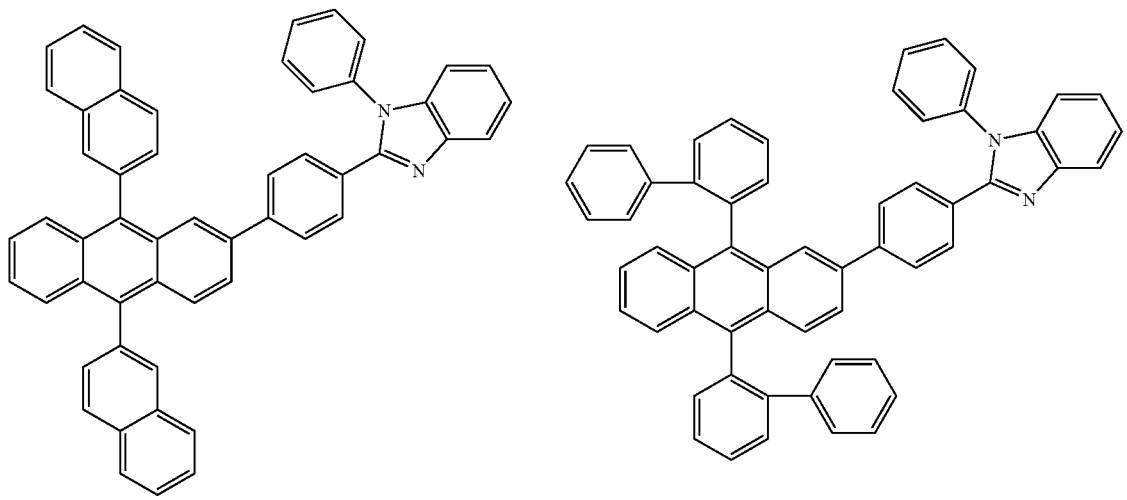
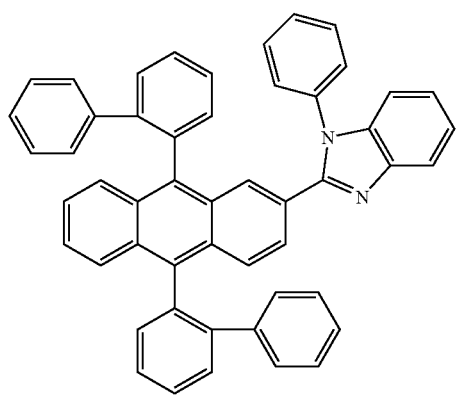
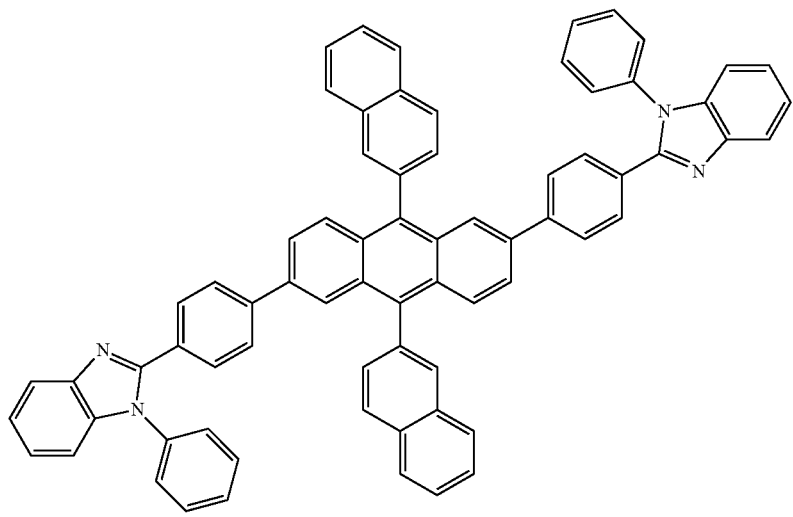

-continued
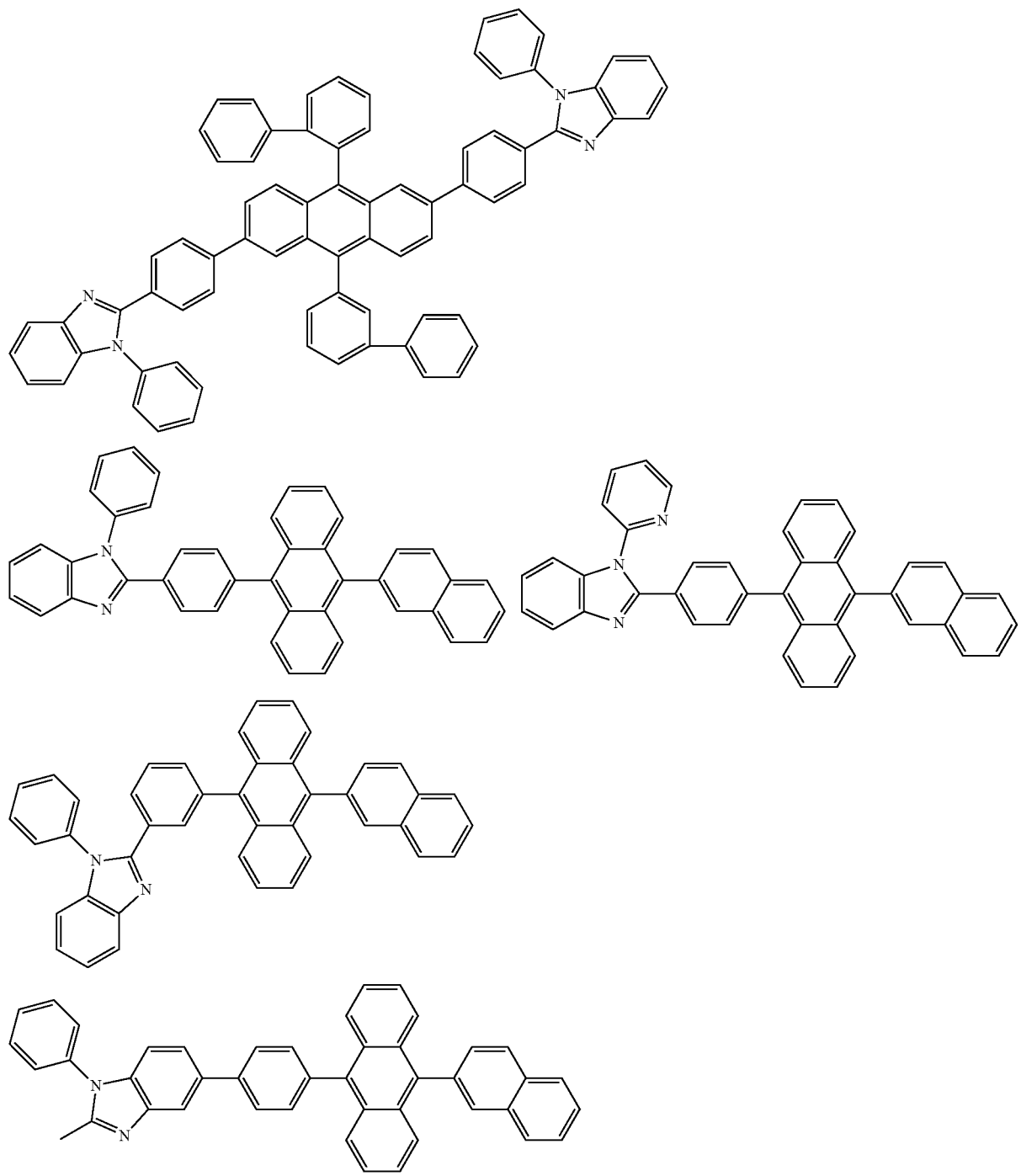
[Chem. 33]
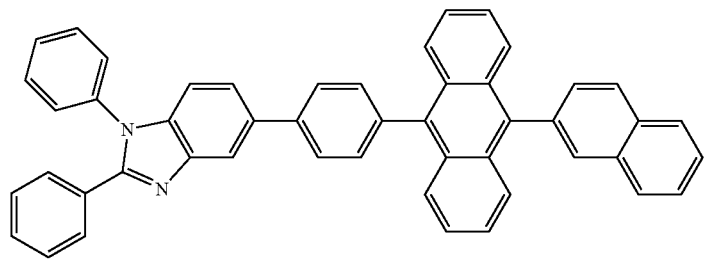

-continued

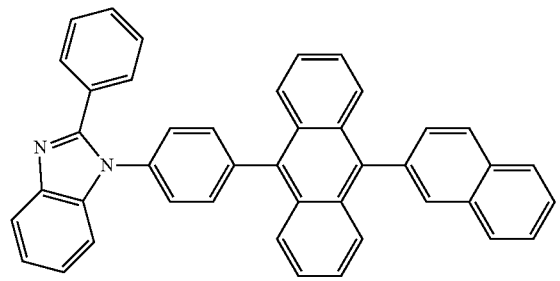
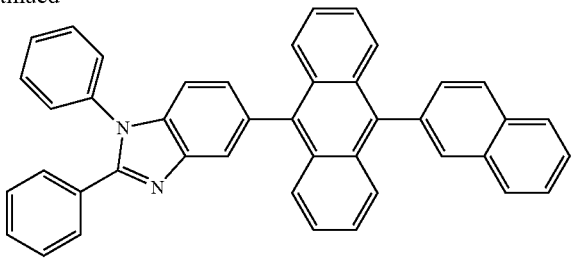

The compound represented by the general formula (P) can be synthesized by the method described in WO 2003/060956 and WO 2004/080975. After the synthesis, purification is preferably carried out by column chromatography, recrystallization, reprecipitation, or the like, and then by sublimation purification. By the sublimation purification, organic impurities can be separated and inorganic salts, residual solvents, moisture, or the like can be removed effectively.

In the organic electroluminescent element of the present invention, the compound represented by the general formula (P) is preferably included in the organic layer between the light emitting layer and the cathode, and more preferably in the layer adjacent to the cathode.

The compound represented by the general formula (P) is preferably contained in the amount of 70% by mass to 100% by mass, and more preferably 85% by mass to 100% by mass, based on the total mass of the organic layer added.

<Protective Layer>

In the present invention, the entirety of the organic electroluminescent element may be protected by a protective layer.

For the protective layer, the detailed description in paragraph Nos. [0169] to [0170] of JP-A-2008-270736 can also be applied to the present invention. Incidentally, the materials for the protective layer may be either an inorganic material or an organic material.

<Sealing Enclosure>

For the organic electroluminescent element according to the present invention, the entirety of the element may be sealed using a sealing enclosure.

For the sealing enclosure, the detailed description in paragraph No. [0171] of JP-A-2008-270736 can be applied to the present invention.

<Driving Method>

The organic electroluminescent element of the present invention can emit light by applying a direct current (it may contain an alternate current component, if necessary) voltage (typically from 2 volts to 15 volts) or a direct current between the anode and the cathode.

As a driving method of the organic electroluminescent element of the present invention, driving methods described in JP-A-2-148687, JP-A-6-301355, JP-A-5-29080, JP-A-7-134558, JP-A-8-234685, and JP-A-8-241047, Japanese Patent No. 2784615, and U.S. Pat. Nos. 5,828,429 and 6,023,308 can be applied.

The external quantum efficiency of the organic electroluminescent element of the present invention is preferably 5% or more, more preferably 6% or more, and still more preferably 7% or more. As to the numerical value of the external quantum efficiency, a maximum value of the external quantum efficiency obtained when the organic electroluminescent element is driven at 20° C., or a value of the external quantum efficiency in the vicinity of 300 cd/m$^2$ to 400 cd/m$^2$ obtained when the element is driven at 20° C. can be employed.

The internal quantum efficiency of the organic electroluminescent element of the present invention is preferably 30% or more, more preferably 50% or more, and still more preferably 70% or more. The internal quantum efficiency of the element is calculated by dividing the external quantum efficiency by the light extraction efficiency. The light extraction efficiency in usual organic EL elements is about 20%, but by taking into consideration the shape of a substrate, the shape of an electrode, the thickness of an organic layer, the thickness of an inorganic layer, the refractive index of an organic layer, the refractive index of an inorganic layer, or the like, it is possible to increase the light extraction efficiency to 20% or more.

<Light Emitting Wavelength>

In the organic electroluminescent element of the present invention, its light emitting wavelength is not limited, but is preferably used for blue or white light emission. Above all, in the organic electroluminescent element of the present invention, it is preferable to use the compound represented by the general formula (I) as a light emitting material to emit light, and particularly preferably to emit blue light.

<Use of Organic Electroluminescent Element of the Present Invention>

The organic electroluminescent element of the present invention can be suitably used for display elements, displays, backlights, electrophotography, illumination light sources, recording light sources, exposure light sources, readout light sources, signs, billboards, interior decorations, optical communications, and the like, and particularly preferably for devices driven in a region of high-intensity luminescence, such as a light emitting device, an illumination device, and a display device.

[Light Emitting Device]

The light emitting device of the present invention may include the organic electroluminescent element of the present invention.

Next, the light emitting device of the present invention will be described with reference to FIG. 2.

The light emitting device of the present invention is formed by using the organic electroluminescent element.

Figure 2:
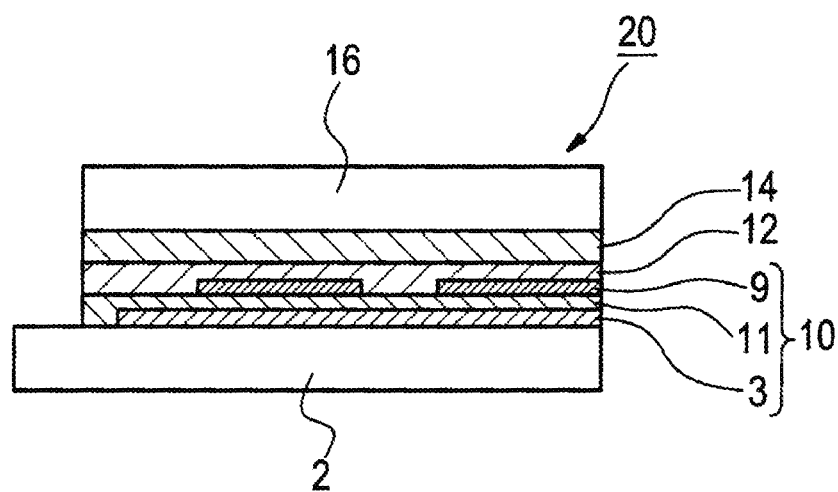
FIG. 2 is a schematic view showing one example of a light emitting device according to the present invention.

FIG. 2 is a cross-sectional view schematically showing one example of the light emitting device of the present invention. The light emitting device 20 in FIG. 2 includes a transparent substrate 2 (supporting substrate), an organic electroluminescent element 10, a sealing enclosure 16, and the like.

The organic electroluminescent element 10 is formed by laminating on the substrate 2 an anode 3 (first electrode), an organic layer 11, and a cathode 9 (second electrode) in this order. In addition, a protective layer 12 is laminated on the cathode 9, and a sealing enclosure 16 is further provided via an adhesive layer 14 on the protective layer 12. Incidentally, a part of each of the electrodes 3 and 9, a diaphragm, an insulating layer, and the like are omitted in FIG. 2.

Here, a photocurable adhesive such as an epoxy resin, or a thermosetting adhesive can be used for the adhesive layer 14, and for example, a thermosetting adhesive sheet may also be used as the adhesive layer 14.

The light emitting device of the present invention is not particularly limited in its use, and it can be used as not only an illumination device but also a display device of a television set, a personal computer, a mobile phone, electronic paper, or the like.

[Illumination Device]

The illumination device of the present invention includes the organic electroluminescent element of the present invention.

Next, the illumination device of the present invention will be described with reference to FIG. 3.

Figure 3:
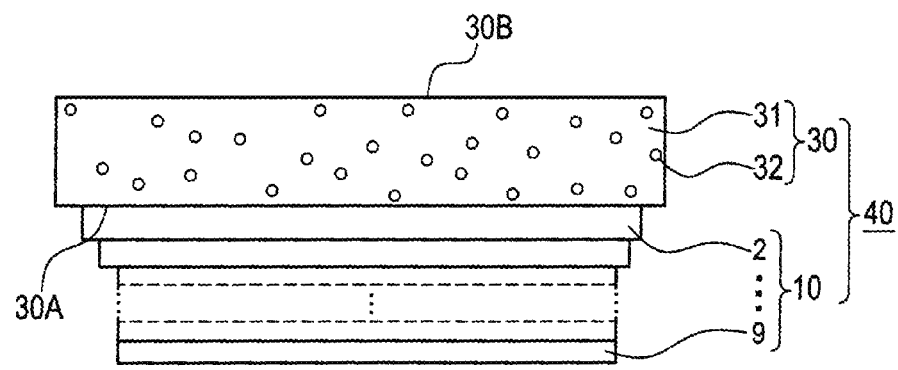
FIG. 3 is a schematic view showing one example of an illumination device according to the present invention.

FIG. 3 is a cross-sectional view schematically showing one example of the illumination device of the present invention. The illumination device 40 of the present invention includes, as shown in FIG. 3, the above-described organic EL element 10 and a light scattering member 30. More specifically, the illumination device 40 is configured such that the substrate 2 of the organic EL element 10 and the light scattering member 30 are in contact with each other.

The light scattering member 30 is not particularly limited as long as it can scatter light, but in FIG. 3, a member obtained by dispersing fine particles 32 in a transparent substrate 31 is used. Suitable examples of the transparent substrate 31 include a glass substrate, and suitable examples of the fine particles 32 include transparent resin fine particles. As the glass substrate and the transparent resin fine particles, a known product can be used for both. In such an illumination device 40, when light emitted from the organic electroluminescent element 10 is incident on the light incident surface 30A of the scattering member 30, the incident light is scattered by the light scattering member 30 and the scattered light is output as illuminating light from the light output surface 30B.

[Display Device]

The display device of the present invention may include the organic electroluminescent element of the present invention.

The display device of the present invention may be used for, for example, a display device of a television set, a personal computer, a mobile phone, electronic paper, or the like.

EXAMPLES

The characteristic features of the present invention are hereunder described in more detail with reference to the following Examples and Comparative Examples. The materials, use amounts, ratios, treatment details, treatment procedures, and the like shown in the following Examples and Comparative Examples can be appropriately modified so far as the gist of the present invention is not deviated. Accordingly, it should not be construed that the scope of the present invention is limited to the specific examples shown below.

The structural formulae of the compounds F1 to F19 represented by the general formula (I) used in Examples, and the structural formulae of the compounds D1 to D6 used in Comparative Examples are summarized below.

[Chem. 34]

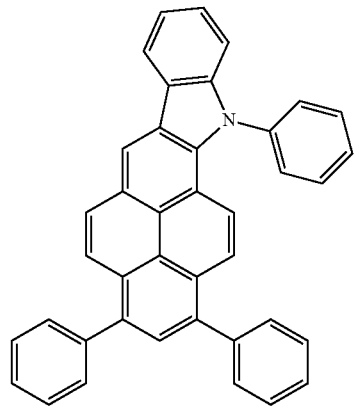

F1

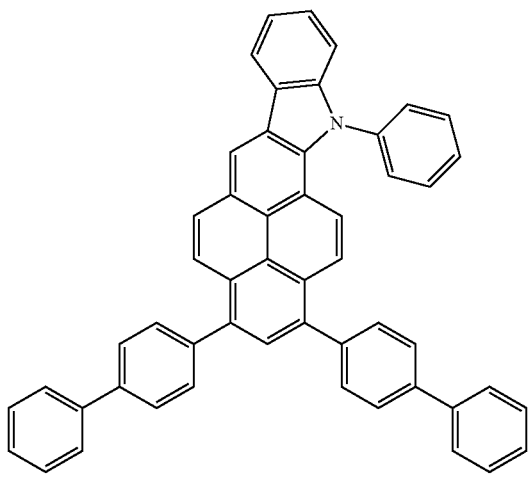

F2

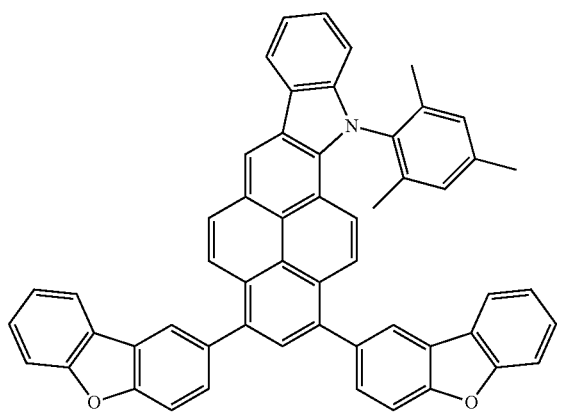

F3

-continued
F4
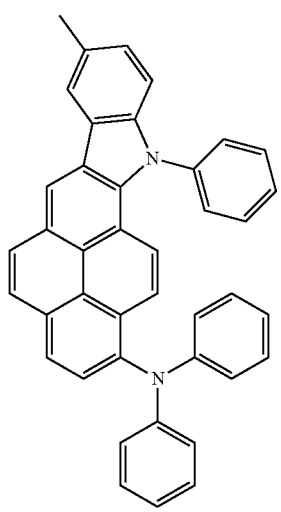
F5
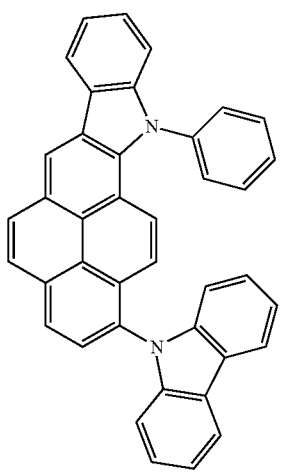
F6
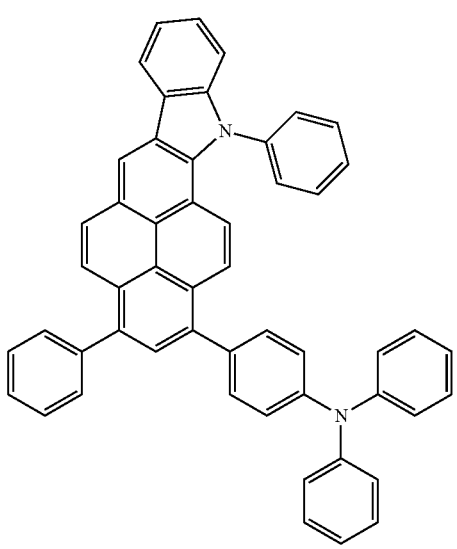
-continued
F7
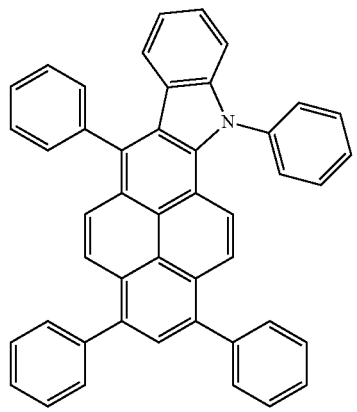
F8
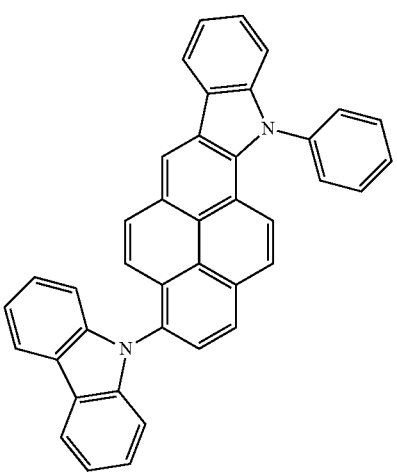
F9
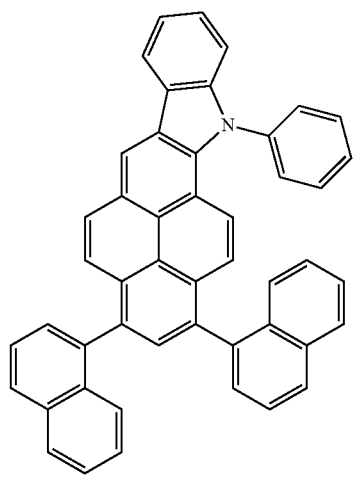

-continued
F10
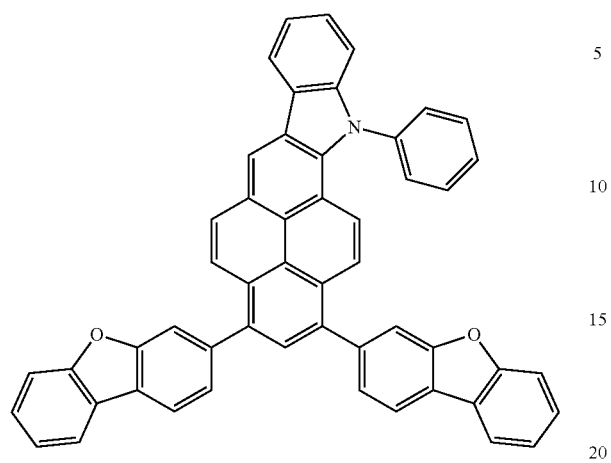
[Chem. 35]
F11
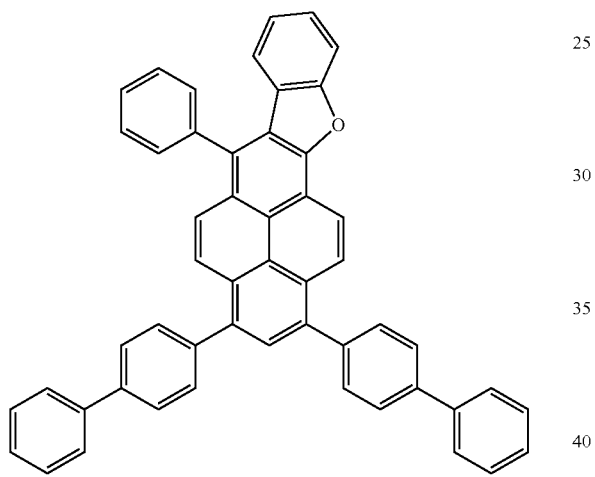
F12
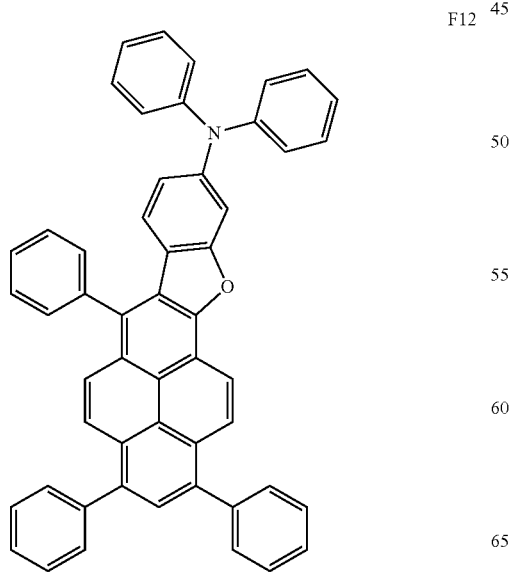
-continued
F13
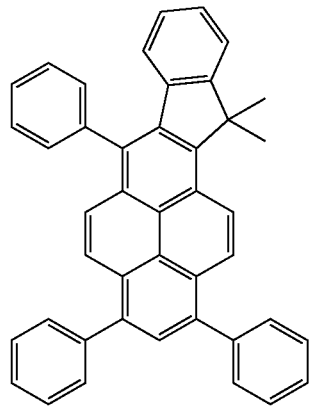
F14
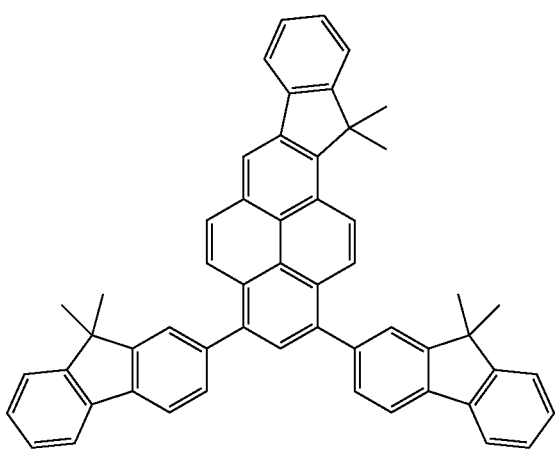
F15
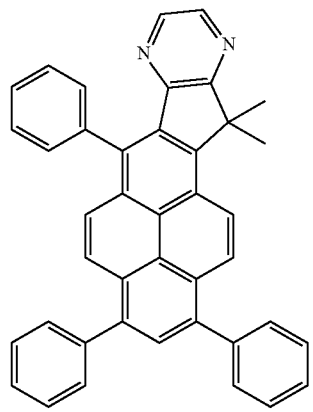

F16
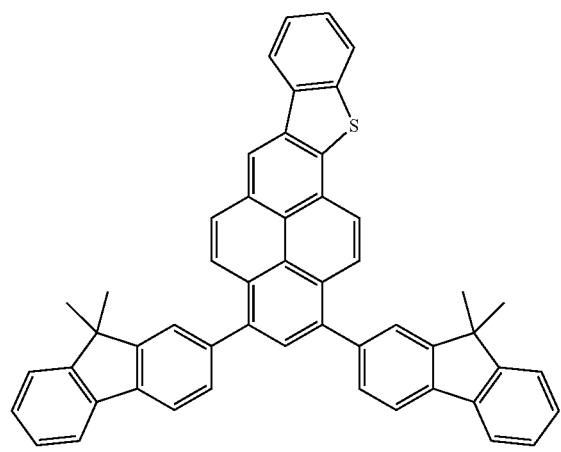
F17
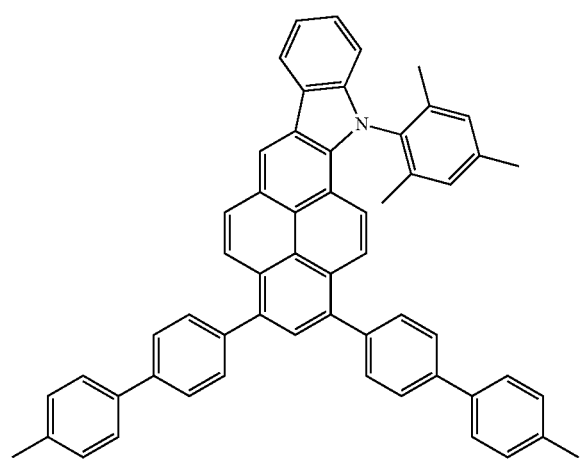
F18
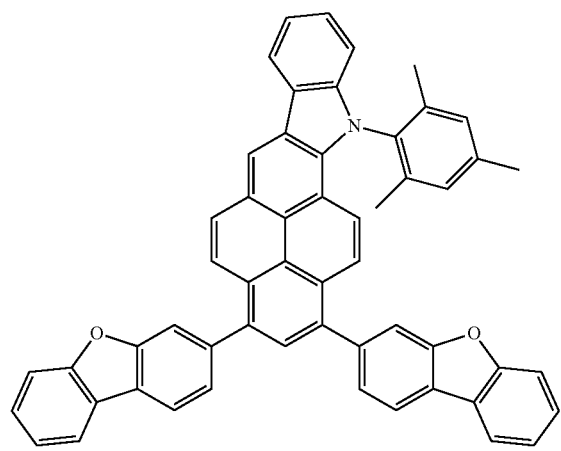
F19
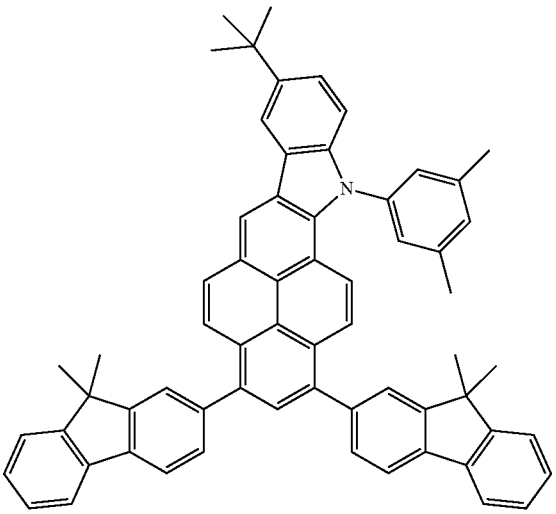
D1: Comparative compound described in JP-A-2011-51969
[Chem. 36]
D1
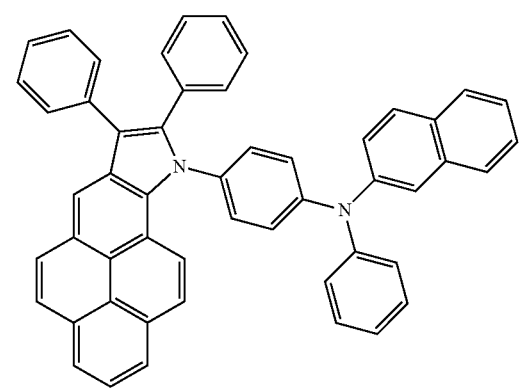
D2: Comparative compound described in JP-A-2011-79822

[Chem. 37]
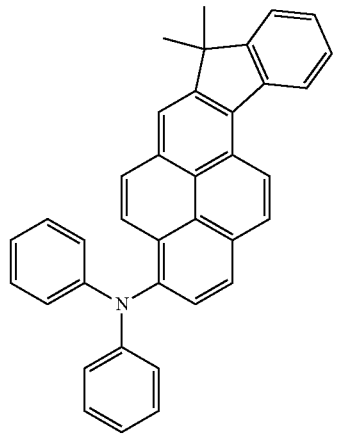
[Chem. 38]
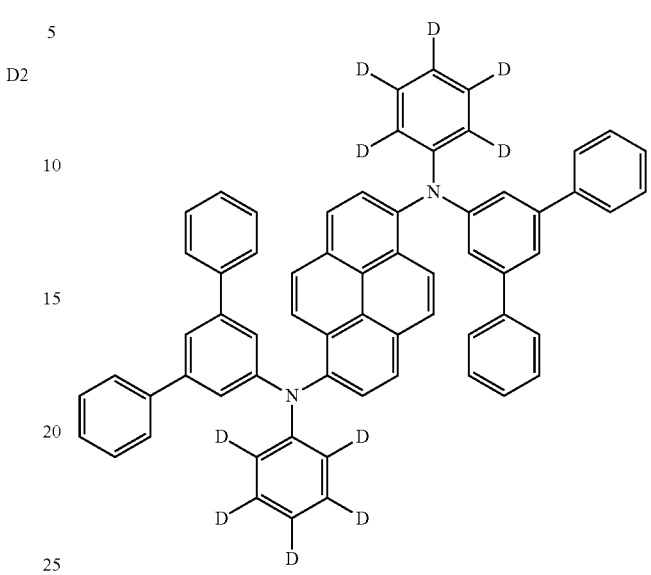
D3: Comparative compound having the same structure of EMB-1 which is a material used in Example below
D4 to D6: Comparative compounds described as compounds (37), (91), and (98), respectively, in WO2010/012328
[Chem. 39]
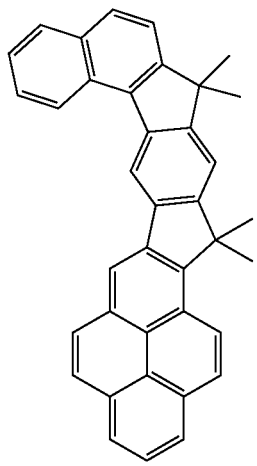
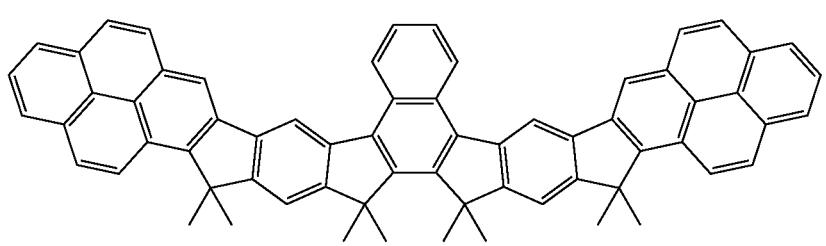

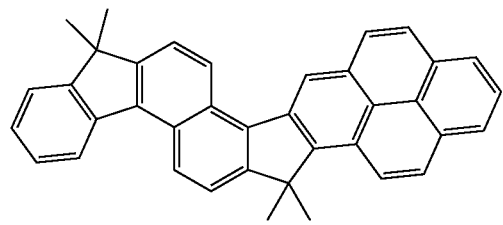

Synthesis Examples

The compound represented by the general formula (I) can be synthesized by the method described in the present specification or a combination of other known reactions. Representative examples of the specific synthesis procedure of the compound represented by the general formula (I) will be described below.

(Synthesis Examples 1 and 2) Synthesis of Compounds F1 and F13

The compounds F1 and F13 were synthesized according to the following scheme.

[Chem. 40]

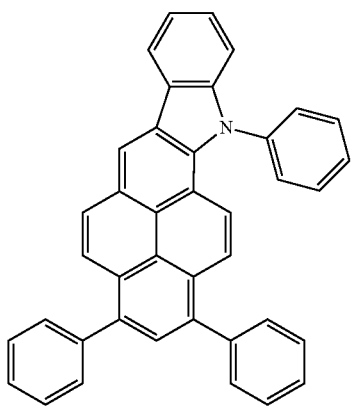

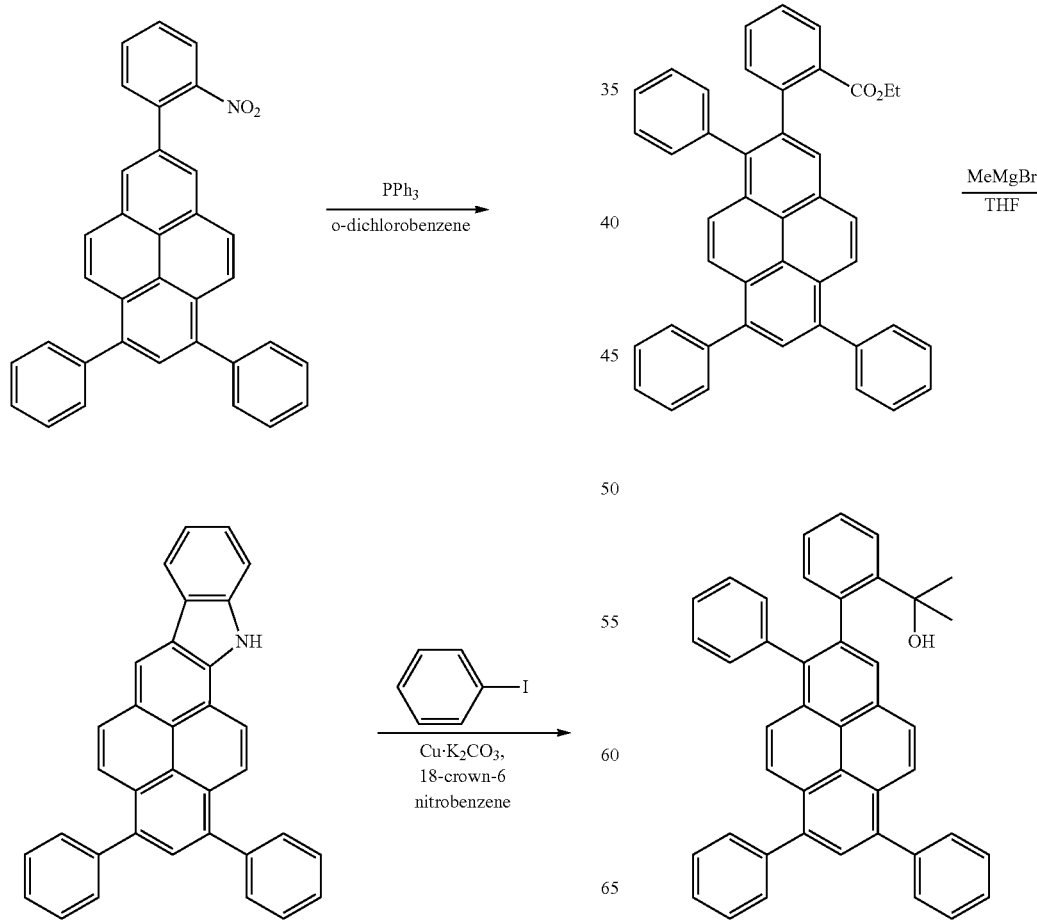

-continued

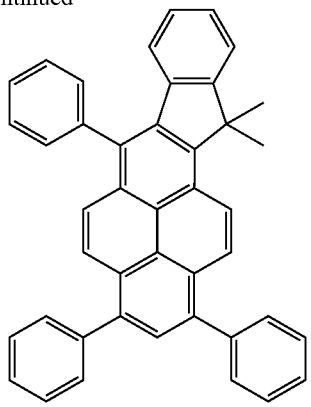

The compounds F1 to F19 used in Examples as well as the compounds other than the compounds F1 and F13 synthesized above were synthesized by a method similar to that for the compounds F1 and F13. The comparative compounds D1 to D6 were synthesized with reference to well-known literatures, in which the respective compounds are described.

Examples 1 to 8

<Evaluation of Elements>
(1) Purity of Materials Used

The materials used for fabrication of the elements were all subjected to sublimation purification and it was confirmed that the purity (absorption intensity area ratio at 254 nm) was 99.0% or more by using high performance liquid chromatography (TSKgel ODS-100Z, manufactured by Tosoh Corporation).

(2) Fabrication of Elements

A 0.5 mm-thick and 2.5 cm square glass substrate (manufactured by Geomatec Co., Ltd., surface resistance: 10Ω/□) having an ITO film thereon was put in a cleaning container. After ultrasonic cleaning in 2-propanol, the glass substrate was subjected to a UV-ozone treatment for 30 minutes. The following organic compound layers described in Table 1 below were deposited sequentially on this transparent anode (ITO film) by a vacuum deposition method. The film thickness was monitored by a quartz crystal oscillator.

1 nm of lithium fluoride and 100 nm of metallic aluminum were deposited in this order thereon, thereby forming a cathode. Further, a patterned mask (mask having a light emitting area of 2 mm×2 mm) was provided on the layer of lithium fluoride, and metallic aluminum was deposited.

The obtained laminate was put in a glove box purged with a nitrogen gas without bringing it into contact with the atmosphere and then sealed with a sealing can made of glass and an ultraviolet ray-curable adhesive (XNR5516HV, manufactured by Nagase-Chiba Ltd.), thereby obtaining the organic electroluminescent elements of the present invention and the comparative elements.

The configurations of the organic compound layers of the elements of the present invention and the comparative elements, prepared in each of Examples, are shown in Table 1 below. Further, 4-layer configurations were used in Examples 1 and 3 to 8, and a 5-layer configuration was used in Example 2. Further, the compounds F1 to F19 and the comparative compounds D1 to D6 were used as the light emitting materials of the light emitting layers in Examples 1 to 4, and the compounds F1 to F19 and the comparative compounds D1 to D6 were used as a host material in Examples 5 to 8.

In addition, in Table 1, the thickness (unit: nm) of each layer is shown in parenthesis.

TABLE 1

| | Configuration of organic compound layer |
|---|---|
| Example 1 | HAT-CN (10 nm)/NPD (30 nm)/ADN + light emitting material described in Table 2 below (mass ratio 95:5) (30 nm)/Balq (30 nm) |
| Example 2 | HIL-1 (10 nm)/HAT-CN (5 nm)/HTL-1 (30 nm)/HO-1 + light emitting material described in Table 3 below (mass ratio 95:5) (30 nm)/ETL-1 (30 nm) |
| Example 3 | HAT-CN (10 nm)/HTL-2 (30 nm) /HO-1 + light emitting material described in Table 4 below (mass ratio 93:7) (30 nm)/ETL-2 (30 nm) |
| Example 4 | HAT-CN (10 nm)/HTL-2 (30 nm) /HO-1 + light emitting material described in Table 5 below (mass ratio 93:7) (30 nm)/ETL-3 (30 nm) |
| Example 5 | HAT-CN (10 nm)/HTL-2 (30 nm)/host material described in Table 6 below + EMB-1 (mass ratio 95:5) (30 nm)/ETL-1 (30 nm) |
| Example 6 | HAT-CN (10 nm)/HTL-2 (30 nm)/host material described in Table 7 below + EMG-1 (mass ratio 95:5) (30 nm)/ETL-1 (30 nm) |
| Example 7 | HAT-CN (10 nm)/HTL-2 (30 nm)/host material described in Table 8 below + EMG-2 (mass ratio 95:5) (30 nm)/ETL-1 (30 nm) |
| Example 8 | HAT-CN (10 nm)/HTL-2 (30 nm)/host material described in Table 9 below + EMR-1 (mass ratio 95:5) (30 nm)/ETL-1 (30 nm) |

The materials other than F1 to F19 and D1 to D6 used for the fabrication of the organic electroluminescent elements in Example 1 to 8 are shown below.

[Chem. 41]

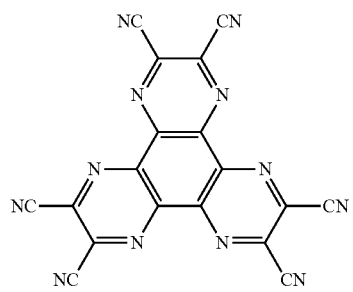

HAT-CN

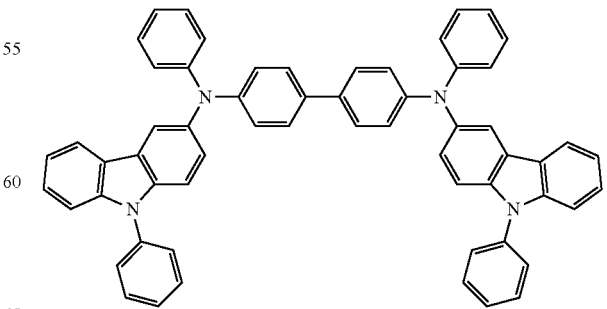

HIL-1

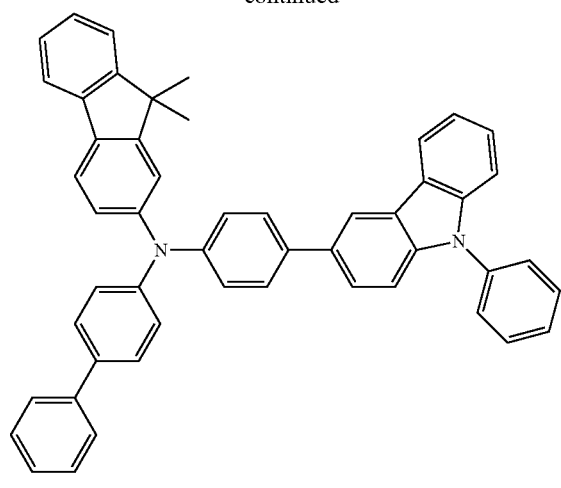
HTL-1
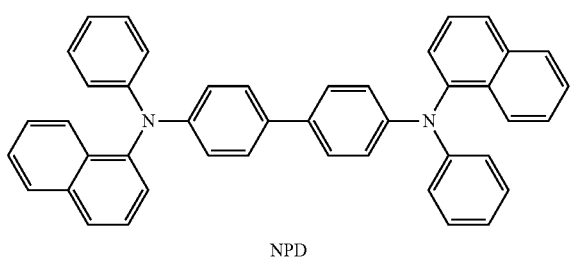
NPD
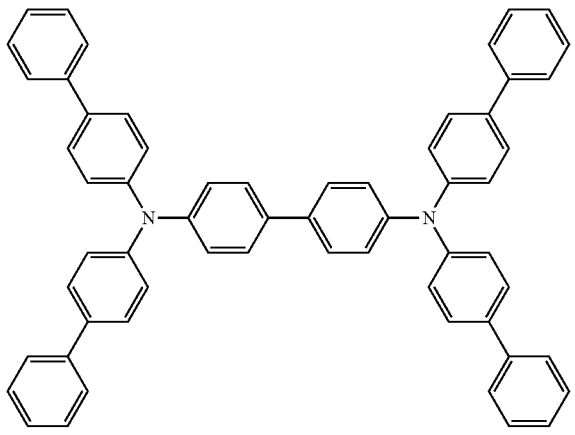
HTL-2
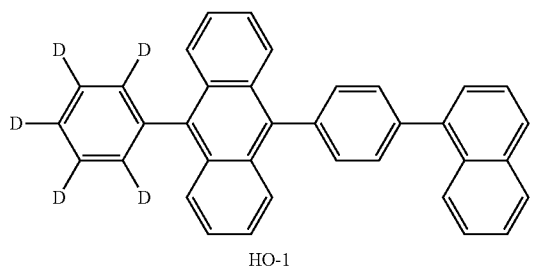
HO-1
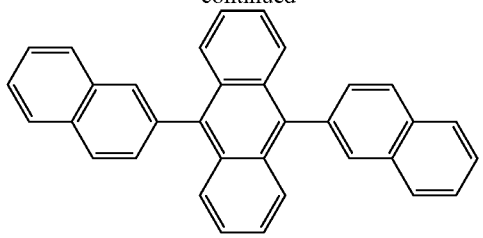
ADN
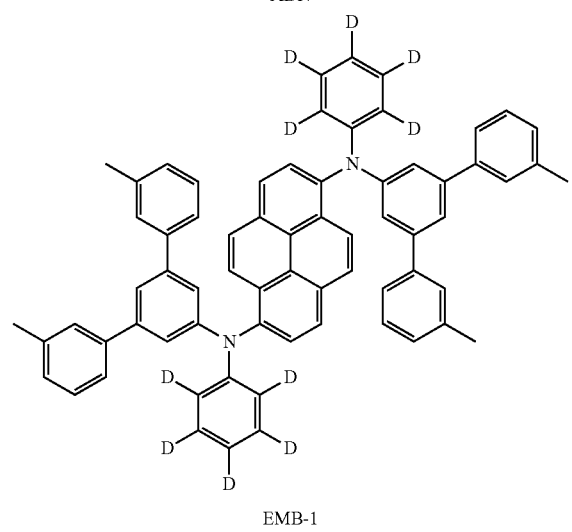
EMB-1
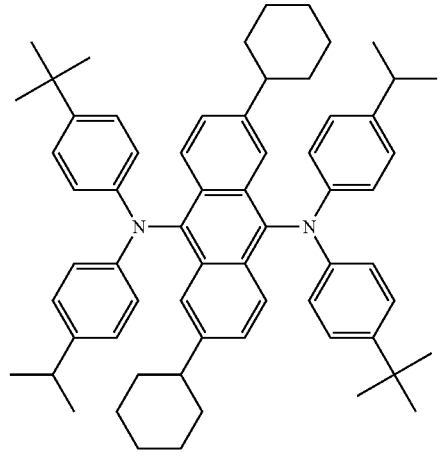
EMG-1
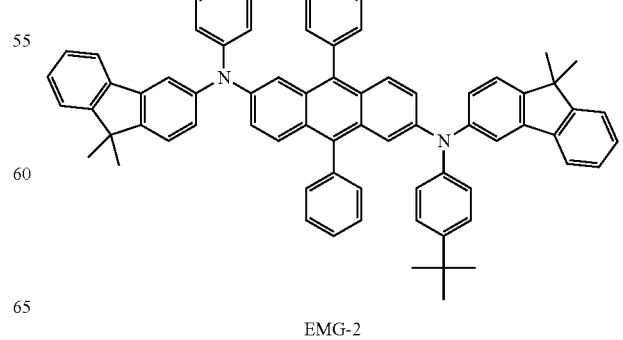
EMG-2

-continued

[Chem. 42]

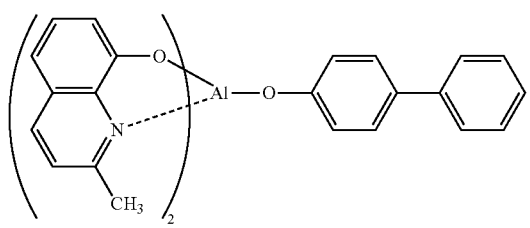

BALq

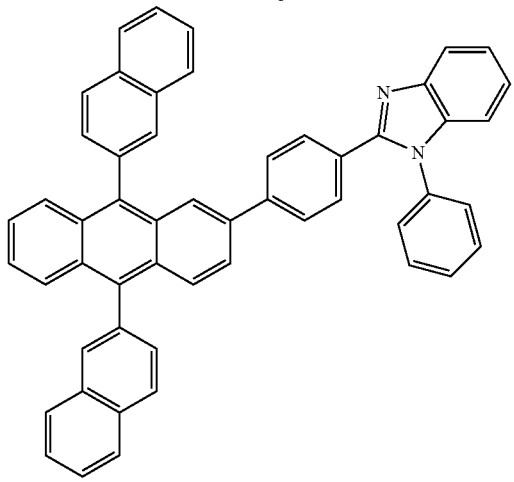

ETL-1

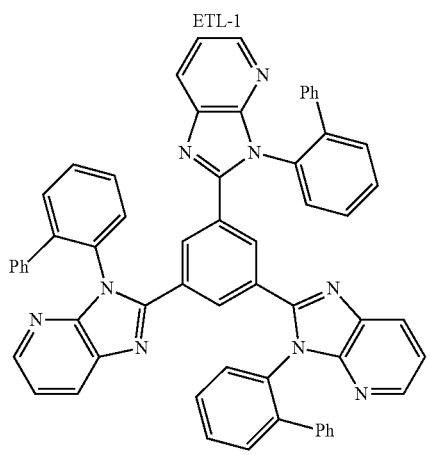

ETL-2

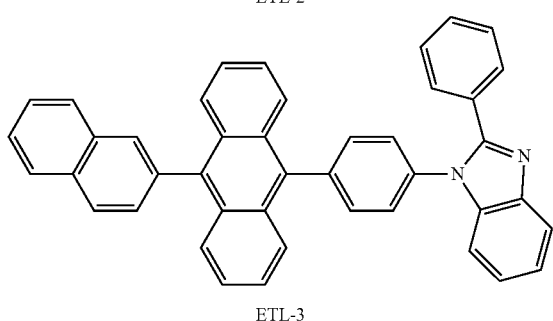

ETL-3

(3) Evaluation of Elements
(a) External Quantum Efficiency (Luminous Efficiency)

Light was emitted by applying a direct current voltage to an organic electroluminescent element at a constant current intensity (25 mA/cm$^2$) by using a source measure unit 2400 manufactured by TOYO Corporation. The luminance was measured using a luminance meter BM-8 manufactured by Topcon Corporation. The luminous spectrum and the light emitting wavelength were measured using a spectrum analyzer PMA-11 manufactured by Hamamatsu Photonics K. K. Based on these values, the external quantum efficiency was calculated by using a luminance conversion method, and shown as a relative value, taking the value of the comparative element 1-1, the comparative element 2-1, the comparative element 3-1, the comparative element 4-1, the comparative element 5-1, the comparative element 6-1, the comparative element 7-1, and the comparative element 8-1 in Tables 2 to 9 below as 1, in Tables 2 to 9 below. A larger numeral value of the external quantum efficiency is preferable.

(b) Aging Effect

A direct current voltage was applied to an organic electroluminescent element at a constant current intensity to give a luminance of 5000 cd/m$^2$, thereby emitting light continuously at the current intensity, and the element was driven until the luminance became 4000 cd/m$^2$. At that time, the time was expressed as A (h). A direct current voltage was applied again to the element after driving to give a luminance of 5000 cd/m$^2$, thereby emitting light continuously at the current intensity and the element was driven until the luminance became 4000 cd/m$^2$. At that time, the time was expressed as B (h). E=B/A was taken as an index for the effect of improving the element durability by aging. The results are shown in Tables 2 and 9 below. A larger value of E, which is more than 1, is preferable.

TABLE 2

| | Example 1 | | |
|---|---|---|---|
| | Light emitting material | External quantum efficiency | E value |
| Comparative element 1-1 | D1 | 1 | 0.73 |
| Comparative element 1-2 | D2 | 0.83 | 0.91 |
| Comparative element 1-3 | D3 | 1.13 | 1.10 |
| Comparative element 1-4 | D4 | 0.79 | 0.85 |
| Comparative element 1-5 | D5 | 0.92 | 0.95 |
| Comparative element 1-6 | D6 | 0.96 | 0.79 |
| Element 1-1 of the present invention | F1 | 1.29 | 1.10 |
| Element 1-2 of the present invention | F2 | 1.25 | 1.34 |
| Element 1-3 of the present invention | F3 | 1.29 | 1.29 |
| Element 1-4 of the present invention | F4 | 1.29 | 1.16 |
| Element 1-5 of the present invention | F5 | 1.25 | 1.33 |
| Element 1-6 of the present invention | F6 | 1.33 | 1.37 |
| Element 1-7 of the present invention | F7 | 1.38 | 1.45 |
| Element 1-8 of the present invention | F8 | 1.42 | 1.42 |
| Element 1-9 of the present invention | F9 | 1.42 | 1.19 |
| Element 1-10 of the present invention | F10 | 1.38 | 1.44 |
| Element 1-11 of the present invention | F11 | 1.21 | 1.38 |
| Element 1-12 of the present invention | F12 | 1.25 | 1.26 |
| Element 1-13 of the present invention | F13 | 1.25 | 1.19 |
| Element 1-14 of the present invention | F14 | 1.29 | 1.25 |

TABLE 2-continued

Example 1

| | Light emitting material | External quantum efficiency | E value |
|---|---|---|---|
| Element 1-15 of the present invention | F15 | 1.17 | 1.22 |
| Element 1-16 of the present invention | F16 | 1.25 | 1.29 |
| Element 1-17 of the present invention | F17 | 1.42 | 1.47 |
| Element 1-18 of the present invention | F18 | 1.42 | 1.46 |
| Element 1-19 of the present invention | F19 | 1.38 | 1.46 |

TABLE 3

Example 2

| | Light emitting material | External quantum efficiency | E value |
|---|---|---|---|
| Comparative element 2-1 | D1 | 1 | 0.75 |
| Comparative element 2-2 | D2 | 0.96 | 1.05 |
| Comparative element 2-3 | D3 | 1.22 | 1.10 |
| Comparative element 2-4 | D4 | 1 | 0.77 |
| Comparative element 2-5 | D5 | 0.87 | 0.84 |
| Comparative element 2-6 | D6 | 0.91 | 0.73 |
| Element 2-1 of the present invention | F1 | 1.43 | 1.16 |
| Element 2-2 of the present invention | F2 | 1.52 | 1.42 |
| Element 2-3 of the present invention | F3 | 1.57 | 1.55 |
| Element 2-4 of the present invention | F4 | 1.35 | 1.51 |
| Element 2-5 of the present invention | F5 | 1.30 | 1.53 |
| Element 2-6 of the present invention | F6 | 1.43 | 1.58 |
| Element 2-7 of the present invention | F7 | 1.61 | 1.49 |
| Element 2-8 of the present invention | F8 | 1.65 | 1.47 |
| Element 2-9 of the present invention | F9 | 1.70 | 1.32 |
| Element 2-10 of the present invention | F10 | 1.52 | 1.47 |
| Element 2-11 of the present invention | F11 | 1.48 | 1.59 |
| Element 2-12 of the present invention | F12 | 1.30 | 1.30 |
| Element 2-13 of the present invention | F13 | 1.35 | 1.28 |
| Element 2-14 of the present invention | F14 | 1.57 | 1.39 |
| Element 2-15 of the present invention | F15 | 1.30 | 1.37 |
| Element 2-16 of the present invention | F16 | 1.35 | 1.33 |
| Element 2-17 of the present invention | F17 | 1.70 | 1.51 |
| Element 2-18 of the present invention | F18 | 1.65 | 1.62 |
| Element 2-19 of the present invention | F19 | 1.70 | 1.55 |

TABLE 4

Example 3

| | Light emitting material | External quantum efficiency | E value |
|---|---|---|---|
| Comparative element 3-1 | D1 | 1 | 0.82 |
| Comparative element 3-2 | D2 | 0.82 | 1.00 |
| Comparative element 3-3 | D3 | 1.24 | 1.04 |
| Comparative element 3-4 | D4 | 1.19 | 0.84 |
| Comparative element 3-5 | D5 | 0.85 | 0.78 |
| Comparative element 3-6 | D6 | 0.94 | 0.83 |
| Element 3-1 of the present invention | F1 | 1.51 | 1.29 |
| Element 3-2 of the present invention | F2 | 1.62 | 1.51 |
| Element 3-3 of the present invention | F3 | 1.66 | 1.63 |
| Element 3-4 of the present invention | F4 | 1.59 | 1.52 |
| Element 3-5 of the present invention | F5 | 1.54 | 1.50 |
| Element 3-6 of the present invention | F6 | 1.48 | 1.60 |
| Element 3-7 of the present invention | F7 | 1.65 | 1.47 |
| Element 3-8 of the present invention | F8 | 1.89 | 1.51 |
| Element 3-9 of the present invention | F9 | 1.92 | 1.36 |
| Element 3-10 of the present invention | F10 | 1.77 | 1.59 |
| Element 3-11 of the present invention | F11 | 1.60 | 1.61 |
| Element 3-12 of the present invention | F12 | 1.51 | 1.58 |
| Element 3-13 of the present invention | F13 | 1.47 | 1.40 |
| Element 3-14 of the present invention | F14 | 1.69 | 1.51 |
| Element 3-15 of the present invention | F15 | 1.52 | 1.56 |
| Element 3-16 of the present invention | F16 | 1.51 | 1.38 |
| Element 3-17 of the present invention | F17 | 1.95 | 1.62 |
| Element 3-18 of the present invention | F18 | 1.88 | 1.70 |
| Element 3-19 of the present invention | F19 | 1.89 | 1.77 |

TABLE 5

Example 4

| | Light emitting material | External quantum efficiency | E value |
|---|---|---|---|
| Comparative element 4-1 | D1 | 1 | 0.79 |
| Comparative element 4-2 | D2 | 0.78 | 0.99 |
| Comparative element 4-3 | D3 | 1.04 | 1.11 |
| Comparative element 4-4 | D4 | 1.06 | 0.89 |
| Comparative element 4-5 | D5 | 0.97 | 0.79 |
| Comparative element 4-6 | D6 | 0.82 | 0.63 |
| Element 4-1 of the present invention | F1 | 1.52 | 1.30 |
| Element 4-2 of the present invention | F2 | 1.61 | 1.54 |
| Element 4-3 of the present invention | F3 | 1.63 | 1.61 |
| Element 4-4 of the present invention | F4 | 1.62 | 1.57 |
| Element 4-5 of the present invention | F5 | 1.53 | 1.51 |
| Element 4-6 of the present invention | F6 | 1.49 | 1.62 |

TABLE 5-continued

Example 4

| | Light emitting material | External quantum efficiency | E value |
|---|---|---|---|
| Element 4-7 of the present invention | F7 | 1.68 | 1.55 |
| Element 4-8 of the present invention | F8 | 1.85 | 1.56 |
| Element 4-9 of the present invention | F9 | 1.87 | 1.46 |
| Element 4-10 of the present invention | F10 | 1.69 | 1.62 |
| Element 4-11 of the present invention | F11 | 1.66 | 1.64 |
| Element 4-12 of the present invention | F12 | 1.53 | 1.60 |
| Element 4-13 of the present invention | F13 | 1.40 | 1.44 |
| Element 4-14 of the present invention | F14 | 1.71 | 1.58 |
| Element 4-15 of the present invention | F15 | 1.60 | 1.56 |
| Element 4-16 of the present invention | F16 | 1.54 | 1.40 |
| Element 4-17 of the present invention | F17 | 1.94 | 1.71 |
| Element 4-18 of the present invention | F18 | 1.82 | 1.70 |
| Element 4-19 of the present invention | F19 | 1.91 | 1.72 |

TABLE 6

Example 5

| | Host material | External quantum efficiency | E value |
|---|---|---|---|
| Comparative element 5-1 | D2 | 1 | 0.82 |
| Element 5-1 of the present invention | F1 | 1.54 | 1.48 |
| Element 5-2 of the present invention | F5 | 1.63 | 1.33 |

TABLE 7

Example 6

| | Host material | External quantum efficiency | E value |
|---|---|---|---|
| Comparative element 6-1 | D2 | 1 | 0.79 |
| Element 6-1 of the present invention | F1 | 1.49 | 1.36 |
| Element 6-2 of the present invention | F5 | 1.48 | 1.54 |

TABLE 8

Example 7

| | Host material | External quantum efficiency | E value |
|---|---|---|---|
| Comparative element 7-1 | D2 | 1 | 0.84 |
| Element 7-1 of the present invention | F1 | 1.52 | 1.35 |

TABLE 8-continued

Example 7

| | Host material | External quantum efficiency | E value |
|---|---|---|---|
| Element 7-2 of the present invention | F5 | 1.55 | 1.61 |

TABLE 9

Example 8

| | Host material | External quantum efficiency | E value |
|---|---|---|---|
| Comparative element 8-1 | D2 | 1 | 0.97 |
| Element 8-1 of the present invention | F1 | 1.50 | 1.24 |
| Element 8-2 of the present invention | F5 | 1.40 | 1.25 |

As clearly seen from the results in Tables 2 to 9 above, it could be found that any of the organic electroluminescent elements of the present invention, in which the compound represented by the general formula (I) was used as a light emitting material of the light emitting layer, and the organic electroluminescent elements of the present invention, in which the compounds represented by the general formula (I) was used as a host material of the light emitting layer had high luminous efficiency and a strong effect of improving the durability by driving aging, as compared with the comparative elements.

REFERENCE SIGNS LIST

2: SUBSTRATE
3: ANODE
4: HOLE INJECTING LAYER
5: HOLE TRANSPORTING LAYER
6: LIGHT EMITTING LAYER
7: HOLE BLOCKING LAYER
8: ELECTRON TRANSPORTING LAYER
9: CATHODE
10: ORGANIC ELECTROLUMINESCENT ELEMENT
11: ORGANIC LAYER
12: PROTECTIVE LAYER
14: ADHESIVE LAYER
16: SEALING ENCLOSURE
20: LIGHT EMITTING DEVICE
30: LIGHT SCATTERING MEMBER
31: TRANSPARENT SUBSTRATE
30A: LIGHT INCIDENT SURFACE
30B: LIGHT OUTPUTTING SURFACE
32: FINE PARTICLES
40: ILLUMINATION DEVICE

The invention claimed is:
1. An organic electroluminescent element comprising:
a substrate;
a pair of electrodes including an anode and a cathode, disposed on the substrate; and
at least one organic layer including a light emitting layer, disposed between the electrodes,
wherein at least one kind of compound represented by the following general formula (I) is contained in any layer of the at least one organic layer:

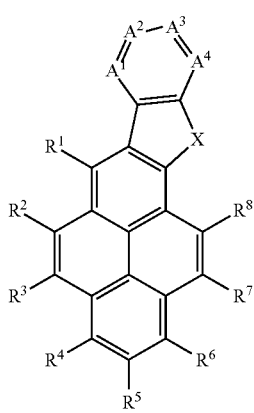

wherein X represents a linking group; $A^1$, $A^2$, $A^3$ and $A^4$ each independently represent C—R or an N atom; R's each independently represent a hydrogen atom or a substituent, but there is no case where R's, which are present in plural, are bonded to each other to form a ring; $R^1$ to $R^8$ each independently represent a hydrogen atom or a substituent, but there is no case where adjacent substituents selected from $R^1$ to $R^8$ are bonded to each other to form a ring, and at least one of $R^4$ and $R^6$ is an aryl group having 6 to 30 carbon atoms, a heteroaryl group having 3 to 30 carbon atoms, or a di-substituted amino group, with the proviso that $R^4$ or $R^6$ do not comprise an aryl group or a heteroaryl group, wherein the aryl group or heteroaryl group is substituted with a di-substituted amino group.

2. The organic electroluminescent element according to claim 1, wherein in the general formula (I), X is $CR^{12}R^{13}$, $NR^{14}$, $SiR^{15}R^{16}$, an O atom, or an S atom, wherein $R^{12}$, $R^{13}$, $R^{14}$, $R^{15}$ and $R^{16}$ are each independently represent a fluorine atom, an alkyl group, an aryl group, or a heteroaryl group.

3. The organic electroluminescent element according to claim 1, wherein in the general formula (I) $A^1$, $A^2$, $A^3$ and $A^4$ each independently represent C—R.

4. The organic electroluminescent element according to claim 1 wherein the compound represented by the general formula (I) is a compound represented by the following general formula (II):

wherein $R^1$ to $R^8$ and $R^{21}$ to $R^{24}$ represent a hydrogen atom or a substituent, provided there is no case where adjacent substituents selected from $R^1$ to $R^8$, $R^{21}$ to $R^{24}$ are bonded to each other to form a ring; $R^{14}$ represents an alkyl group, an aryl group, or a heteroaryl group.

5. The organic electroluminescent element according to claim 1, wherein in the compound represented by in the general formula (I), $R^4$ and $R^6$ are each independently an aryl group having 6 to 30 carbon atoms or a heteroaryl group having 5 to 30 carbon atoms.

6. The organic electroluminescent element according to claim 1, wherein in the compound represented by in the general formula (I), $R^1$, $R^2$, $R^3$, $R^5$, $R^7$ and $R^8$ are a hydrogen atom.

7. The organic electroluminescent element according to claim 1, wherein the molecular weight of the compound represented by the general formula (I) is 510 to 840.

8. The organic electroluminescent element according to claim 1, wherein the compound represented by the general formula (I) is contained in the light emitting layer.

9. The organic electroluminescent element according to claim 1, wherein the compound represented by the general formula (I) is a light emitting material contained in the light emitting layer.

10. The organic electroluminescent element according to claim 9, further comprising a host material in the light emitting layer.

11. The organic electroluminescent element according to claim 10, wherein the host material has an anthracene skeleton.

12. A light emitting device using the organic electroluminescent element according to claim 1.

13. A display device using the organic electroluminescent element according to claim 1.

14. An illumination device using the organic electroluminescent element according to claim 1.

15. A light emitting material for an organic electroluminescent element, represented by the following general formula (I):

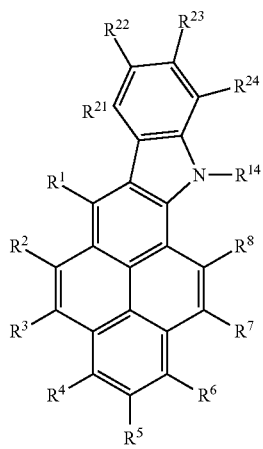

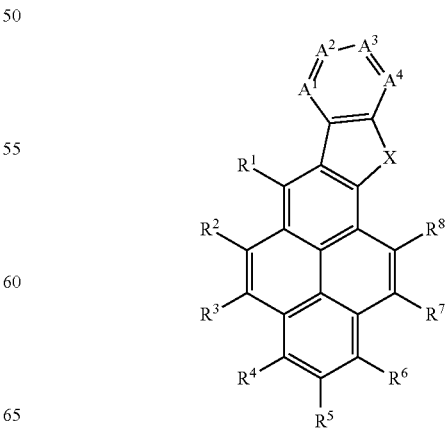

wherein X is $CR^{12}R^{13}$, $NR^{14}$, $SiR^{15}R^{16}$, an O atom, or an S atom, wherein $R^{12}$, $R^{13}$, $R^{14}$, $R^{15}$ and $R^{16}$ are each independently represent a fluorine atom, an alkyl group, an aryl group, or a heteroaryl group; $A^1$, $A^2$, $A^3$ and $A^4$ each independently represent C—R or an N atom; R's each independently represent a hydrogen atom or a substituent, but there is no case where R's, which are present in plural, are bonded to each other to form a ring; $R^1$ to $R^8$ each independently represent a hydrogen atom or a substituent, and at least one of $R^4$ and $R^6$ is an aryl group having 6 to 30 carbon atoms, a heteroaryl group having 3 to 30 carbon atoms, or a di-substituted amino group, but there is no case where adjacent substituents selected from $R^1$ to $R^8$ are bonded to each other to form a ring, with the proviso that $R^4$ or $R^6$ do not comprise an aryl group or a heteroaryl group, wherein the aryl group or heteroaryl group is substituted with a di-substituted amino group.

16. A light emitting material for an organic electroluminescent element, represented by the following general formula (I):

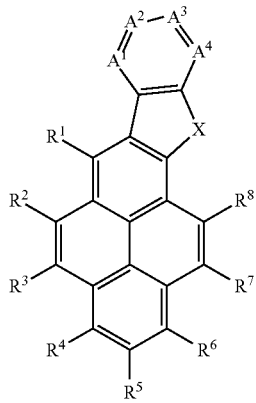

wherein X is $CR^{12}R^{13}$, $SiR^{15}R^{16}$, an O atom, or an S atom, wherein $R^{12}$, $R^{13}$, $R^{14}$, $R^{15}$ and $R^{16}$ are each independently represent a fluorine atom, an alkyl group, an aryl group, or a heteroaryl group; $A^1$, $A^2$, $A^3$ and $A^4$ each independently represent C—R or an N atom; R's each independently represent a hydrogen atom or a substituent, but there is no case where R's, which are present in plural, are bonded to each other to form a ring; $R^1$ to $R^8$ each independently represent a hydrogen atom or a substituent, but there is no case where adjacent substituents selected from $R^1$ to $R^8$ are bonded to each other to form a ring, and at least one of $R^4$ and $R^6$ represents a substituent.

* * * * *